United States Patent
Murthi et al.

(10) Patent No.: US 8,450,348 B2
(45) Date of Patent: May 28, 2013

(54) DERIVATIVES OF SQUARIC ACID WITH ANTI-PROLIFERATIVE ACTIVITY

(75) Inventors: Krishna K. Murthi, Andover, MA (US); Roland Köstler, Martinsried (DE); Chase Smith, Rutland, MA (US); Tilman Brandstetter, Munich (DE); Arthur F. Kluge, Lincoln, MA (US)

(73) Assignee: Forma TM, LLC, Watertown, MA (US)

( * ) Notice: Subject to any disclaimer, the term of this patent is extended or adjusted under 35 U.S.C. 154(b) by 1573 days.

(21) Appl. No.: 11/708,793

(22) Filed: Feb. 21, 2007

(65) Prior Publication Data

US 2008/0200523 A1    Aug. 21, 2008

(51) Int. Cl.
*A61K 31/44*    (2006.01)
*C07D 213/74*    (2006.01)

(52) U.S. Cl.
USPC ........ 514/352; 514/235.2; 514/318; 514/332; 546/194; 546/255; 546/304; 544/424

(58) Field of Classification Search
USPC ............... 514/235.5, 318, 332, 352; 546/194, 546/255, 304; 544/424
See application file for complete search history.

(56) References Cited

U.S. PATENT DOCUMENTS

| | | | |
|---|---|---|---|
| 4,522,943 A | 6/1985 | Algieri et al. | |
| 4,532,252 A | 7/1985 | Sach | |
| 5,532,245 A | 7/1996 | Butera et al. | |
| 5,736,137 A | 4/1998 | Anderson et al. | |
| 5,843,437 A | 12/1998 | Hamill et al. | |
| 5,976,456 A | 11/1999 | Ziani et al. | |
| 6,107,305 A | 8/2000 | Misra et al. | |
| 6,114,365 A | 9/2000 | Pevarello et al. | |
| 6,420,396 B1 | 7/2002 | Albers et al. | |
| 6,677,360 B2 | 1/2004 | Albers et al. | |
| 6,696,469 B2 | 2/2004 | Peglion | |
| 7,132,445 B2 * | 11/2006 | Taveras et al. | 514/438 |
| 2004/0053953 A1 * | 3/2004 | Taveras et al. | 514/277 |

FOREIGN PATENT DOCUMENTS

| | | |
|---|---|---|
| EP | 1 674 457 A1 | 6/2006 |
| WO | WO 95/14005 | 5/1995 |
| WO | WO 96/14300 | 5/1996 |
| WO | WO 96/15103 | 5/1996 |
| WO | WO 00/35855 | 6/2000 |
| WO | WO 00/35864 | 6/2000 |
| WO | WO 01/47867 | 7/2001 |
| WO | WO 01/87337 | 11/2001 |
| WO | WO 01/97338 | 12/2001 |
| WO | WO 02/04426 | 1/2002 |
| WO | WO 02/10136 | 2/2002 |
| WO | WO 02/42264 | 5/2002 |
| WO | WO 02/062761 | 8/2002 |
| WO | WO 02/076926 | 10/2002 |
| WO | WO 02/083624 | 10/2002 |

OTHER PUBLICATIONS hHead et al. "Preparation of novel . . . " Ca 136:167287 (2002).*
Lim et al. "Squaric acid . . . " J. Org. Chem. vol. 68 (24) 9233-9341 (2003).*
Tevyashova et al. "Formation of squaric . . . " Gioorg. Med. Chem. LEtt. v.14, 4783-4789 (2004).*
Urbahns et al. "Biphenyl as potent . . . " CA 147:514413 (2007).*
Greyer et al. "The national cancer . . . " Sem. orcology vol. 19(6) 622-638 (1992).*
Dorward "Side reactions in organic synthesis" p. IX (2005).*
Bible et al., *Cancer Research*, 57: 3375-3380 (1997).
Butera et al., *J. Med. Chem.*, 43: 1187-1202 (2000).
Gilbert et al., *J. Med. Chem.*, 43: 1203-1214 (2000).
Lien et al., *Trends in Biotechnology*, 21(12): 556-562 (2003).
Graham S. Poindexter, et al. "Dihydropyridine neuropeptide Y Y1 receptor antagonists 2: bioisosteric urea replacements",Biorganic& Medicinal Chemistry,(2004),vol. 12,pp. 507-521.
Jose Alexander, et al. "(Acyloxy)alkyl Carbamates as Novel Bioreversible Prodrugs for Amines:Increased Permeation through Biological Membranes",J.Med.Chem,1988,vol. 31,p. 318-322.

* cited by examiner

*Primary Examiner* — Celia Chang
(74) *Attorney, Agent, or Firm* — Gearhart Law, LLC

(57) ABSTRACT

The present invention provides derivatives of squaric acid, in particular derivatives of 3,4-diamino-cyclobut-3-ene-1,2-dione and tautomers and isomers thereof, as a single stereoisomer or a mixture of stereoisomers, or as a pharmaceutically acceptable salt thereof. These compounds show anti-proliferative activity, including against tumor cells, and are useful in the treatment of diseases including cancer.

13 Claims, No Drawings

DERIVATIVES OF SQUARIC ACID WITH ANTI-PROLIFERATIVE ACTIVITY

FIELD OF THE INVENTION

The present invention provides derivatives of squaric acid, in particular derivatives of 3,4-diamino-cyclobut-3-ene-1,2-dione and tautomers and isomers thereof, as a single stereoisomer or a mixture of stereoisomers, or as a pharmaceutically acceptable salt thereof. These compounds show anti-proliferative activity, including against tumor cells, and are useful in the treatment of diseases including cancer.

BACKGROUND OF THE INVENTION

A strong need exists to provide compositions, pharmaceuticals and/or medicaments with anti-proliferative activity. Such compositions, pharmaceuticals and/or medicaments may posses not only strong activity, but also exert diminished side effects in comparison to other anti-proliferative agents. Furthermore, the spectrum of tumors responsive to treatment with such compositions, pharmaceuticals and/or medicaments may be broad. Active ingredients of this type may be suitable in the mentioned indication as single agent, and/or in combination therapy, be it in connection with other therapeutic agents, with radiation, with operative/surgical procedures, heat treatment or any other treatment known in the mentioned indications.

One or more of such objectives is achieved, or other advantages shown, by making available the compounds of the present invention as defined herein. Compounds of the present invention are derivatives of squaric acid, in particular compounds of the present invention are derivatives of 3,4-diamino-cyclobut-3-ene-1,2-dione.

The compounds of the present invention can be suitable for further pre-clinical or clinical research and development towards the treatment of a variety of diseases including cancer, proliferative, degenerative and other diseases. The further development of such new therapeutic opportunities provided by the present invention would result in one or more effective therapies, and marketed drugs, for particularly debilitating diseases including those diseases and disorders listed herein.

It is known that various derivatives of squaric acid, substituted in a specific manner, have pharmacologically useful properties. In particular, certain derivatives of squaric acid are known to possess anti-proliferative activity. These compounds however are structurally dissimilar from the compounds of the present invention.

Compounds comprising 3,4-diamino-cyclobut-3-ene-1,2-dione moieties have been described as potassium channel openers (J Med Chem (2000) 43, 1187; J Med Chem (2000) 43, 1203; WO 02/062761), as smooth muscle relaxants (WO 96/15103; WO 96/14300; WO 95/14005), as chemokine receptor binders (WO 02/083624) or integrin receptor binders (WO 00/035864; U.S. Pat. No. 6,420,396; U.S. Pat. No. 6,677,360). U.S. Pat. No. 5,532,245 discloses compounds comprising a 3,4-diamino-cyclobut-3-ene-1,2-dione moiety. Clinical use of the compounds of U.S. Pat. No. 5,532,245 is disclosed as being limited to diseases amenable to treatment with smooth muscle relaxants, such as urinary incontinence or irritable bowel syndrome. WO00/35855 discloses compounds comprising a 3,4-diamino-cyclobut-3-ene-1,2-dione moieties for use in the treatment of inflammatory and autoimmune diseases. WO02/076926 discloses compounds comprising a 3,4-diamino-cyclobut-3-ene-1,2-dione moiety for the treatment of cancer. WO02/083624 discloses compounds comprising a 3,4-diamino-cyclobut-3-ene-1,2-dione moiety for the treatment of cancer. WO01/47867, WO02/04426, WO02/10136, and WO02/42264 disclose compounds comprising 3,4-diamino-cyclobut-3-ene-1,2-dione moieties as integrin antagonists. Compounds of these latter applications carry at least two aryl or heteroaryl substitutions on one amino group of the 3,4-diamino-cyclobut-3-ene-1,2-dione moiety and another aryl or heteroaryl substitution on the other amino group of the 3,4-diamino-cyclobut-3-ene-1,2-dione moiety. U.S. Pat. No. 6,677,360 discloses 3,4-diamino-cyclobut-3-ene-1,2-dione moieties as integrin antagonists. Compounds of this application carry at least two phenylene groups arranged in tandem.

SUMMARY OF THE INVENTION

The present invention provides compounds of general formula (I):

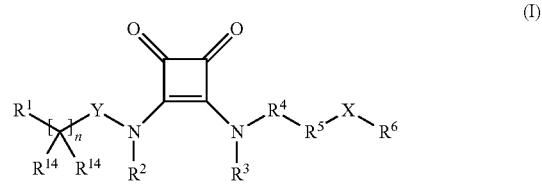

wherein:
n is 0 to 4;
Y is absent or —O—, —NR$^{14}$—, —S(=O)$_2$—, —C(=O)—;
R$^1$ is a monocyclic or fused or non-fused polycyclic aryl or heteroaryl group, which is substituted by p substituents R$^7$ (where p is an integer from 0 to 10),
and additionally, a substituent of R$^1$ may together with R$^2$ form a linker selected from the group consisting of C$_1$-C$_5$ alkylene and C$_2$-C$_5$ alkenylene;
R$^2$, R$^3$ are each independently hydrogen or alkyl, aryl, aralkyl, each of these groups may be optionally substituted by m substituents R$^8$ (where m is an integer from 0 to 5), or
R$^2$ and R$^3$ together with the N—C=C—N group may form a ring system having 5 to 15 atoms in the ring, selected from the group consisting of carbon and (in addition to the two nitrogen atoms carrying R$^2$ and R$^3$) 0-3 atoms selected from the group consisting of nitrogen, oxygen, and sulfur, and wherein the ring system is substituted by m substituents R$^8$ (where m is an integer from 0 to 5);
or R$^2$ and R$^3$ may each independently represent a structure selected from the group consisting of:

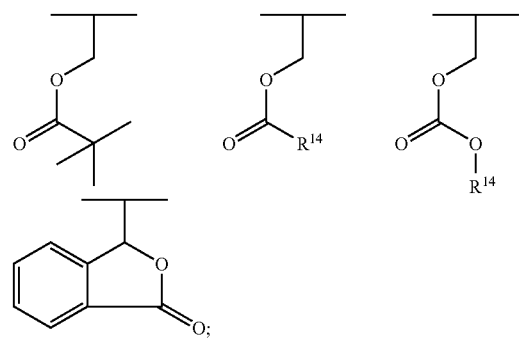

R⁴ is selected from the group consisting of —CH₂—, —O—, —SO₂—, —C(═O)— and —NH—;
R⁵ is a linker moiety selected from the group consisting of C₂-C₁₀ alkylene, C₂-C₁₀ alkenylene, C₂-C₁₀ alkynylene, —[C₀-C₅ alkylene/C₂-C₅ alkenylene/C₂-C₅ alkynylene-(carbocycle)-C₀-C₅ alkylene/C₂-C₅ alkenylene/C₂-C₅ alkynylene]-, —[C₀-C₅ alkylene/C₂-C₅ alkenylene/C₂-C₅ alkynylene-(heterocycle)-C₀-C₅ alkylene/C₂-C₅ alkenylene/C₂-C₅ alkynylene]-, which linker moiety is substituted by k substituents R⁹ (where k is an integer from 0 to 10);
X is a group A-B-C, wherein
A is absent or —O—, —NR¹⁴—, —S—;
B is absent or —C(═O)—, —S(═O)—, —S(═O)₂—, —C(═N—CN)—, —C(═N—NO₂)—;
C is absent or —O—, —NR¹⁴—, —S—;
R⁶ is a carbon atom or a saturated or unsaturated carbocycle or heterocycle, each substituted by hydrogen and/or q substituents R¹⁰ (where q is an integer from 0 to 10);
each R⁷, R⁸, R⁹, R¹⁰ is independently selected from the group consisting of alkyl, alkenyl, alkynyl, alkoxy, aryl, aralkyl, cycloalkyl, cycloalkylalkyl, haloalkyl, haloalkenyl, haloalkynyl, heterocyclyl, heterocyclylalkyl, halo, nitro, cyano, hydroxy, amino, carboxy, —OR¹¹, —NHR¹¹, —NR¹¹R¹², —C(O)H, —C(O)R¹¹, —OC(O)R¹¹, —C(O)OR¹¹, —C(O)NHR¹¹, —C(O)NR¹¹R¹², —S(O)ₓR¹¹ (where X is 0 to 2), —S(O)₂OR¹¹, —R¹³-nitro, —R¹³-cyano, —R¹³-hydroxy, —R¹³-amino, —R¹³-carboxy, —R¹³—OR¹¹, —R¹³—NHR¹¹, —R¹³—NR¹¹R¹², —R¹³—C(O)H, —R¹³—C(O)R¹¹, —R¹³—OC(O)R¹¹, —R¹³—C(O)OR¹¹, —R¹³—C(O)NHR¹¹, —R¹³—C(O)NR¹¹R¹², —R¹³—S(O)ₓR¹¹ (where X is 0 to 2), —R¹³—S(O)₂OR¹¹; —O—R¹³-nitro, —O—R¹³-cyano, —O—R¹³-hydroxy, —O—R¹³-amino, —O—R¹³-carboxy, —O—R¹³—OR¹¹, —O—R¹³—NHR¹¹, —O—R¹³—NR¹¹R¹², —O—R¹³—C(O)H, —O—R¹²—C(O)R¹¹, —O—R¹³—OC(O)R¹¹, —O—R¹³—C(O)OR¹¹, —O—R¹³—C(O)NHR¹¹, —O—R¹³—C(O)NR¹¹R¹², —O—R¹³—S(O)ₓR¹¹ (where X is 0 to 2), —O—R¹³—S(O)₂OR¹¹; —N(R¹⁴)—R¹³-nitro, —N(R¹⁴)—R¹³-cyano, —N(R¹⁴)—R¹³-hydroxy, —N(R¹⁴)—R¹³-amino, —N(R¹⁴)—R¹³-carboxy, —N(R¹⁴)—R¹³—OR¹¹, —N(R¹⁴)—R¹³—NHR¹¹, —N(R¹⁴)—R¹³—NR¹¹R¹², —N(R¹⁴)—R¹³—C(O)H, —N(R¹⁴)—R¹³—C(O)R¹¹, —N(R¹⁴)—R¹³—OC(O)R¹¹, —N(R¹⁴)C(O)R¹¹—, —O—R¹³—N(R¹⁴)—C(O)R¹¹—, —N(R¹⁴)—R¹³—C(O)OR¹¹, —N(R¹⁴)—R¹³—C(O)NHR¹¹, —N(R¹⁴)—R¹³—C(O)NR¹¹R¹², —N(R¹⁴)—R¹³—S(O)ₓR¹¹ (where X is 0 to 2), —N(R¹⁴)—R¹³—S(O)₂OR¹¹;
R¹¹, R¹² are each independently selected from the group consisting of alkyl, alkenyl, alkynyl, aryl, aralkyl, cycloalkyl, cycloalkylalkyl, haloalkyl, haloalkenyl, haloalkynyl, heterocyclyl, heterocyclylalkyl, or if R¹¹ and R¹² are both bound to a nitrogen atom, together with the nitrogen atom form a 5-7 membered ring consisting of carbon and 0-2 additional heteroatoms selected from the group consisting of O, S and N (where the N is bound to a further substituent selected from the group consisting of hydrogen, alkyl, aryl, and aralkyl), which ring system may be partially unsaturated;
each R¹³ is independently selected from the group consisting of C₁-C₆ alkylene, C₂-C₆ alkenylene, C₂-C₆ alkynylene;
each R¹⁴ is independently selected from the group consisting of hydrogen, alkyl, alkenyl, alkynyl, aryl, aralkyl, cycloalkyl, cycloalkylalkyl, haloalkyl, haloalkenyl, haloalkynyl, heterocyclyl, heterocyclylalkyl;
or tautomers or isomers thereof;
as a single stereoisomer or a mixture of stereoisomers;
or as a pharmaceutically acceptable salt thereof.

In other embodiments of the invention, if R1 is a fused or non-fused polycyclic aryl or heteroaryl group, then n may be 5, greater than 5, 7, greater than 7, 9, greater than 9, 11 or greater than 11.

The present invention also provides compounds of general formula (Ia):

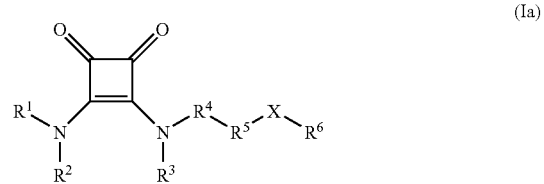

(Ia)

wherein
R¹ is 3-pyridyl or 4-pyridyl;
R², R³ are each hydrogen;
R⁴ is —CH₂—;
R⁵ is a linker moiety selected from the group consisting of C₂-C₁₀ alkylene, C₂-C₁₀ alkenylene, C₂-C₁₀ alkynylene, —[C₀-C₅ alkylene/C₂-C₅ alkenylene/C₂-C₅ alkynylene-(carbocycle)-C₀-C₅ alkylene/C₂-C₅ alkenylene/C₂-C₅ alkynylene]- and —[C₀-C₅ alkylene/C₂-C₅ alkenylene/C₂-C₅ alkynylene-(heterocycle)-C₀-C₅ alkylene/C₂-C₅ alkenylene/C₂-C₅ alkynylene]-, which linker moiety is substituted by k substituents R⁹ (where k is an integer from 0 to 10);
X is absent or selected from the group consisting of —O—, —S— and —NH—;
R⁶ is a carbocycle or a heterocycle, wherein said carbocycle or heterocycle is substituted with 0-5 substituents R¹⁰;
each R⁹ and R¹⁰ is independently selected from the group consisting of alkyl, alkenyl, alkynyl, alkoxy, aryl, aralkyl, cycloalkyl, cycloalkylalkyl, haloalkyl, haloalkenyl, haloalkynyl, heterocyclyl, heterocyclylalkyl, halo, nitro, cyano, hydroxy, amino, carboxy, —OR¹¹, —NHR¹¹, —NR¹¹R¹², —C(O)H, —C(O)R¹¹, —OC(O)R¹¹, —C(O)OR¹¹, —C(O)NHR¹¹, —C(O)NR¹¹R¹², —S(O)ₓR¹¹ (where X is 0 to 2), —S(O)₂OR¹¹, —R¹³-nitro, —R¹³-cyano, —R¹³-hydroxy, —R¹³-amino, —R¹³-carboxy, —R¹³—OR¹¹, —R¹³—NHR¹¹, —R¹³—NR¹¹R¹³, —R¹³—C(O)H, —R¹³—C(O)R¹¹, —R¹³—OC(O)R¹¹, —R¹³—C(O)OR¹¹, —R¹³—C(O)NHR¹¹, —R¹³—C(O)NR¹¹R¹², —R¹³—S(O)ₓR¹¹ (where X is 0 to 2), —R¹³—S(O)₂OR¹¹; —O—R¹³-nitro, —O—R¹³-cyano, —O—R¹³-hydroxy, —O—R¹³-amino, —O—R¹³-carboxy, —O—R¹³—OR¹¹, —O—R¹³—NHR¹¹, —O—R¹³—NR¹¹R¹², —O—R¹³—C(O)H, —O—R¹³—C(O)R¹¹, —O—R¹³—OC(O)R¹¹, —O—R¹³—C(O)OR¹¹, —O—R¹³—C(O)NHR¹¹, —O—R¹³—C(O)NR¹¹R¹², —O—R¹³—S(O)ₓR¹¹ (where X is 0 to 2), —O—R¹³—S(O)₂OR¹¹; —N(R¹⁴)—R¹³-nitro, —N(R¹⁴)—R¹³-cyano, —N(R¹⁴)—R¹³-hydroxy, —N(R¹⁴)—R¹³-amino, —N(R¹⁴)—R¹³-carboxy, —N(R¹⁴)—R¹³—OR¹¹, —N(R¹⁴)—R¹³—NHR¹¹, —N(R¹⁴)—R¹³—NHR¹¹, —N(R¹⁴)—R¹³—C(O)H, —N(R¹⁴)—R¹³—C(O)R¹¹, —N(R¹⁴)—R¹³—OC(O)R¹¹, —N(R¹⁴)C(O)R¹¹—, —O—R¹³—N(R¹⁴)—C(O)R¹¹—, —N(R¹⁴)—R¹³—C(O) OR¹¹, —N(R¹⁴)—R¹³—C(O)NHR¹¹, —N(R¹⁴)—R¹³—C(O)NR¹¹R¹², —N(R¹⁴)—R¹³—S(O)ₓR¹¹ (where X is 0 to 2), —N(R¹⁴)—R¹³—S(O)₂OR¹¹, (morpholin-4-yl)C₁-C₆ alkyl or (morpholin-4-yl)C₁-C₆ alkoxy;
R¹¹, R¹² are each independently selected from the group consisting of alkyl, alkenyl, alkynyl, aryl, aralkyl, cycloalkyl, cycloalkylalkyl, haloalkyl, haloalkenyl, haloalkynyl, heterocyclyl, heterocyclylalkyl, or if R¹¹ and R¹² are both bound to a nitrogen atom, together with the nitrogen atom form a 5-7 membered ring consisting of carbon and 0-2 additional heteroatoms selected from the group consisting of O, S and N (where the N is bound to a further substituent selected from the group consisting of hydrogen, alkyl, aryl, and aralkyl), which ring system may be partially unsaturated;

each $R^{13}$ is independently selected from the group consisting of $C_1$-$C_6$ alkylene, $C_2$-$C_6$ alkenylene, $C_2$-$C_6$ alkynylene;

each $R^{14}$ is independently selected from the group consisting of hydrogen, alkyl, alkenyl, alkynyl, aryl, aralkyl, cycloalkyl, cycloalkylalkyl, haloalkyl, haloalkenyl, haloalkynyl, heterocyclyl, heterocyclylalkyl;

or tautomers or isomers thereof;

as a single stereoisomer or a mixture of stereoisomers;

or as a pharmaceutically acceptable salt thereof.

The present invention further provides the compounds of the present invention for use in therapy. In other aspects, the invention further provides the compounds of the present invention for prophylatic uses. In certain embodiments, said therapy or prophylactic use is the treatment or prevention of a proliferative disorder, such as a tumor or cancer.

The present invention further provides the use of a compound of the present invention for the preparation of a pharmaceutical composition for the treatment of a mammal, for example a human, having a proliferative disorder, such as a tumor or cancer.

The present invention further provides for the use of a compounds of the present invention in therapy, e.g. for use in the treatment of a disease or disorder, such as cancer.

The present invention further provides for the use of a compound of the present invention for the preparation of a composition for killing or inhibiting the growth of a cell, wherein said cell may be a cancer cell, and wherein said cell may be an in vitro cell, i.e. a cell grown in vitro.

The present invention furthermore provides a method for treating a mammal, preferably a human, having, exhibiting or suffering from a proliferative disorder or disease, such as a tumor or cancer, comprising administering to said mammal a pharmaceutically effective amount of a compound of the present invention.

The present invention also provides a method for prophylactic treatment of a mammal, preferably a human, the intent of which is to reduce the frequency of, delay the onset of, or the symptoms of a medical condition, such as cancer, in a subject relative to a subject which does not receive the composition.

The present invention furthermore provides a method of treating or preventing a proliferative disorder or disease, such as a tumor or cancer, comprising administering to an individual in need thereof a compound of the present invention.

The present invention furthermore provides a pharmaceutical package, wherein said package includes a compound of the present invention. The compound of the present invention may be formulated together with another pharmaceutical ingredient. Alternatively, the compound of the present invention and another pharmaceutical ingredient may be formulated separately and in individual dosage amounts.

In a preferred embodiment, the compounds described and claimed herein show greater than 20%, preferably greater than 30%, 50%, or even 80% inhibition of tumor cell growth in the SRB assay, e.g., the SRB assay described herein.

In another preferred embodiment, the compounds described and claimed herein show an $IC_{50}$ [µM] value <10, preferably <1, <0.1, <0.02, or even 0.01, in the inhibition of tumor cell growth, e.g., in the $IC_{50}$ assay described herein.

In another preferred embodiment, the compounds described and claimed herein lead to a loss of tumor cell viability in a clonogenic survival assay, e.g., in the clonogenic survival assay described herein.

In one embodiment, the tumor cell in respect of which the compound shows inhibition of cell growth, or leads to a loss of cell viability, is a tumor cell derived from a tumor cell line, for example, a cell selected from an A2780, an HCT-116, a PC-3, an SW-620, an MCF7, or a A-549 cell.

DETAILED DESCRIPTION OF THE INVENTION

Definitions

The term "alkyl" refers to optionally substituted straight- or branched-chain saturated hydrocarbon groups having from 1 to about 20 carbon atoms, including from 1 to about 7 carbon atoms. These groups may or may not be branched. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl. It will also be understood by those skilled in the art that the substituted moieties themselves can be substituted as well when appropriate. In certain embodiments alkyl groups are unsubstituted.

The term "lower alkyl" refers to those alkyl groups having from 1 to about 6 carbon atoms, and in certain embodiments from 1 to 4 carbon atoms, and the term "lower alkoxy" refers to such lower alkyl groups attached to an oxygen atom. In certain embodiments, alkyl substituents may be lower alkyl substituents.

The terms "alkenyl" and "alkynyl" herein refer to alkenyl and alkynyl groups having 2 to about 20 carbon atoms, respectively. The terms "alkenyl" and "alkynyl" refer to monovalent groups. The terms "alkenylene" and "alkynylene" refer to the corresponding divalent groups. These groups may or may not be branched. At least one of the bonds of an alkenyl or an alkenylene group is a double bond, other, additional, bonds may be single bonds or double bonds. At least one of the bonds of an alkynyl or an alkynylene group is a triple bond, other, additional, bonds may be single bonds, double bonds or triple bonds. Examples of such alkenyl (and alkenylene) groups include ethenyl(ethenylene), 1-propenyl (1-propenylene), 2-propenyl (2-propenylene), 1-butenyl(1-butenylene), 2-butenyl(2-butenylene), 3-butenyl(3-butenylene), 2-methyl-1-propenyl(2-methyl-1-propenylene), 2-methyl-2-propenyl(2-methyl-2-propenylene), and the like. Examples of such alkynyl (and alkynylene) groups include ethynyl(ethynylene), 1-propynyl(1-propynylene), 2-propynyl(2-propynylene), and so forth. In addition, the terms are intended to include both unsubstituted and substituted alkenyl and alkenylene groups. Substituted alkenyl and alkenylene groups refer to alkenyl and alkenylene moieties having one or more hydrogen substituents replaced by, but not limited to halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl. The same applies for alkynyl and alkynylene groups, which may be unsubstituted or substituted with the substituents indicated above. In certain embodiments alkenyl, alkynyl, alkenylene and alkynylene groups are unsubstituted.

It will also be understood by those skilled in the art that the substituted moieties themselves can be substituted as well when appropriate.

The term "cycloalkyl" and "bicycloalkyl" refers to any stable and optionally substituted saturated cyclic hydrocarbon ring systems, which may contain 3 to about 12 carbons per ring. Exemplary groups include cyclopropyl, cyclobutyl, cyclopentyl, cyclohexyl, cycloheptyl, cyclooctyl, cyclodecyl, cyclododecyl, norbornyl, bicyclononyl, or tetrahydronaphthyl(tetralin) and adamantyl. Exemplary substituents include one or more alkyl groups as described above, or one or more of the groups described above as substituents for alkyl groups. In certain embodiments cycloalkyl and bicycloalkyl groups are unsubstituted.

The term "halogen" or "halo" refers to fluorine, chlorine, bromine and iodine.

The term "aryl" is intended to mean any stable and optionally substituted monocyclic or polycyclic aromatic moiety, which may contain 3 to about 12 members per ring. This includes optionally substituted benzene rings or optionally substituted benzene ring systems fused to one or more optionally substituted benzene rings, to form, e.g., anthracene, phenanthrene, or naphthalene ring systems, or fused to heteroaryl rings. Aryl moieties may be optionally substituted with between 0 to about 10 substituents, and in certain embodiments greater than 10 substituents. Such substituents may be selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino (optionally substituted by alkyl, aryl, or heteroaryl), carboxy, tetrazolyl, carboxamide, carbamoyl (optionally substituted by alkyl, aryl, or heteroaryl), aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylureido, alkylureido, cycloalkylureido, alkylthioureido, aryloxy, aralkoxy, or —O(CH$_2$)$_n$COOH, —(CH$_2$)$_n$COOH, —C(O)O(CH$_2$)$_n$R, —(CH2)$_n$N(H)C(O)OR, or —N(R')S(0)$_2$R wherein n is 1-4 and R is —H, alkyl, aryl or heteroaryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, triazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof. Examples of aryl groups include phenyl, p-tolyl, 4-methoxyphenyl, 4-tert-butoxyphenyl, 3-methylmethoxyphenyl, 4-fluorophenyl, 4-chlorophenyl, 3-nitrophenyl, 3-aminophenyl, 3-acetamidophenyl, 4-acetamidophenyl, 2-methyl acetamidophenyl, 2-methyl aminophenyl, 3-methyl aminophenyl, 2-amino methylphenyl, 2,4-dimethyl aminophenyl, 4-hydroxyphenyl, 3-methyl hydroxyphenyl, 1-naphthyl, 2-naphthyl, 3-amino-1-naphthyl, 2-methyl amino naphthyl, 6-amino naphthyl, 4,6-dimethoxy naphthyl and the like. In certain embodiments aryl moieties are unsubstituted. Aryl moieties that do not contain any heteroatoms are designated "homoaryl" moieties. Heteroaryl moieties and homoaryl moieties are aryl moieties.

As used herein, the term "heteroaryl" refers to any stable and optionally substituted mono- or polycyclic aromatic moiety containing one or more nitrogen, sulfur, and/or oxygen heteroatoms, where N-oxides and sulfur oxides and dioxides are permissible heteroatom substitutions. Heteroaryl moieties may contain 3 to about 12 members per ring and may be optionally substituted with between 0 to about 10 substituents, and in certain embodiments greater than 10 substituents. Such substituents may be selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl, aryl, or heteroaryl, carboxy, tetrazolyl, carboxamide, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylureido, alkylureido, cycloalkylureido, alkylthiourea, aryloxy, aralkoxy, or —O(CH$_2$)$_n$COOH, —(CH$_2$)$_n$COOH, —C(O)O(CH$_2$)$_n$R, —(CH$_2$)$_n$N(H)C(O)OR, or —N(R')S(0)$_2$R wherein n is 1-4 and R is —H, alkyl, aryl or heteroaryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof. In certain embodiments heteroaryl moieties are unsubstituted.

As used herein, "carbocycle" or "carbocyclic residue" is intended to mean any stable monocyclic or polycyclic system which consists of carbon atoms, any of which may be saturated, partially unsaturated, or aromatic. Each ring may comprise between 3 and about 12 members. Examples of such carbocycles include, but are not limited to, cyclopropyl, cyclobutyl, cyclopentyl, cyclohexyl, cycloheptyl, adamantyl, cyclooctyl, bicyclooctanes, such as [3.3.0]bicyclooctane, bicyclononanes, such as [4.3.0]bicyclononane, bicyclodecanes(decalins), such as [4.4.0]bicyclodecane(decalin), bicyclooctanes, such as [2.2.2]bicyclooctane, fluorenyl, phenyl, naphthyl, indanyl, adamantyl, or tetrahydronaphthyl(tetralin). A carbocycle may be substituted with one or more of the above substituents. In certain embodiments carbocycles and carbocyclic residues are unsubstituted. Aryl residues are encompassed in the terms "carbocycle" or "carbocyclic residue".

As used herein, the term "heterocycle" or "heterocyclic system" is intended to mean any stable monocyclic or polycyclic ring system, any ring of which is saturated, partially unsaturated, or unsaturated (aromatic/heteroaryl), and which consists of carbon atoms and at least one heteroatom independently selected from the group consisting of N, O and S. The nitrogen and sulfur heteroatoms may optionally be oxidized. The heterocyclic ring may be attached to its pendant group at any heteroatom or carbon atom that results in a stable structure. Each ring may comprise between 3 and about 12 members. The heterocyclic rings described herein may be substituted on carbon or on a nitrogen atom if the resulting compound is stable, including one or more of the substituents of above. In certain embodiments a nitrogen in the heterocycle may optionally be quaternized. In certain embodiments, when the total number of S and O atoms in the heterocycle exceeds 1, then these heteroatoms need not be adjacent to one another. In particular embodiments the total number of S atoms in the heterocycle is not more than 1. In certain embodiments heterocycles and heterocyclic systems are unsubstituted.

As used herein, the term "aromatic heterocyclic system" is intended to mean any stable optionally substituted monocyclic or polycyclic system, where each ring may comprise between 3 and about 12 members, and which consists of carbon atoms and from 1 to about 4 heteroatoms independently selected from N, O and S. In certain embodiments, the total number of S and O atoms in the aromatic heterocycle is not more than 1. Examples of heterocyclic groups include, but are not limited to, 1H-indazolyl, 2-pyrrolidonyl, 2H6H dithiazinyl, 2H-pyrrolyl, 3H-indolyl, 4-piperidonyl, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benzisoxazolyl, benzisothiazolyl, benzimidazalonyl, carbazolyl, 4aH-carbazolyl, P-carbolinyl, chromanyl, chromenyl, cinnolinyl, decahydroquinolinyl, 2H,6H dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles. In certain embodiments aromatic heterocyclic system are unsubstituted.

"Substituted" is intended to indicate that one or more hydrogens on the atom or group indicated in the expression using "substituted" is replaced with a selection from the indicated group(s), provided that the indicated atom's normal valency, or that of the appropriate atom of the group that is substituted, is not exceeded, and that the substitution results in a stable compound. When a substituent is keto or oxo (i.e., =O) group, then 2 hydrogens on the atom are replaced. Keto/oxo substituents are not direct substituents of aromatic moieties. Exemplary substituents include, for example, an alkyl, a perfluoroalkyl (such as trifluoromethyl), a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety. It will be understood by those skilled in the art that substituents, such as heterocyclyl, aryl, alkyl, etc., can themselves be substituted, if appropriate.

The term "IC50", as used herein, refers to concentrations at which a measurable activity, phenotype or response, for example growth of cells such as tumor cells, is inhibited by 50%. IC50 values can be estimated from an appropriate dose-response curve, for example by eye or by using appropriate curve fitting or statistical software. More accurately, IC50 values may be determined using non-linear regression analysis.

As used herein, an "individual" means a multi-cellular organism, for example an animal such as a mammal, including a primate. In addition to primates, such as humans, a variety of other mammals can be treated according to the method of the present invention. For example, mammals including, but not limited to, cows, sheep, goats, horses, dogs, cats, guinea pigs, rats or other bovine, ovine, equine, canine, feline, rodent or murine species can be used.

As used herein, a "proliferative disorder" or a "proliferative disease" includes a disease or disorder that affects a cellular growth, differentiation, or proliferation process. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic diseases or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a benign or malignant mass of tissue. Examples of cellular growth or proliferation disorders include, but are not limited to tumors, cancer, autoimmune diseases, viral diseases, fungal diseases, neurodegenerative disorders and cardiovascular diseases.

As used herein, the terms "anti-cancer" or "anti-proliferative" refer to compounds with anti-cancer and anti-proliferative properties, respectively. These agents include, but are not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, satraplatin, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, JM 118, etoposide, teniposide, vinblastine, vincristine, vinorelbine, procarbazine, asparaginase, pegaspargase, octreotide, estramustine, and hydroxyurea. Said terms also include, but are not limited to, other non-small molecule therapeutics, such as antibodies, e.g. ID09C3 and other anti-HLA-DR antibodies as described in WO 01/87337 and WO 01/97338, Rituxan as described in U.S. Pat. Nos. 5,736,137, 5,776,456, 5,843,437, 4D5, Mab225, C225, Daclizumab (Zenapax), Antegren, CDP 870, CMB-401, MDX-33, MDX-220, MDX-477, CEA-CIDE, AHM, Vitaxin, 3622W94, Therex, 5G1.1, IDEC-131, HU-901, Mylotarg, Zamyl (SMART M195), MDX-210, Humicade, LymphoCIDE, ABX-EGF, 17-1A, Trastuzumab (Herceptin®, rhuMAb), Epratuzumab, Cetuximab (Erbitux®), Pertuzumab (Omnitarg®, 2C4), R3, CDP860, Bevacizumab (Avastin®), tositumomab (Bexxar®), Ibritumomab tiuxetan (Zevalin®), M195, 1D10, Hu1D10 (Remitogen®, apolizumab), Danton/DN1924, an "HD" antibody such as HD4 or HD8, CAMPATH-1 and CAMPATH-1H or other variants, fragments, conjugates, derivatives and modifications thereof, or other equivalent compositions with improved or optimized properties, and proteins or peptides, e.g. those described in Trends in Biotechnology (2003), 21(12), p. 556-562.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids.

For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, EtOAc, ethanol, isopropanol, or acetonitrile are preferred. Lists of suitable salts are found in *Remington's Pharmaceutical Sciences,* 18th ed., Mack Publishing Company, Easton, Pa., 1990, p. 1445, the disclosure of which is hereby incorporated by reference.

Any salt that retains the desired biological activity of the compounds contained herein and that exhibits minimal or no undesired or toxicological effects is intended for inclusion here. Pharmaceutically acceptable salts include those derived from pharmaceutically acceptable organic or inorganic acids and bases. Non-pharmaceutically acceptable acids and bases also find use herein, as for example, in the synthesis and/or purification of the compounds of interest. Thus, all "salts" are also encompassed within the scope of the instant invention.

Non-limiting examples of suitable salts include those derived from inorganic acids, such as, for example, hydrochloric acid, hydrobromic acid, sulfuric acid, phosphoric acid, nitric acid, bicarbonic acid, carbonic acid; and salts formed with organic acids, such as, for example, formic acid, acetic acid, oxalic acid, tartaric acid, succinic acid, malic acid, malonic acid, ascorbic acid, citric acid, benzoic acid, tannic acid, palmoic acid, alginic acid, polyglutamic acid, tosic acid, methanesulfonic acid, naphthalenesulfonic acid, naphthalenedisulfonic acid, α-ketoglutaric acid, β-glycerophosphoric acid and polygalacturonic acid. Suitable salts include those derived from alkali metals such as lithium, potassium and sodium, from alkaline earth metals such as calcium and magnesium, as well as from other acids well known to those of skill in the pharmaceutical art. Other suitable salts include those derived from metal cations such as zinc, bismuth, barium, or aluminum, or with a cation formed from an amine, such as ammonia, N,N-dibenzylethylenediamine, D-glucosamine, tetraethylammonium, or ethylenediamine. Moreover, suitable salts include those derived from a combination of acids and bases, such as, for example, a zinc tannate salt.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The terms "administered", "administration", "administering" a compound will be understood to mean providing any compound of the methods of the invention to an individual in need of treatment.

The term "in vitro" refers to a biological entity, a biological process or a biological reaction happening outside the body in artificial conditions. For example a cell grown in vitro is to be understood as a cell grown in an environment outside the body, e.g. in a test tube or a microtiter plate.

The term "effective amount" means the amount of the subject compound that will elicit the biological, physiological, pharmacological, therapeutic or medical response of a cell, tissue, system, body, animal, individual, patient or human that is being sought by the researcher, scientist, pharmacologist, pharmacist, veterinarian, medical doctor, or other clinician, e.g., lessening of the effects/symptoms of a disorder, such as a proliferative disorder, like e.g. cancer or tumor, or killing or inhibiting growth of a proliferating cell, such as a tumor cell.

The term "further treated", "further administer" or "further administered", means that the different therapeutic agents may be administered together, alternatively or intermittently. Such further administration may be temporally or spatially separated, for example at different times, on different days or via different modes or routes of administration.

Compounds of the Present Invention

The present invention provides compounds of general formula (I):

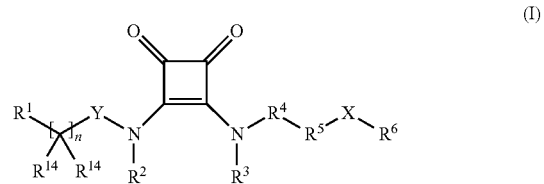

wherein:
n is 0 to 4;
Y is absent, —O—, —NR$^{14}$—, —S(=O)$_2$—, or
R$^1$ is a monocyclic or fused or non-fused polycyclic aryl or heteroaryl group, which is substituted by p substituents R$^7$ (where p is an integer from 0 to 10),
and additionally, a substituent of R$^1$ may together with R$^2$ form a linker selected from the group consisting of C$_1$-C$_5$ alkylene and C$_2$-C$_5$ alkenylene;
R$^2$, R$^3$ are each independently hydrogen or alkyl, aryl, aralkyl, each of these groups may be optionally substituted by m substituents R$^8$ (where m is an integer from 0 to 5),
or R$^2$ and R$^3$ together with the N—C=C—N group may form a ring system having 5 to 15 atoms in the ring, selected from the group consisting of carbon and (in addition to the two nitrogen atoms carrying R$^2$ and R$^3$) 0-3 atoms selected from the group consisting of nitrogen, oxygen, and sulfur, and wherein the ring system is substituted by m substituents $R^8$ (where m is an integer from 0 to 5);

or $R^2$ and $R^3$ may each independently represent a structure selected from the group consisting of:

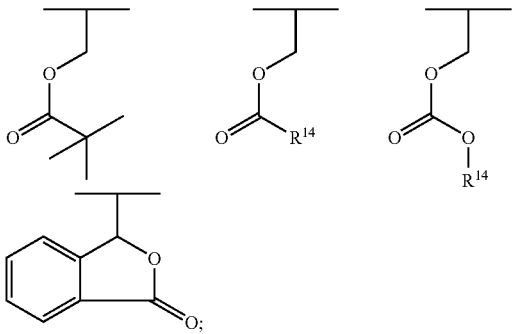

$R^4$ is selected from the group consisting of —$CH_2$—, —O—, —$SO_2$—, —C(=O)— and —NH—;

$R^5$ is a linker moiety selected from the group consisting of $C_2$-$C_{10}$ alkylene, $C_2$-$C_{10}$ alkenylene, $C_2$-$C_{10}$ alkynylene, —[$C_0$-$C_5$ alkylene/$C_2$-$C_5$ alkenylene/$C_2$-$C_5$ alkynylene-(carbocycle)-$C_0$-$C_5$ alkylene/$C_2$-$C_5$ alkenylene/$C_2$-$C_5$ alkynylene]-, —[$C_0$-$C_5$ alkylene/$C_2$-$C_5$ alkenylene/$C_2$-$C_5$ alkynylene-(heterocycle)-$C_0$-$C_5$ alkylene/$C_2$-$C_5$ alkenylene/$C_2$-$C_5$ alkynylene]-, which linker moiety is substituted by k substituents $R^9$ (where k is an integer from 0 to 10);

X is a group A-B-C, wherein
A is a absent or —O—, —$NR^{14}$—, —S—;
B is a absent or —C(=O)—, —S(=O)—, —S(=O)$_2$—, —C(=N—CN)—, —C(=N—$NO_2$)—;
C is a absent or —O—, —$NR^{14}$—, —S—;

$R^6$ is a carbon atom or a saturated or unsaturated carbocycle or heterocycle, each substituted by hydrogen and/or q substituents $R^{10}$ (where q is an integer from 0 to 10);

each $R^7$, $R^8$, $R^9$, $R^{10}$ is independently selected from the group consisting of alkyl, alkenyl, alkynyl, alkoxy, aryl, aralkyl, cycloalkyl, cycloalkylalkyl, haloalkyl, haloalkenyl, haloalkynyl, heterocyclyl, heterocyclylalkyl, halo, nitro, cyano, hydroxy, amino, carboxy, —$OR^{11}$, —$NHR^{11}$, —$NR^{11}R^{12}$, —C(O)H, —C(O)$R^{11}$, —OC(O)$R^{11}$, —C(O)O$R^{11}$, —C(O)NH$R^{11}$, —C(O)N$R^{11}R^{12}$, —S(O)$_x$$R^{11}$ (where X is 0 to 2), —S(O)$_2$O$R^{11}$, —$R^{13}$-nitro, —$R^{13}$-cyano, —$R^{13}$-hydroxy, —$R^{13}$-amino, —$R^{13}$-carboxy, —$R^{13}$—O$R^{11}$, —$R^{13}$—NH$R^{11}$, —$R^{13}$—N$R^{11}R^{12}$, —$R^{13}$—C(O)H, —$R^{13}$—C(O)$R^{11}$, —$R^{13}$—OC(O)$R^{11}$, —$R^{13}$—C(O)O$R^{11}$, —$R^{13}$—C(O)NH$R^{11}$, —$R^{13}$—C(O)N$R^{11}R^{12}$, —$R^{13}$—S(O)$_x$$R^{11}$ (where X is 0 to 2), —$R^{13}$—S(O)$_2$O$R^{11}$; —O—$R^{13}$-nitro, —O—$R^{13}$-cyano, —O—$R^{13}$-hydroxy, —O—$R^{13}$-amino, —O—$R^{13}$-carboxy, —O—$R^{13}$—O$R^{11}$, —O—$R^{13}$—NH$R^{11}$, —O—$R^{13}$—N$R^{11}R^{12}$, —O—$R^{13}$—C(O)H, —O—$R^{13}$—C(O)$R^{11}$, —O—$R^{13}$—OC(O)$R^{11}$, —O—$R^{13}$—C(O)O$R^{11}$, —O—$R^{13}$—C(O)NH$R^{11}$, —O—$R^{13}$—C(O)N$R^{11}R^{12}$, —O—$R^{13}$—S(O)$_x$$R^{11}$ (where X is 0 to 2), —O—$R^{13}$—S(O)$_2$O$R^{11}$; —N($R^{14}$)—$R^{13}$-nitro, —N($R^{14}$)—$R^{13}$-cyano, —N($R^{14}$)—$R^{13}$-hydroxy, —N($R^{14}$)—$R^{13}$-amino, —N($R^{14}$)—$R^{13}$-carboxy, —N($R^{14}$)—$R^{13}$—O$R^{11}$, —N($R^{14}$)—$R^{13}$—NH$R^{11}$, —N($R^{14}$)—$R^{13}$—N$R^{11}R^{12}$, —N($R^{14}$)—$R^{13}$—C(O)H, —N($R^{14}$)—$R^{13}$—C(O)$R^{11}$, —N($R^{14}$)—$R^{13}$—OC(O)$R^{11}$, —N($R^{14}$)C(O)$R^{11}$—, —O—$R^{13}$—N($R^{14}$)—C(O)$R^{11}$—, —N($R^{14}$)—$R^{13}$—C(O)O$R^{11}$, —N($R^{14}$)—$R^{13}$—C(O)NH$R^{11}$, —N($R^{14}$)—$R^{13}$—C(O)N$R^{11}R^{12}$, —N($R^{14}$)—$R^{13}$—S(O)$_x$$R^{11}$ (where X is 0 to 2), —N($R^{14}$)—$R^{13}$—S(O)$_2$O$R^{11}$;

$R^{11}$, $R^{12}$ are each independently selected from the group consisting of alkyl, alkenyl, alkynyl, aryl, aralkyl, cycloalkyl, cycloalkylalkyl, haloalkyl, haloalkenyl, haloalkynyl, heterocyclyl, heterocyclylalkyl, or if $R^{11}$ and $R^{12}$ are both bound to a nitrogen atom, together with the nitrogen atom form a 5-7 membered ring consisting of carbon and 0-2 additional heteroatoms selected from the group consisting of O, S and N (where the N is bound to a further substituent selected from the group consisting of hydrogen, alkyl, aryl, and aralkyl), which ring system may be partially unsaturated;

each $R^{13}$ is independently selected from the group consisting of $C_1$-$C_6$ alkylene, $C_2$-$C_6$ alkenylene, $C_2$-$C_6$ alkynylene;

each $R^{14}$ is independently selected from the group consisting of hydrogen, alkyl, alkenyl, alkynyl, aryl, aralkyl, cycloalkyl, cycloalkylalkyl, haloalkyl, haloalkenyl, haloalkynyl, heterocyclyl, heterocyclylalkyl;

or tautomers or isomers thereof;

as a single stereoisomer or a mixture of stereoisomers;

or as a pharmaceutically acceptable or non-pharmaceutical acceptable salt thereof.

n is an integer from 0 to 4. In other embodiments of the invention, if $R^1$ is a fused or non-fused polycyclic aryl or heteroaryl group, then n may be 5, greater than 5, 7, greater than 7, 9, greater than 9, 11, or greater than 11.

$R^1$ is a monocyclic or fused or non-fused polycyclic aryl or heteroaryl group, which is substituted by p substituents $R^7$ (where p is an integer from 0 to 10). Aryl and heteroaryl groups are know to the skilled artisan and furthermore defined herein. Aryl and/or heteroaryl residues may be substituted with p substituents $R^7$, where p is an integer from 0 to 10. Furthermore aryl and/or heteroaryl residues may also be substituted with additional aryl and/or heteroaryl residues. Those additional aryl and/or heteroaryl residues may be substituted themselves. If $R^1$ is an aryl group, fused or non-fused, this $R^1$ group may be substituted with either an aryl or an heteroaryl group. Likewise, if $R^1$ is an heteroaryl group (fused or non-fused), this $R^1$ group may be substituted with either an heteroaryl or an aryl group. If $R^1$ is a fused polycyclic ring system each individual ring may be homoaryl or heteroaryl.

Additionally, a substituent of $R^1$ may together with $R^2$ form a linker selected from the group consisting of $C_1$-$C_5$ alkylene and $C_2$-$C_5$ alkenylene.

Y is absent, —O—, —$NR^{14}$—, —S(=O)$_2$— or —C(=O)—. In some aspects of the invention n is zero and Y is absent.

$R^2$ and $R^3$ are each independently hydrogen or alkyl, such as methyl or other alkyl residues as defined herein, aryl, aralkyl, each of these groups may be optionally substituted by m substituents $R^8$ (where m is an integer from 0 to 5), or $R^2$ and $R^3$ together with the N—C=C—N group may form a ring system having 5 to 15 atoms in the ring, selected from the group consisting of carbon and (in addition to the two nitrogen atoms carrying $R^2$ and $R^3$) 0-3 atoms selected from the group consisting of nitrogen, oxygen, and sulfur, and wherein the ring system is substituted by m substituents $R^8$ (where m is an integer from 0 to 5). Each of $R^2$ and $R^3$ may also independently represent a structure selected from the group consisting of:

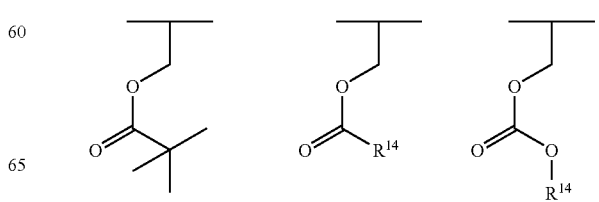

-continued

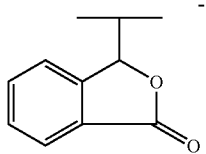

Prodrug forms of the compounds of the present invention are also contemplated within the scope of the present invention. $R^2$ and $R^3$ of the compounds of the present invention may be modified to represent prodrug forms of these compounds. Such prodrugs forms may be converted into a pharmacologically active parent drug in vivo.

$R^4$ is selected from the group consisting of —$CH_2$—, —O—, —$SO_2$—, —C(=O)— and —NH—. $R^4$ may also represent any atom that is not substituted. $R^4$ may also represent any atom that is substituted with hydrogen residues only. $R^4$ may also represent any atom that is substituted with keto/oxo residues only. $R^4$ may also represent any atom that is unsubstituted. $R^4$ may also represent any atom that is unsubstituted but carries one or more free electron pairs.

$R^5$ is a linker moiety selected from the group consisting of $C_2$-$C_{10}$ alkylene, $C_2$-$C_{10}$ alkenylene, $C_2$-$C_{10}$ alkynylene, —[$C_0$-$C_5$ alkylene/$C_2$-$C_5$ alkenylene/$C_2$-$C_5$ alkynylene-(carbocycle)-$C_0$-$C_5$ alkylene/$C_0$-$C_5$ alkenylene/$C_2$-$C_5$ alkynylene]-, —[$C_0$-$C_5$ alkylene/$C_2$-$C_5$ alkenylene/$C_2$-$C_5$ alkynylene-(heterocycle)-$C_0$-$C_5$ alkylene/$C_2$-$C_5$ alkenylene/$C_2$-$C_5$ alkynylene]-, which linker moiety is substituted by k substituents $R^9$ (where k is an integer from 0 to 10). The carbocycle in the $R^5$ linker may be a homoaryl. The homoaryl moiety may be a phenyl. If $R^5$ comprises a ring system, said ring system may be linked to the other parts of the compound in any possible way. For example, if the ring system in $R^5$ comprises a six membered ring, the elements attached to said six membered ring may be attached in the ortho, in the meta or in the para position. It will be obvious to the skilled artisan that similar options of attaching substituents to ring systems other than six membered ring systems exist, all of which are incorporated herein.

The term "$C_0$-$C_5$ alkylene/$C_2$-$C_5$ alkenylene/$C_2$-$C_5$ alkynylene" indicates a residue which may be selected from any one of the group consisting of $C_0$-$C_5$ alkylene, $C_2$-$C_5$ alkenylene and $C_2$-$C_5$ alkynylene. In an embodiment where the alkylene group in a $R^5$ substituent is a $C_0$ alkylene, the substituents $R^4$ and/or $R^6$ may be directly linked to the cyclic moiety of $R^5$.

X is a group A-B-C, wherein
A is absent, —O—, —$NR^{14}$— or —S—;
B is absent, —C(=O)—, —S(=O)—, S(=O)$_2$—, —C(=N—CN)— or —C(=N—$NO_2$)—; and
C is absent, —O—, —$NR^{14}$— or —S—.

In some aspects of the invention B and/or C are absent. In some aspects of the invention A is —O—, —$NR^{14}$— or —S—. In some aspects of the invention A is —NH—. In other aspects of the invention A is absent.

If B and C are absent, A can be absent or selected from the group consisting of —O—, —S— and —NH—. Therefore, if B and C are absent, X is absent or selected from the group consisting of —O—, —S— and —NH—.

$R^6$ is a carbon atom or a saturated or unsaturated carbocycle or heterocycle, each substituted by hydrogen or q substituents $R^{10}$, where q is an integer from 0 to 10. $R^6$ may also be a fused saturated or unsaturated carbocycle or heterocycle, each substituted by hydrogen and/or q substituents $R^{10}$, where q is an integer from 0 to 10. Depending on the size of the fused ring system, said fused saturated or unsaturated carbocycle or heterocycle may also be substituted with more than 10 substituents $R^{10}$.

If $R^6$ is a saturated or unsaturated carbocycle or heterocycle, said saturated or unsaturated carbocycle or heterocycle may also be substituted with additional saturated or unsaturated carbocycles, heterocycles, or fused saturated or unsaturated carbocycle or heterocycle. Those additional saturated or unsaturated carbocycles, heterocycles, or fused saturated or unsaturated carbocycle or heterocycle may be substituted themselves accordingly.

Likewise, if $R^6$ is a fused saturated or unsaturated carbocycle or heterocycle, said fused saturated or unsaturated carbocycle or heterocycle may also be substituted with additional saturated or unsaturated carbocycles, heterocycles, or fused saturated or unsaturated carbocycle or heterocycle. Those additional saturated or unsaturated carbocycles, heterocycles, or fused saturated or unsaturated carbocycle or heterocycle may be substituted themselves.

In some aspects of the invention $R^6$ is phenyl. In other aspects of the invention $R^6$ is hydroxyphenyl. In yet other aspects of the invention $R^6$ is phenyl or hydroxyphenyl, wherein said phenyl or hydroxyphenyl is substituted. In yet other aspects of the invention $R^6$ is 2-pyridyl, 3-pyridyl or 4-pyridyl.

$R^6$ may be substituted by hydrogen and/or q substituents $R^{10}$, where q is an integer from 0 to 10. In particular embodiments $R^6$ is substituted with 0-5 substituents $R^{10}$. $R^{10}$ is independently selected from the group consisting of alkyl, alkenyl, alkynyl, alkoxy, aryl, aralkyl, cycloalkyl, cycloalkylalkyl, haloalkyl, haloalkenyl, haloalkynyl, heterocyclyl, heterocyclylalkyl, halo, nitro, cyano, hydroxy, amino, carboxy, —$OR^{11}$, —$NHR^{11}$, —$NR^{11}R^{12}$, —C(O)H, —C(O)$R^{11}$, —OC(O)$R^{11}$, —C(O)O$R^{11}$, —C(O)NH$R^{11}$, —C(O)N$R^{11}R^{12}$, —S(O)$_x$$R^{11}$ (where X is 0 to 2), —S(O)$_2$O$R^{11}$, —$R^{13}$-nitro, —$R^{13}$-cyano, —$R^{13}$-hydroxy, —$R^{13}$-amino, —$R^{13}$-carboxy, —$R^{13}$—O$R^{11}$, —$R^{13}$—NH$R^{11}$, —$R^{13}$—N$R^{11}R^{12}$, —$R^{13}$—C(O)H, —$R^{13}$—C(O)$R^{11}$, —$R^{13}$—OC(O)$R^{11}$, —$R^{13}$—C(O)O$R^{11}$, —$R^{13}$—C(O)NH$R^{11}$, —$R^{13}$—C(O)N$R^{11}R^{12}$, —$R^{13}$—S(O)$_x$$R^{11}$ (where X is 0 to 2), —$R^{13}$—S(O)$_2$O$R^{11}$; —O—$R^{13}$-nitro, —O—$R^{13}$-cyano, —O—$R^{13}$-hydroxy, —O—$R^{13}$-amino, —O—$R^{13}$-carboxy, —O—$R^{13}$—O$R^{11}$, —O—$R^{13}$—NH$R^{11}$, —O—$R^{13}$—N$R^{11}R^{12}$, —O—$R^{13}$—C(O)H, —O—$R^{13}$—C(O)$R^{11}$, —O—$R^{13}$—OC(O)$R^{11}$, —O—$R^{13}$—C(O)O$R^{11}$, —O—$R^{13}$—C(O)NH$R^{11}$, —O—$R^{13}$—C(O)N$R^{11}R^{12}$, —O—$R^{13}$—S(O)$_x$$R^{11}$ (where X is 0 to 2), —O—$R^{13}$—S(O)$_2$O$R^{11}$; —N($R^{14}$)—$R^{13}$-nitro, —N($R^{14}$)—$R^{13}$-cyano, —N($R^{14}$)—$R^{13}$-hydroxy, —N($R^{14}$)—$R^{13}$-amino, —N($R^{14}$)—$R^{13}$-carboxy, —N($R^{14}$)—$R^{13}$—O$R^{11}$, —N($R^{14}$)—$R^{13}$—NH$R^{11}$, —N($R^{14}$)—$R^{13}$—N$R^{11}R^{12}$, —N($R^{14}$)—$R^{13}$—C(O)H, —N($R^{14}$)—$R^{13}$—C(O)$R^{11}$, —N($R^{14}$)—$R^{13}$—OC(O)$R^{11}$, —N($R^{14}$)C(O)$R^{11}$—, —O—$R^{13}$—N($R^{14}$)—C(O)$R^{11}$—, —N($R^{14}$)—$R^{13}$—C(O)O$R^{11}$, —N($R^{14}$)—$R^{13}$—C(O)NH$R^{11}$, —N($R^{14}$)—$R^{13}$—C(O)N$R^{11}R^{12}$, —N($R^{14}$)—$R^{13}$—S(O)$_x$$R^{11}$ (where X is 0 to 2), —N($R^{14}$)—$R^{13}$—S(O)$_2$O$R^{11}$.

In some aspects of the invention $R^{10}$ is selected from the group consisting of halogen, alkylhalogen, $C_1$-$C_6$ alkyl, $C_1$-$C_6$ alkoxy, —CN, (morpholin-4-yl)$C_1$-$C_6$ alkyl or (morpholin-4-yl)$C_1$-$C_6$ alkoxy.

In some aspects of the invention n is zero and Y is absent. Therefore, in some aspect of the invention compounds of the subject invention may be defined by the following formula (formula (Ia)) with the definitions of $R^1$, $R^2$, $R^3$, $R^4$, $R^5$, X and $R^6$ given above:

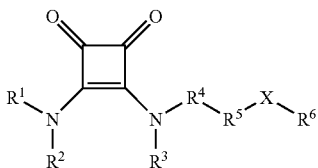

(Ia)

In some aspect of the present invention the compound is selected from the group of 3-[6-(4-Chloro-phenoxy)-hexylamino]-4-(pyridin-4-ylamino)-cyclobut-3-ene-1,2-dione,
3-[6-(4-Chloro-phenoxy)-hexylamino]-4-(pyridin-3-ylamino)-cyclobut-3-ene-1,2-dione,
3-[5-(4-Chloro-phenoxy)-pentylamino]-4-(pyridin-4-ylamino)-cyclobut-3-ene-1,2-dione,
3-[8-(4-Chloro-phenoxy)-octylamino]-4-(pyridin-4-ylamino)-cyclobut-3-ene-1,2-dione,
3-[4-(4-Chloro-phenoxy)-butylamino]-4-(pyridin-4-ylamino)-cyclobut-3-ene-1,2-dione,
3-[7-(4-Chloro-phenoxy)-heptylamino]-4-(pyridin-4-ylamino)-cyclobut-3-ene-1,2-dione,
3-(7-Phenoxy-heptylamino)-4-(pyridin-4-ylamino)-cyclobut-3-ene-1,2-dione,
3-[5-(4-Chloro-phenoxy)-pentylamino]-4-(pyridin-3-ylamino)-cyclobut-3-ene-1,2-dione,
3-(6-Phenoxy-hexylamino)-4-(pyridin-4-ylamino)-cyclobut-3-ene-1,2-dione,
3-(Pyridin-4-ylamino)-4-(6-p-tolyloxy-hexylamino)-cyclobut-3-ene-1,2-dione,
3-[6-(4-Methoxy-phenoxy)-hexylamino]-4-(pyridin-4-ylamino)-cyclobut-3-ene-1,2-dione,
3-[6-(3,4-Dichloro-phenoxy)-hexylamino]-4-(pyridin-4-ylamino)-cyclobut-3-ene-1,2-dione,
3-(6-Phenoxy-hexylamino)-4-(pyridin-3-ylamino)-cyclobut-3-ene-1,2-dione,
3-(Pyridin-3-ylamino)-4-(6-p-tolyloxy-hexylamino)-cyclobut-3-ene-1,2-dione,
3-[6-(4-Chloro-phenylsulfanyl)-hexylamino]-4-(pyridin-4-ylamino)-cyclobut-3-ene-1,2-dione,
3-{6-[4-(2-Morpholin-4-yl-ethoxy)-phenoxy]-hexylamino}-4-(pyridin-3-ylamino)-cyclobut-3-ene-1,2-dione,
3-[6-(4-Chloro-phenylamino)-hexylamino]-4-(pyridin-3-ylamino)-cyclobut-3-ene-1,2-dione,
3-[6-(4-Chloro-phenylamino)-hexylamino]-4-(pyridin-4-ylamino)-cyclobut-3-ene-1,2-dione,
3-{6-[4-(2-Morpholin-4-yl-ethoxy)-phenoxy]-hexylamino}-4-(pyridin-4-ylamino)-cyclobut-3-ene-1,2-dione,
3-(Pyridin-4-ylamino)-4-[6-(4-trifluoromethyl-phenoxy)-hexylamino]-cyclobut-3-ene-1,2-dione,
3-(7-Phenyl-heptylamino)-4-(pyridin-4-ylamino)-cyclobut-3-ene-1,2-dione,
3-[6-(4-Morpholin-4-ylmethyl-phenoxy)-hexylamino]-4-(pyridin-3-ylamino)-cyclobut-3-ene-1,2-dione,
3-(Pyridin-4-ylamino)-4-[6-(pyridin-3-yloxy)-hexylamino]-cyclobut-3-ene-1,2-dione
3-[4-(4-Chloro-phenoxy)-benzylamino]-4-(pyridin-3-ylamino)-cyclobut-3-ene-1,2-dione,
3-[4-(4-Chloro-phenoxymethyl)-benzylamino]-4-(pyridin-3-ylamino)-cyclobut-3-ene-1,2-dione,
3-[3-(4-Chloro-phenoxy)-benzylamino]-4-(pyridin-3-ylamino)-cyclobut-3-ene-1,2-dione,
3-[(Biphenyl-4-ylmethyl)-amino]-4-(pyridin-3-ylamino)-cyclobut-3-ene-1,2-dione,
3-[4-(4-Chloro-phenoxy)-benzylamino]-4-(pyridin-2-ylamino)-cyclobut-3-ene-1,2-dione,
3-(4-Phenoxy-benzylamino)-4-(pyridin-3-ylamino)-cyclobut-3-ene-1,2-dione,
3-[3-(4-Chloro-phenoxymethyl)-benzylamino]-4-(pyridin-3-ylamino)-cyclobut-3-ene-1,2-dione,
3-{2-[4-(4-Chloro-phenoxy)-phenyl]-ethylamino}-4-(pyridin-4-ylamino)-cyclobut-3-ene-1,2-dione,
3-{2-[4-(4-Chloro-phenoxy)-phenyl]-ethylamino}-4-(pyridin-3-ylamino)-cyclobut-3-ene-1,2-dione,
3-[2-(4-Phenoxy-phenyl)-ethylamino]-4-(pyridin-4-ylamino)-cyclobut-3-ene-1,2-dione,
3-[2-(4-Phenoxy-phenyl)-ethylamino]-4-(pyridin-3-ylamino)-cyclobut-3-ene-1,2-dione,
3-[2-(1-Benzyl-piperidin-4-yl)-ethylamino]-4-(pyridin-3-ylamino)-cyclobut-3-ene-1,2-dione, and
3-[2-(1-Benzyl-piperidin-4-yl)-ethylamino]-4-(pyridin-4-ylamino)-cyclobut-3-ene-1,2-dione.

In some aspects of the present invention $R^1$ is 3-pyridyl or 4-pyridyl.

In some aspects of the present invention $R^2$ and $R^3$ are both hydrogen. In other aspects of the invention $R^2$ is hydrogen. In other aspects of the invention $R^2$ is hydrogen and $R^3$ is methyl.

In some aspects of the present invention $R^4$ is —$CH_2$—. In other aspects of the present invention $R^4$ is selected from the group consisting of —$CH_2$—, —O—, —$SO_2$—, —C(=O)— and —NH—.

In some aspects of the present invention $R^5$ is $C_2$-$C_{10}$ alkylene, which may be substituted by k substituents $R^9$ (where k is an integer from 0 to 10). In other aspects of the present invention $R^5$ is —[$C_0$-$C_5$ alkylene-(carbocycle)-$C_0$-$C_5$ alkylene]-, which may be substituted by k substituents $R^9$ (where k is an integer from 0 to 10). In yet other aspects of the present invention $R^5$ is —[$C_0$-$C_5$ alkylene-(heterocycle)-$C_0$-$C_5$ alkylene]-, which may be substituted by k substituents $R^9$ (where k is an integer from 0 to 10). In yet other aspects of the present invention $R^5$ is selected from the group consisting of $C_2$-$C_{10}$ alkylene, $C_2$-$C_{10}$ alkenylene, $C_2$-$C_{10}$ alkynylene, —[$C_0$-$C_5$ alkylene/$C_2$-$C_5$ alkenylene/$C_2$-$C_5$ alkynylene-(carbocycle)-$C_0$-$C_5$ alkylene/$C_2$-$C_5$ alkenylene/$C_2$-$C_5$ alkynylene]- and —[$C_0$-$C_5$ alkylene/$C_2$-$C_5$ alkenylene/$C_2$-$C_5$ alkynylene-(heterocycle)-$C_0$-$C_5$ alkylene/$C_2$-$C_5$ alkenylene/$C_2$-$C_5$ alkynylene]-, which linker moiety is substituted by k substituents $R^9$ (where k is an integer from 0 to 10).

In some aspects of the present invention X is —O—. In other aspects of the present invention X is absent. In yet other aspects of the present invention X is —S—. In yet other aspects of the present invention X is —NH—. In yet other aspects of the present invention X is absent or selected from the group consisting of —O—, —S— and —NH—.

In some aspects of the present invention $R^6$ is a carbocycle. In other aspects of the present invention $R^6$ is a heterocycle.

In some aspects of the present invention $R^6$ is substituted with halo, alkyl, alkoxy, cyano, (morpholin-4-yl)$C_1$-$C_6$ alkyl or (morpholin-4-yl)$C_1$-$C_6$ alkoxy.

Those skilled in the art will recognize that all specific combinations of the individual possible residues of the variable regions of the compounds as disclosed herein, i.e. $R^1$, $R^2$, $R^3$, $R^4$, $R^5$, X and $R^6$, are within the scope of the invention.

The present invention further provides the compounds as described above for use in therapy.

The present invention further provides the use of a compound as described above for the preparation of a pharmaceutical composition for the treatment of an individual, such as a mammal, having a disease-state selected from the group of proliferative diseases. In certain embodiments, said individual is a human and said proliferative disease is cancer.

Additionally, the present invention provides a method for treating an individual, such as a mammal, having a disease-state selected from the group of proliferative diseases, comprising administering to said individual a pharmaceutically effective amount of a compound of the invention as described above. In certain embodiments, said individual is a human and said proliferative disease is cancer.

In a further aspect, the invention provides methods of treating an individual suffering from a disease, such as a mammal, including a human, comprising the step of exposing said individual to an effective amount of a subject compound. In certain embodiments, the disease is a proliferative disorder or disease, such as a cancer or tumor. In yet another embodiment, cells associated with said proliferative disorder are exposed to the subject compound.

In a further aspect, the invention provides a method of killing or inhibiting the growth of a cell, comprising contacting the cell with a compound of the invention. In one embodiment, the cell is cultured in-vitro, while in an alternative embodiment the cell is present in an individual. In a particular embodiment the cell is a cancer cell, for example a cell from a tumor cell line or a cell included in a tumour.

Particular Embodiments

In a particular embodiment of the invention, the substituents of the compound of formula (I) are selected in the manner that n is zero and Y is absent, resulting in the general formula (Ia):

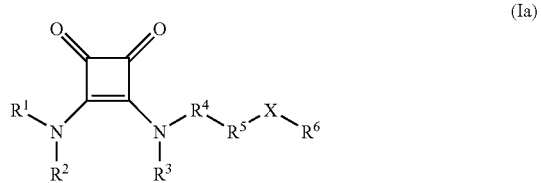

In another preferred embodiment, the substituent $R^5$ is $C_2$-$C_{10}$ alkylene or —[$C_0$-$C_5$ alkylene-(carbocycle)-$C_0$-alkylene]-.

In other particular embodiments —[$C_0$-$C_5$ alkylene-(carbocycle)-$C_0$-$C_5$ alkylene]- is —[$C_0$-$C_5$ alkylene-(phenyl)-$C_0$-$C_5$ alkylene]-. In further particular embodiments —[$C_0$-$C_5$ alkylene-(carbocycle)-$C_0$-$C_5$ alkylene]- is —[$C_0$-$C_5$ alkylene-(aryl)-$C_0$-$C_5$ alkylene]-.

In another particular embodiment the substituent $R^5$ is —[$C_0$-$C_5$ alkylene-(heterocycle)-$C_0$-$C_5$ alkylene]-, wherein said heterocycle may be heteroaryl or a saturated heterocyle as defined herein.

In another particular embodiment, the substituent $R^1$ is 3-pyridyl or 4-pyridyl.

In another particular embodiment, the definitions for A, B and C are selected in a manner that the resulting X is absent or selected from the group consisting of —O—, —S—, —NH—.

In other particular embodiments X is absent or selected from the group consisting of —O—, —S—, —NH—.

In another particular embodiment, the substituent $R^6$ is a carbocycle or a heterocycle substituted with 0-5 substituents $R^{10}$. In other particular embodiments $R^6$ is phenyl or pyridyl. In yet another embodiment $R^{10}$ is independently selected form the group consisting of halogen, alkylhalogen, $C_1$-$C_6$ alkyl, $C_1$-$C_6$ alkoxy, —CN, (morpholin-4-yl)$C_1$-$C_6$ alkyl or (morpholin-4-yl)$C_1$-$C_6$ alkoxy.

In another particular embodiment, the substituents $R^2$ and $R^3$ are each hydrogen. In another preferred embodiment $R^2$ is hydrogen and $R^3$ is alkyl.

In another particular embodiment, the substituent $R^4$ is —$CH_2$—.

In another particular embodiment the compounds is selected from 3-[6-(4-Chloro-phenoxy)-hexylamino]-4-(pyridin-4-ylamino)-cyclobut-3-ene-1,2-dione, 3-{6-[4-(2-Morpholin-4-yl-ethoxy)-phenoxy]-hexylamino}-4-(pyridin-4-ylamino)-cyclobut-3-ene-1,2-dione, 3-(Pyridin-4-ylamino)-4-[6-(pyridin-3-yloxy)-hexylamino]-cyclobut-3-ene-1,2-dione and 3-[6-(4-Morpholin-4-ylmethyl-phenoxy)-hexylamino]-4-(pyridin-3-ylamino)-cyclobut-3-ene-1,2-ione.

Formulations, Dosages and Applications

Formulations

The compositions of this invention can be formulated and administered to treat individuals in need by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the present invention may be formulated in conventional manner using one or more physiologically acceptable carriers or excipients. The pharmaceutical compositions of the invention can be formulated for a variety of routes of administration, including systemic and topical or localized administration. Techniques and formulations generally may be found in Remington's Pharmaceutical Sciences, Meade Publishing Co., Easton, Pa. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments, the pharmaceutical preparations may be non-pyrogenic, i.e., do not elevate the body temperature of a patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of inhibitor which produces a therapeutic effect.

Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

For systemic administration, injection is preferred, including intramuscular, intravenous, intraperitoneal, and subcutaneous (i.m., i.v., i.p., and i.c. respectively). The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol, or Capmul, in a soft gelatin capsule. Antioxidants may be added to prevent long-term degradation as appropriate.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active inhibitor(s) of the present invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

For buccal administration the therapeutic compositions may take the form of tablets or lozenges formulated in a conventional manner.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the therapeutic agents and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more inhibitors of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In addition to the formulations described previously, the pharmaceutical compositions may also be formulated as a depot preparation. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention are formulated into ointments, salves, gels, or creams as generally known in the art. A wash solution can be used locally to treat an injury or inflammation to accelerate healing.

In some cases, in order to prolong the therapeutic effect of an inhibitor, it is desirable to slow the absorption of the inhibitor from subcutaneous or intramuscular injection. This may be accomplished by the use of a liquid suspension of crystalline or amorphous material having poor water solubility. The rate of absorption of the inhibitor then depends upon its rate of dissolution which, in turn, may depend upon crystal size and crystalline form. Alternatively, delayed absorption of a parenterally administered inhibitor form is accomplished by dissolving or suspending the inhibitor in an oil vehicle.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing an inhibitor of the present invention in the proper medium. Absorption enhancers can also be used to increase the flux of the drug across the skin. The rate of such flux can be controlled by either providing a rate controlling membrane or dispersing the compound of the present invention in a polymer matrix or gel.

Ophthalmic formulations, eye ointments, powders, solutions and the like, are also contemplated as being within the scope of this invention.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In other embodiments, the pack or dispenser may be further packaged in an outer carton.

A pharmaceutical composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

Injectable depot forms are made by forming microencapsuled matrices of the subject inhibitors in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to individuals, such as humans and animals, they can be given per se or as a pharmaceutical composition containing, for example, 0.1 to 99.5% (in certain embodiments, 0.5 to 90%) of active ingredient in combination with a pharmaceutically acceptable carrier.

The present invention provides new methods of treating proliferative, degenerative and other disorders or diseases, including cancer, by administering a therapeutically effective amount of at least one of the compounds disclosed herein or an isomeric, prodrug, tautomeric, pharmaceutically acceptable salt, N-oxide or stereoisomeric form thereof. The present invention further provides methods of treating proliferative, degenerative or other disorders or diseases, including cancer, by administering a therapeutically effective combination of at least one of these compounds and another anti-cancer or anti-proliferative agent.

The term "prodrug", as used herein, refers to an agent which is converted into a pharmacologically active parent drug in vivo, such as a compound as defined herein. The term "prodrug" includes any covalently bonded carriers which release an active parent drug of the present invention in vivo when such prodrug is administered to an individual. Since prodrugs are known to enhance numerous desirable qualities of pharmaceuticals (i.e., solubility, bioavailability, manufacturing, transport, pharmacodynamics etc.) the compounds of the present invention may be delivered in prodrug form. Prodrugs, for instance, may be bioavailable by oral administration whereas the parent drug is not. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention. Other examples of prodrugs are compounds of the present invention in which R2 and/or R3 include any one of the following residues:

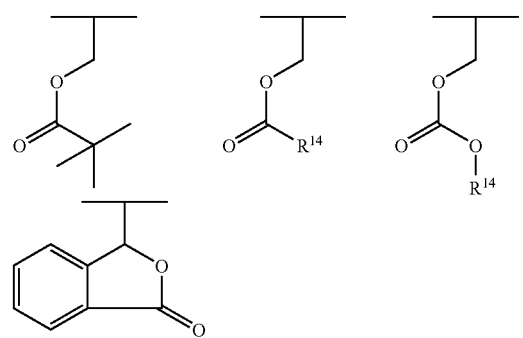

Generally speaking, prodrugs are derivatives of per se drugs, which after administration undergo conversion to the physiologically active species. The conversion may be spontaneous, such as hydrolysis in the physiological environment, or may be enzyme catalyzed. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

From among the voluminous scientific literature devoted to prodrugs in general, the foregoing examples are cited: Gangwar et al., "Prodrug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984) 45-56 (Elsevier); Bundgaard et al. Int. J. of Pharmaceutics 29 (1986) 19-28 (Elsevier); Bundgaard et al. J. Med. Chem. 32 (1989) 2503-2507 Chem. Abstracts 93, 137935y (Bundgaard et al.); Chem. Abstracts 95, 138493f (Bundgaard et al.); Chem. Abstracts 95, 138592n (Bundgaard et al.); Chem. Abstracts 110, 57664p (Alminger et al.); Chem. Abstracts 115, 64029s (Buur et al.); Chem. Abstracts 115, 189582y (Hansen et al.); Chem. Abstracts 117, 14347q (Bundgaard et al.); Chem. Abstracts 117, 55790x (Jensen et al.); and Chem. Abstracts 123, 17593b (Thomsen et al.).

An active compound may be administered as a salt or prodrug that, upon administration to the individual, is capable of providing directly or indirectly the parent compound, such as a compound as defined herein, or that exhibits activity itself. Nonlimiting examples include a pharmaceutically-acceptable salt, alternatively referred to as a "physiologically acceptable salt". In addition, modifications made to a compound can affect its biologic activity, in some cases increasing the activity over the parent compound. This activity can be assessed by preparing a salt or prodrug form of the compound, and testing its activity by using methods described herein or other methods known to those of skill in the art.

As will be apparent to a person skilled in the art, through the use of a prodrug of a given subject compound, an individual treated with such prodrug will be exposed to, and hence indirectly administered with, the subject compound. Such a procedure may expose those cells associated with a disease, such as a proliferative disease or disorder including cancer, to the subject compound.

The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated. All processes used to prepare compounds of the present invention and intermediates made therein are considered to be part of the present invention.

The terms "stereoisomer", "isomer" and "tautomer" as used herein include all possible stereoisomeric, isomeric and tautomeric forms of the compounds of the present invention, as well as their quaternary amine, N-oxide, salt, polymorph, solvate, prodrug and derivative forms. Where the compounds of the present invention contain one or more chiral centers, all possible enantiomeric and diastereomeric forms are included.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include $^{12}C$ and $^{14}C$.

The term "metabolite", as used herein, refers to any substance produced by the metabolism or by a metabolic process. Metabolism, as used herein, refers to the various physical/chemical/biochemical/pharmacological reactions involved in the transformation of molecules or chemical compounds occurring in the cell, tissue, system, body, animal, individual, patient or human therein.

Dosages

The dosage administered will be a therapeutically effective amount of the compound sufficient to result in amelioration of symptoms of, e.g., the cancer or tumor and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The subject compounds may also be administered in prophylactic treatment. If the compound is administered prior to clinical manifestation of the unwanted condition (e.g., disease or other unwanted state of the host animal) then the treatment is prophylactic, (i.e., it protects the individual against initiating, developing or further developing the unwanted condition). The subject compounds may also be administered to prevent a condition, disorder or diseases, such as cancer, or a syndrome complex, such as heart failure or any other medical condition. This includes administration of a compound the intent of which is to reduce the frequency of, or delay the onset of, symptoms of a medical condition in an individual relative to an individual which does not receive the compound. Thus, prevention of cancer includes, for example, reducing the number of detectable cancerous growths, tumors or malignancies in a population of patients receiving a prophylactic treatment relative to an untreated control population, delaying the appearance of detectable cancerous growths in a treated population versus an untreated control population, and/or delaying disease progression and/or improving the quality of patient life, e.g., by a statistically and/or clinically significant amount.

Toxicity and therapeutic efficacy of pharmaceutical compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapeutic agents which exhibit large therapeutic indices are preferred. While therapeutic compositions that exhibit toxic side effects may be used, care should be taken to design a delivery system that targets such therapeutic agents to the site of affected tissue in order to minimize potential damage to uninfected cells and, thereby, reduce side effects.

The data obtained from cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized. For any agents used in the method of the invention, the therapeutically effective dose can be estimated initially from cell culture assays. A dose may be formulated in animal models to achieve a circulating plasma concentration range that includes the IC50 (i.e., the concentration of the test therapeutic agent which achieves a half-maximal inhibition of symptoms or inhibition of biochemical activity) as determined in cell culture. Such information can be used to more accurately determine useful doses in humans. Levels in plasma may be measured, for example, by high performance liquid chromatography.

It is understood that appropriate doses of therapeutic agents depends upon a number of factors known to those or ordinary skill in the art, e.g., a physician. The dose(s) of the subject compounds will vary, for example, depending upon the identity, size, and condition of the subject or sample being treated, further depending upon the route by which the composition is to be administered, if applicable, and the effect which the practitioner desires the therapeutic to have upon the therapeutic target of targets, such as cells, nucleic acid or polypeptides, through with the disease causes, symptoms or effects are mediated.

Exemplary doses include milligram or microgram amounts of the compounds of the present invention per kilogram of subject or sample weight, e.g., about 1 microgram per kilogram to about 500 milligrams per kilogram, about 100 micrograms per kilogram to about 50 milligrams per kilogram, or about 1 milligram per kilogram to about 5 milligrams per kilogram.

A person skilled in the art will appreciate that doses can also be calculated on a body surface basis. A person of 70 kg has an approximate body surface area of 1.8 square meter doses include milligram or microgram amounts of the small molecule per body surface area of subject or sample, e.g. about 50 microgram per square meter to about 15 grams per square meter, about 5 milligrams per square meter to about 1.5 grams per square meter, or about 50 milligram per square meter to about 150 milligrams per square meter.

Applications

The subject compounds are useful to treat various disorders, including proliferative disorders. The term "proliferative disorder" is also art recognized and includes a disorder affecting an individual, such as an animal, in a manner which is marked by aberrant, or otherwise unwanted, proliferation of a subset of cells of an individual. Cancer and tumors are proliferative disorders. Cells comprising or derived from a tumor will generally be understood to be a proliferating cell, typically a hyper-proliferating cell, and in other circumstances, a tumor cell may be dysplastic, or may have proliferated.

It will be apparent to a person skilled in the art, on reading the disclosure of the instant invention, that the methods, pharmaceutical compositions and packaged pharmaceuticals comprising the subject compounds will be useful for the treatment of other proliferative disorders, or for killing or inhibiting proliferating cells including tumor cells.

Compounds of the present invention may be useful in the treatment of disease processes which feature abnormal cellular proliferation, such as hyperproliferative diseases, including cancer, benign prostate hyperplasia, familial adenomatosis polyposis, neurofibromatosis, psoriasis, fungal infections, endotoxic shock, hypertrophic scar formation, inflammatory bowel disease, transplant rejection, vascular smooth muscle cell proliferation associated with atherosclerosis, psoriasis, pulmonary fibrosis, arthritis, glomerulonephritis, restenosis following angioplasty or vascular surgery, and other post-surgical stenosis and restenosis. See, for example, U.S. Pat. Nos. 6,114,365 and 6,107,305.

The compounds disclosed herein are expected to be useful in the therapy of proliferative or hyperproliferative diseases such as cancer, autoimmune diseases, viral diseases, fungal diseases, neurodegenerative disorders and cardiovascular disease.

In certain embodiments, tumors may be solid tumors, which are cancer of body tissues other than blood, bone marrow, or the lymphatic system. In other embodiments tumors may be hematological tumors, such as leukemia and lymphomas. Leukemia is a collective term for malignant diseases characterized by a proliferation of malignantly changed white blood cells. Diseases arising from lymphatic tissue are called lymphomas.

Solid tumors may be selected from: liver cancer, stomach cancer, colon cancer, breast cancer, pancreas cancer, prostate cancer, skin cancer, renal cancer, bone cancer, thyroid cancer, skin cancer, including squamous cell carcinoma, esophagus cancer, kidney cancer, bladder cancer, gall cancer, cervical cancer, ovarian cancer, lung cancer, bronchial, small and non-small-cell lung cancer, gastric, and head and neck cancer.

Hematological tumors may be leukemia, such as Acute Myelogenous Leukemia (AML), Acute Lymphoblastic Leukemia (ALL), Acute Lymphocytic Leukemia, Acute Leukemia, Acute Promyelocytic Leukemia, Chronic Granulocytic Leukemia (CGL), Chronic Leukemia, Chronic Lymphocytic Leukemia (CLL), Chronic Myelogenous Leukemia (CML), Chronic Myelomonocytic Leukemia, Common-type Acute Lymphoblastic Leukemia, Eosinophilic Leukemia, Erythroleukemia, Extranodal Lymphoma, Follicular Lymphoma, Hairy Cell Leukemia, Monocytic Leukemia, Prolymphocytic Leukemia.

Hematological tumors may also be lymphoma, such as B Cell Lymphomas, Burkitt Lymphoma, Cutaneous T Cell Lymphoma, High-Grade Lymphoma, Hodgkin Lymphoma, Non-Hodgkin Lymphoma, Low-grade Lymphoma, Lymphoblastic Lymphoma, Mantle Cell Lymphoma, Marginal Zone Lymphoma, Mucosa-Associated Lymphoid Tissue (MALT) Lymphomas, T Cell Lymphomas, peripheral T cell lymphoma, multiple myeloma, Essential Thrombocythemia, Hairy Cell Lymphoma, Extramedullary myeloma, Granulocytic Sarcomae.

Hematological tumors may also be tumors of myeloid lineage, including acute and chronic myelogenous leukemias, myelodysplastic syndrome, and promyelocytic leukaemia.

Tumors may also be of mesenchymal origin, such as fibrosarcoma and rhabdomyosarcoma. Furthermore, tumors may be tumors of the central and peripheral nervous system, such as astrocytoma, neuroblastoma, glioma, and schwannomas; and tumors may be other tumors, such as melanoma, seminoma, teratocarcinoma, osteosarcoma, xenoderoma pigmentosum, keratoctanthoma, thyroid follicular cancer, and Kaposi's sarcoma.

Tumors that are resistant or refractory to treatment with other anti-cancer or anti-proliferative agents may also benefit from treatment with the methods and pharmaceutical compositions of the present invention.

Compounds disclosed herein may induce or inhibit apoptosis. The apoptotic response is aberrant in a variety of human diseases. Compounds described herein, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds disclosed herein may also be useful in the chemoprevention of cancer. Chemoprevention is defined as inhibiting the development of invasive cancer by either blocking the initiating mutagenic event or by blocking the progression of pre-malignant cells, such as by blocking growth of the tumor, that have already suffered an insult or inhibiting tumor relapse.

Compounds disclosed herein may also be useful in inhibiting tumor angiogenesis and metastasis.

The compounds of this invention may also be useful in combination (administered together or sequentially) with known anti-cancer treatments such as radiation therapy or with anti-cancer, anti-proliferative, cytostatic or cytotoxic agents. Other anti-cancer and anti-proliferative agents which may be used in combination with the compounds of the present invention include those described herein. In combination treatment, the compounds of the present invention may be further administered with any other anti-cancer and anti-proliferative agent disclosed herein.

If formulated as a fixed dose, such combination products employ the compounds of this invention within the dosage range described herein and the other pharmaceutically active agent or treatment within its approved dosage range. For example, the cdc2 inhibitor olomucine has been found to act synergistically with known cytotoxic agents in inducing apoptosis (J. Cell Sci., 108, 2897 (1995)). Compounds described herein may also be administered sequentially with known anti-cancer or anti-proliferative agents when a combination formulation is inappropriate. The invention is not limited in the sequence of administration; compounds described herein may be administered either prior to or after administration of the known anti-cancer or anti-proliferative agent. For example, the cytotoxic activity of the cyclin-dependent kinase inhibitor flavopiridol is affected by the sequence of administration with anticancer agents (Cancer Research, 57, 3375 (1997)).

Further Aspects of the Invention

Another aspect the invention provides a pharmaceutical package, wherein said package includes a compound of any of the compounds of the present invention. In certain other embodiments, the pharmaceutical package includes compounds of the present invention formulated together with another pharmaceutical ingredient. In this case, the compounds of the present invention and the other pharmaceutical ingredient may be formulated separately and in individual dosage amounts.

Other pharmaceutical ingredients that may be formulated together or separately with the compounds of the present invention include but are not limited to other anti-cancer and anti-proliferative agents such as described above. In certain still further embodiments, the pharmaceutical package comprises instructions to treat a patient in need of such treatment. In yet another aspect the invention provides a pharmaceutical package for treating an individual suffering from a proliferative disorder, such as a tumor or a cancer, wherein said package includes at least one compound of the present invention. In certain still further embodiments, the pharmaceutical package comprises instructions to treat the disorder.

As used herein the term "pharmaceutical package" or "pharmaceutical pack" refer to any packaging system for storing and dispensing individual doses of medication. Preferably the pharmaceutical package contains sufficient daily dosage units appropriate to the treatment period or in amounts which facilitate the patient's compliance with the regimen. In certain embodiments, the pharmaceutical pack comprises one or more vessels that include the active ingredient, e.g. a compound of the present invention. Such vessel can be a container such as a bottle, vial, syringe or capsule, or may be a unit dosage form such as a pill. The active ingredient may be provided in the vessel in a pharmaceutically acceptable form or may be provided e.g. as a lyophilized powder. In further embodiments, the pharmaceutical pack may can further include a solvent to prepare the active ingredient for administration. In certain embodiments, the active ingredient may be already provided in a delivery device, such as a syringe, or a suitable delivery device may be included in the pack. The pharmaceutical package may comprise pills, liquids, gels, tablets, dragees or the pharmaceutical preparation in any other suitable form. The package may contain any number of daily pharmaceutical dosage units. The package may be of any shape, and the unit dosage forms may be arranged in any pattern, such as circular, triangular, trapezoid, hexagonal or other patterns. One or more of the doses or subunits may be indicated, for example to aid the doctor, pharmacist or patient, by identifying such dose or subunits, such as by employing color-coding, labels, printing, embossing, scorings or patterns. The pharmaceutical package may also comprise instructions for the patient, the doctor, the pharmacist or any other related person.

Some embodiments comprise the administration of more than one active ingredient, including compounds as disclosed herein. Such administration may occur concurrently or sequentially. The active ingredients may be formulated together such that one administration delivers both components. Alternatively the active ingredients may be formulated separately. The pharmaceutical package may comprise the compound of the present invention and the other pharmaceutical ingredient in a single formulation, i.e. they are formulated together, or the compound of the present invention and the other pharmaceutical ingredient in individual formulations, i.e. they are formulated separately. Each formulation may comprise the compound of the present invention and the other pharmaceutical ingredient in individual dosage amounts (in approximately equal or unequal amounts). Administration of the compound of the present invention and the other pharmaceutical ingredient results in a concentration that results in a therapeutically effective amount of the combination.

As used herein, the term "instructions" means a product label and/or documents describing relevant materials or methodologies pertaining to assembly, preparation or use of a kit or packaged pharmaceutical. These materials may include any combination of the following: background information, steps or procedures to follow, list of components, proposed dosages, warnings regarding possible side effects, instructions for administering the drug, technical support, and any other related documents. Instructions can be supplied in paper form. Alternatively, instruction may also be stored in electronic form, e.g. on a computer-readable storage medium such as a computer-readable memory device, a centralized database, magnetic media such as hard disks, floppy disks, and magnetic tape; optical media such as compact discs, CD-ROMs and holographic devices; magneto-optical media such as floptical disks; and hardware devices that are specially configured to store and execute program code, such as application-specific integrated circuits (ASICs), programmable logic devices (PLDs) and ROM (read only memory) and RAM (random access memory) devices. Instructions may be downloaded from an internet website, or as recorded presentation. Instructions can contain one or multiple documents or future updates.

Synthesis

Some compounds of the invention can be prepared by the synthetic sequence shown in Scheme 1. For example all compounds of examples 1-39 can be synthesized according to Scheme 1. As depicted in Scheme 1, either one of the two amines (Amine-1 or Amine-2) may be linked to the squaric acid diethyl ester first, followed by the second amine. A skilled artisan will appreciate that other routes of synthesis may be employed as well. In particular, other routes of synthesis may in fact be required for certain aspects of the present invention. Other routes of synthesis may be required, e.g. if Y is —C(=O)— or —S(=O)₂—, or if R4 is —C(=O)— or —S(=O)₂—. The skilled artisan is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

SCHEME 1:

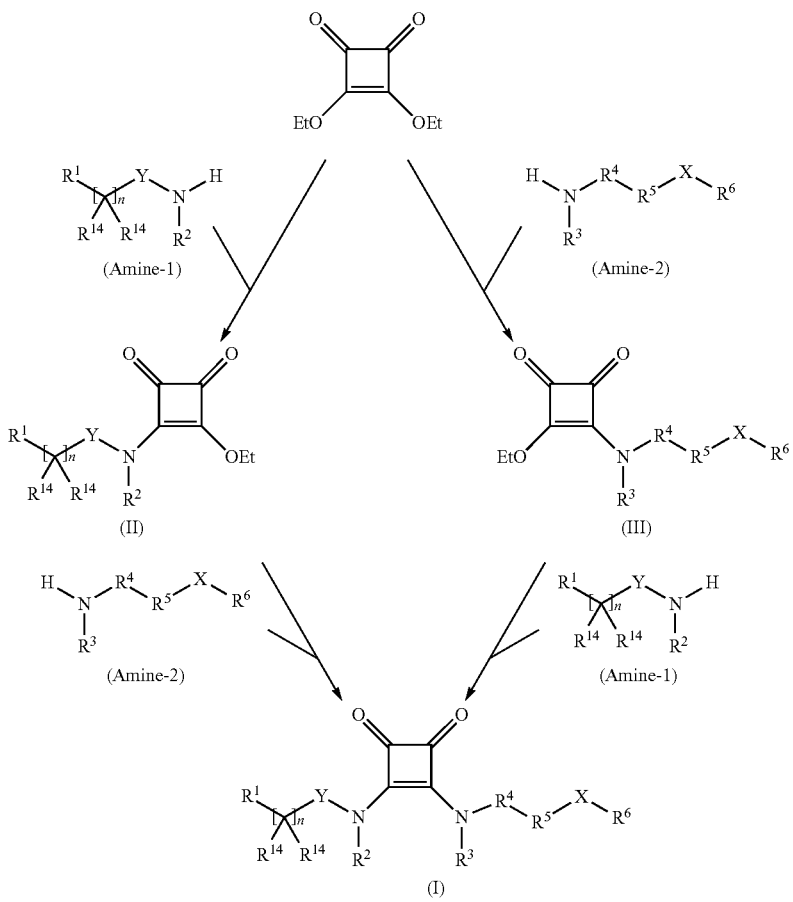

The squaric acid diethyl ester employed in the sequence of scheme 1 is commercially available.

The amine compounds (Amine-1) and (Amine-2) employed in the sequence of scheme 1 are commercially available or can be prepared by methods known to those skilled in the art, such as described in further detail below (examples 40-60).

EXAMPLES

A selection of compounds within the scope of the present invention are listed in Table 4. Such compounds shown in Table 4 were synthesized according to the examples below, and the surprising anti-proliferative activity of these compounds was determined according to examples 61 and 62.

A(I): Synthesis of Squaric Acid Derivatives (examples 1-39).

Example 1

Example 1A

3-Ethoxy-4-(pyridin-3-yl-amino)-3-cyclobutene-1,2-dione

3-Aminopyridine (12.3 g, 130 mmol) was added to a solution of 3,4-diethoxy-3-cyclobutene-1,2-dione (21.5 g; 125 mmol) in 130 mL EtOH. The mixture was heated to reflux for 16 h, filtered and the filtrate was concentrated under reduced pressure. The residue was purified by flash chromatography (7% EtOH in EtOAc) to give the title compound as a yellow powder.

Yield: 13.6 g, 50%

$^1$H-NMR (d6-DMSO): 1.42 (t, J=7.1 Hz, 3H), 4.77 (q, J=7.1 Hz, 2H), 7.39 (dd, J=4.7, 8.3 Hz, 1H), 7.77 (d, J=8.3 Hz, 1H), 8.31 (dd, J=2.6, 4.7 Hz, 1H), 8.59 (d, J=2.6 Hz, 1H), 10.9 (s, 1H).

Example 1B

3-[6-(4-Chlorophenoxy)-hexylamino)]-4-(pyridin-3-yl-amino)-3-cyclobutene-1,2-dione (SQ-1B)

The product from example 1A (368 mg, 1.68 mmol) was dissolved in hot EtOH (6 mL). 6-(4-Chlorophenoxy)-hexylamine (551 mg, 2.42 mmol) was added and the mixture was stirred at r.t. for 18 h. The precipitate was filtered off and washed with cold EtOH (2×2 mL) to give the title compound.

Yield: 534 mg, 79%

$^1$H-NMR (d6-DMSO): 1.40-1.50 (m, 4H), 1.55-1.80 (m, 4H), 3.60-3.70 (m, 2H), 3.90-4.00 (m, 2H), 6.93 (d, J=8.7 Hz, 2H), 7.28 (d, J=8.7 Hz, 2H), 7.35 (dd, J=4.6, 8.0 Hz, 1H), 7.70 (s, br, 1H), 7.90 (m, 1H), 8.22 (m, 1H), 8.55 (s, 1H).

MS: m/z=400 (MH$^+$).

Example 2

3-[5-(4-Chlorophenoxy)-pentylamino)]-4-(pyridin-3-yl-amino)-3-cyclobutene-1,2-dione (SQ-2)

The title compound was prepared according to the procedure described in example 1B starting from 3-ethoxy-4-(pyridin-3-yl-amino)-3-cyclobutene-1,2-dione prepared according to example 1A and 5-(4-chlorophenoxy)-pentylamine.

Yield: 348 mg, 90%.

$^1$H-NMR (d6-DMSO): 1.44-1.52 (m, 2H), 1.59-1.77 (m, 4H), 3.63 (m, 2H), 3.96 (t, J=6.3 Hz, 2H), 6.93 (d, J=8.9 Hz, 2H), 7.27 (d, J=8.9 Hz, 2H), 7.33-7.38 (m, 1H), 7.70 (s, br, 1H), 7.92 (m, 1H), 8.22 (m, 1H), 8.55 (m, 1H), 9.73 (s, br, 1H).

MS: m/z=386 (MH$^+$).

Example 3

3-[6-(4-Phenoxy)-hexylamino)]-4-(pyridin-3-yl-amino)-3-cyclobutene-1,2-dione (SQ-3)

The title compound was prepared according to the procedure described in example 1B starting from 3-ethoxy-4-(pyridin-3-yl-amino)-3-cyclobutene-1,2-dione prepared according to example 1A and 6-(4-phenoxy)-hexylamine.

Yield: 199 mg, 73%.

$^1$H-NMR (d6-DMSO): 1.30-1.55 (m, 4H), 1.57-1.77 (m, 4H), 3.61 (m, 2H), 3.95 (t, J=6.5 Hz, 2H), 6.89-6.92 (m, 3H), 7.23-7.26 (m, 2H), 7.35-7.40 (m, 1H), 7.70 (s, br, 1H), 7.92 (m, 1H), 8.22 (m, 1H), 8.55 (m, 1H), 9.70 (s, br, 1H).

MS: m/z=366 (MH$^+$).

Example 4

3-[6-(4-Methylphenoxy)-hexylamino)]-4-(pyridin-3-yl-amino)-3-cyclobutene-1,2-dione (SQ-4)

The title compound was prepared according to the procedure described in example 1B starting from 3-ethoxy-4-(pyridin-3-yl-amino)-3-cyclobutene-1,2-dione prepared according to example 1A and 6-(4-methylphenoxy)-hexylamine.

Yield: 187 mg, 66%.

$^1$H-NMR (d6-DMSO): 1.35-1.50 (m, 4H), 1.57-1.75 (m, 4H), 2.20 (s, 3H), 3.61 (m, 2H), 3.90 (t, J=6.4 Hz, 2H), 6.79 (d, J=8.4 Hz, 2H), 7.04 (d, J=8.4 Hz, 2H), 7.35-7.40 (m, 1H), 7.70 (s, br, 1H), 7.92 (m, 1H), 8.22 (m, 1H), 8.55 (m, 1H), 9.73 (s, br, 1H).

MS: m/z=380 (MH$^+$).

Example 5

3-[2-(4-Phenoxyphenyl)-ethylamino]-4-(pyridin-3-yl-amino)-cyclobut-3-ene-1,2-dione (SQ-5)

The title compound was prepared according to an analogous procedure to that described in example 1B starting from 3-ethoxy-4-(pyridin-3-yl-amino)-3-cyclobutene-1,2-dione prepared according to example 1A and 2-(4-phenoxyphenyl)-ethylamine. The reaction mixture was heated to reflux for 2 h instead of stirring 18 h at r.t.

Yield: 259 mg, 90%.

$^1$H-NMR (d6-DMSO): 2.89 (t, J=7.0 Hz, 2H), 3.86 (m, 2H), 6.94-6.97 (m, 4H), 7.11 (m, 1H), 7.27-7.38 (m, 5H), 7.71 (s, br, 1H), 7.89 (m, 1H), 8.22 (m, 1H), 8.54 (m, 1H), 9.71 (s, br, 1H).

MS: m/z=380 (MH$^+$).

Example 6

3-{2-[4-(4-Chlorophenoxy)-phenyl]-ethylamino}-4-(pyridin-3-yl-amino)-cyclobut-3-ene-1,2-dione (SQ-6)

3-Ethoxy-4-(pyridine-3-ylamino)-3-cyclobutene-1,2-dione (70 mg, 0.32 mmol) prepared according to example 1A and 2-[4-(4-chlorophenoxy)-phenyl]-ethylamine (105 mg, 0.45 mmol) in EtOH (1.5 mL) were stirred and heated to 150° C. in a sealed vessel in a microwave synthesizer for 1 min. After cooling to r.t. the precipitate was filtered off, washed with EtOH (3×3 mL) and dried in vacuo.

Yield: 121 mg, 90%.

$^1$H-NMR (d6-DMSO): 2.82 (m, 2H), 3.79 (m, 2H), 6.90 (m, 4H), 7.22-7.34 (m, 5H), 7.81 (s, br, 1H), 7.83 (m, 1H), 8.16 (m, 1H), 8.46 (m, 1H), 9.70 (s, br, 1H).

MS: m/z=420 (MH$^+$).

Example 7

Example 7A

3-Ethoxy-4-(pyridin-4-yl-amino)-3-cyclobutene-1,2-dione

The title compound was prepared according to the procedure described in example 1A starting from 4-aminopyridine. Eluent for flash chromatography: 5% EtOH in EtOAc.

Yield: 6.24 g, 30%

$^1$H-NMR (d6-DMSO): 1.44 (t, J=7.1 Hz, 3H), 4.80 (q, J=7.1 Hz, 2H), 7.40 (d, J=6.3 Hz, 2H), 8.45 (d, J=6.3 Hz, 2H), 11.00 (s, 1H).

Example 7B

3-[6-(4-Chlorophenoxy)-hexylamino)]-4-(pyridin-4-yl-amino)-3-cyclobutene-1,2-dione (SQ-7B)

The title compound was prepared according to the procedure described in example 1B starting from 3-ethoxy-4-(pyridin-4-yl-amino)-3-cyclobutene-1,2-dione prepared according to example 7A and 6-(4-chlorophenoxy)-hexylamine.

Yield: 308 mg, 85%.

$^1$H-NMR (d6-DMSO): 1.35-1.50 (m, 4H), 1.55-1.69 (m, 2H), 1.70-1.73 (m, 2H), 3.61 (t, J=6.5 Hz, 2H), 3.95 (t, J=6.5 Hz, 2H), 6.93 (d, J=8.9 Hz, 2H), 7.29 (d, J=8.9 Hz, 2H), 7.41 (d, 5.5 Hz, 2H), 8.39 (d, 5.5 Hz, 2H).

MS: m/z=400 (MH$^+$).

Example 8

3-[5-(4-Chlorophenoxy)-pentylamino)]-4-(pyridin-4-yl-amino)-3-cyclobutene-1,2-dione (SQ-8)

The title compound was prepared according to the procedure described in example 1B starting from 3-ethoxy-4-(pyridin-4-yl-amino)-3-cyclobutene-1,2-dione prepared according to example 7A and 5-(4-chlorophenoxy)-pentylamine.

Yield: 256 mg, 66%.

$^1$H-NMR (d6-DMSO): 1.40-1.48 (m, 2H), 1.60-1.65 (m, 2H), 1.71-1.76 (m, 2H), 3.62 (m, 2H), 3.95 (t, J=6.3 Hz, 2H), 6.92 (d, J=8.9 Hz, 2H), 7.29 (d, J=8.9 Hz, 2H), 7.40 (m, 2H), 7.80 (s, 1H), 8.39 (m, 2H), 9.87 (s, 1H).

MS: m/z=386 (MH$^+$).

Example 9

3-[8-(4-Chlorophenoxy)-octylamino)]-4-(pyridin-4-yl-amino)-3-cyclobutene-1,2-dione (SQ-9)

The title compound was prepared according to the procedure described in example 1B starting from 3-ethoxy-4-(pyridin-4-yl-amino)-3-cyclobutene-1,2-dione prepared according to example 7A and 8-(4-chlorophenoxy)-octylamine.

Yield: 308 mg, 72%.

$^1$H-NMR (d6-DMSO): 1.30-1.45 (m, 8H), 1.55-1.65 (m, 2H), 1.68-1.75 (m, 2H), 3.59 (m, 2H), 3.92 (t, J=6.5 Hz, 2H), 6.92 (d, J=8.9 Hz, 2H), 7.27 (d, J=8.9 Hz, 2H), 7.40 (m, 2H), 7.77 (s, br, 1H), 8.38 (m, 2H), 9.70 (s, br, 1H).

MS: m/z=428 (MH$^+$).

Example 10

3-[4-(4-Chlorophenoxy)-butylamino)]-4-(pyridin-4-yl-amino)-3-cyclobutene-1,2-dione (SQ-10)

The title compound was prepared according to the procedure described in example 1B starting from 3-ethoxy-4-(pyridin-4-yl-amino)-3-cyclobutene-1,2-dione prepared according to example 7A and 4-(4-chlorophenoxy)-butylamine.

Yield: 283 mg, 76%.

$^1$H-NMR (d6-DMSO): 1.74-1.76 (m, 4H), 3.60-3.75 (m, 2H), 4.00 (t, J=5.7 Hz, 2H), 6.94 (d, J=8.9 Hz, 2H), 7.31 (d, J=8.9 Hz, 2H), 7.41 (m, 2H), 7.81 (s, br, 1H), 8.40 (m, 2H), 9.86 (s, br, 1H).

MS: m/z=372 (MH$^+$).

Example 11

3-[7-(4-Chlorophenoxy)-heptylamino)]-4-(pyridin-4-yl-amino)-3-cyclobutene-1,2-dione (SQ-11A) and 3-(7-Phenoxyheptylamino)-4-(pyridin-4-yl-amino)-3-cyclobutene-1,2-dione (SQ-11B)

The title compounds were prepared according to the procedure described in example 1B starting from 3-ethoxy-4-(pyridin-4-yl-amino)-3-cyclobutene-1,2-dione prepared according to example 7A and a mixture of 7-(4-chlorophenoxy)-heptylamine and 7-phenoxyheptylamine. The two products were separated by prep HPLC.

3-[7-(4-Chlorophenoxy)-heptylamino)]-4-(pyridin-4-yl-amino)-3-cyclobutene-1,2-dione (SQ-11A)

Yield: 26 mg, 5% after prep HPLC as TFA salt.

$^1$H-NMR (d6-DMSO): 1.30-1.45 (m, 6H), 1.55-1.75 (m, 4H), 3.60-3.70 (m, 2H), 3.94 (t, J=6.2 Hz, 2H), 6.93 (d, J=8.8 Hz, 2H), 7.29 (d, J=8.8 Hz, 2H), 7.83 (m, 2H), 8.60 (m, 3H), 11.45 (s, br, 1H).

MS: m/z=414 (MH$^+$).

3-(7-Phenoxyheptylamino)-4-(pyridin-4-yl-amino)-3-cyclobutene-1,2-dione (SQ-11B)

Yield: 13 mg, 3% after prep HPLC as TFA salt.

$^1$H-NMR (d6-DMSO): 1.30-1.50 (m, 6H), 1.55-1.75 (m, 4H), 3.60-3.70 (m, 2H), 3.94 (t, J=6.3 Hz, 2H), 6.89-6.92 (m, 3H), 7.23-7.29 (m, 2H), 7.76 (m, 2H), 8.34 (m, 1H), 8.57 (m, 2H), 11.10 (s, br, 1H).

MS: m/z=380 (MH$^+$).

Example 12

3-(6-Phenoxyhexylamino)-4-(pyridin-4-yl-amino)-3-cyclobutene-1,2-dione (SQ-12)

The title compound was prepared according to the procedure described in example 1B starting from 3-ethoxy-4-(pyridin-4-yl-amino)-3-cyclobutene-1,2-dione prepared according to example 7A and 6-phenoxyhexylamine.

Yield: 105 mg, 38%.

$^1$H-NMR (d6-DMSO): 1.42-1.72 (m, 8H), 3.60-3.70 (m, 2H), 3.95 (t, J=6.3 Hz, 2H), 6.90 (m, 3H), 7.25 (m, 2H), 7.42 (m, 2H), 7.80 (s, 1H), 8.40 (m, 2H), 9.89 (s, br, 1H).

MS: m/z=366 (MH$^+$).

Example 13

3-[6-(4-Methylphenoxy)-hexylamino]-4-(pyridin-4-yl-amino)-3-cyclobutene-1,2-dione (SQ-13)

The title compound was prepared according to the procedure described in example 1B starting from 3-ethoxy-4-(pyridin-4-yl-amino)-3-cyclobutene-1,2-dione prepared according to example 7A and 6-(4-methylphenoxy)-hexylamine.

Yield: 89 mg, 31%.

$^1$H-NMR (d6-DMSO): 1.40-1.50 (m, 4H), 1.58-1.72 (m, 4H), 2.20 (s, 3H), 3.60-3.65 (m, 2H), 3.90 (t, J=6.3 Hz, 2H), 6.78 (d, J=8.5 Hz, 2H), 7.04 (d, J=8.5 Hz, 2H), 7.42 (d, J=5.8 Hz, 2H), 7.79 (s, br, 1H), 8.40 (d, J=5.8 Hz, 2H), 9.85 (s, br, 1H).

MS: m/z=380 (MH$^+$).

Examples 12 and 13 were treated with additional 0.5 equivalents of the corresponding amine to drive the reactions to completion.

Example 14

3-[6-(4-Methoxyphenoxy)-hexylamino)]-4-(pyridin-4-yl-amino)-3-cyclobutene-1,2-dione (SQ-14)

The title compound was prepared according to the procedure described in example 1B starting from 3-ethoxy-4-(pyridin-4-yl-amino)-3-cyclobutene-1,2-dione prepared according to example 7A and 6-(4-methoxyphenoxy)-hexylamine.

Yield: 194 mg, 65%.

$^1$H-NMR (d6-DMSO): 1.35-1.50 (m, 4H), 1.57-1.72 (m, 4H), 3.60-3.65 (m, 2H), 3.67 (s, 3H), 3.88 (t, J=6.3 Hz, 2H), 6.82 (s, 4H), 7.41 (d, J=5.5 Hz, 2H), 7.80 (s, br, 1H), 8.40 (d, J=5.5 Hz, 2H), 9.90 (s, br, 1H).

MS: m/z=396 (MH$^+$).

Example 15

3-[6-(3,4-Dichlorophenoxy)-hexylamino)]-4-(pyridin-4-yl-amino)-3-cyclobutene-1,2-dione (SQ-15)

The title compound was prepared according to the procedure described in example 1B starting from 3-ethoxy-4-(pyridin-4-yl-amino)-3-cyclobutene-1,2-dione prepared according to example 7A and 6-(3,4-dichlorophenoxy)-hexylamine.

Yield: 244 mg, 75%.

$^1$H-NMR (d6-DMSO): 1.40-1.50 (m, 4H), 1.57-1.74 (m, 4H), 3.58-3.65 (m, 2H), 3.98 (t, J=6.3 Hz, 2H), 6.93 (dd, J=2.9, 8.9 Hz, 1H), 7.20 (d, J=2.9 Hz, 1H), 7.42 (m, 2H), 7.48 (d, J=8.9 Hz, 1H), 7.79 (s, br, 1H), 8.40 (d, J=6.2 Hz, 2H), 9.86 (s, br, 1H).

MS: m/z=396 (MH$^+$).

Example 16

3-(Pyridin-4-ylamino)-4-[6-(pyridin-3-yloxy)-hexylamino]-cyclobut-3-ene-1,2-dione (SQ-16)

The title compound was prepared according to the procedure described in example 1B starting from 3-ethoxy-4-(pyridin-4-yl-amino)-3-cyclobutene-1,2-dione prepared according to example 7A and 6-(pyridin-3-yloxy)-hexylamine.

Yield: 104 mg, 24% after prep. HPLC as bis TFA salt.

$^1$H-NMR (d6-DMSO): 1.35-1.55 (m, 4H), 1.57-1.80 (m, 4H), 3.64 (m, 2H), 4.10 (m, 2H), 7.52 (m, 1H), 7.56 (m, 1H), 7.86 (m, 2H), 8.28 (m, 1H), 8.42 (m, 1H), 8.63 (m, 3H), 11.51 (s, br, 1H).

MS: m/z=367 (MH$^+$).

Example 17

3-[2-(4-Phenoxyphenyl)-ethylamino]-4-(pyridin-4-yl-amino)-cyclobut-3-ene-1,2-dione (SQ-17)

The title compound was prepared according to the procedure described in example 1B starting from 3-ethoxy-4-(pyridin-4-yl-amino)-3-cyclobutene-1,2-dione prepared according to example 7A and 2-(4-phenoxyphenyl)-ethylamine. The reaction mixture was heated to reflux for 2 hours instead of stirring 18 h at r.t.

Yield: 269 mg, 93%.

$^1$H-NMR (d6-DMSO): 2.89 (m, 2H), 3.85 (m, 2H), 6.95 (m, 4H), 7.08 (m, 1H), 7.29-7.36 (m, 6H), 7.78 (s, br, 1H), 8.38 (m, 2H), 9.87 (s, br, 1H).

MS: m/z=386 (MH$^+$).

Example 18

3-[6-(4-Trifluoromethylphenoxy)-hexylamino]-4-(pyridin-4-yl-amino)-cyclobut-3-ene-1,2-dione (SQ-18)

The title compound was prepared according to the procedure described in example 1B starting from 3-ethoxy-4-(pyridin-4-yl-amino)-3-cyclobutene-1,2-dione prepared according to example 7A and 6-(4-trifluoromethylphenoxy)-hexylamine. The reaction mixture was heated to reflux for 4 hours instead of stirring 18 h at r.t.

Yield: 275 mg, 63%.

$^1$H-NMR (d6-DMSO): 1.39-1.50 (m, 4H), 1.58-1.63 (m, 2H) 1.72-1.75 (m, 2H), 3.62 (m, 2H), 4.04 (t, J=6.3 Hz, 2H), 7.09 (d, J=8.7 Hz, 2H), 7.41 (m, 2H), 7.61 (d, J=8.7 Hz, 2H), 7.79 (s, br, 1H), 8.40 (m, 2H), 9.84 (s, br, 1H).

MS: m/z=434 (MH$^+$).

Example 19

4-{6-[3,4-Dioxo-2-(pyridin-4-ylamino)-cyclobut-1-enylamino]-hexyloxy}-benzonitrile (SQ-19)

The title compound was prepared according to the procedure described in example 1B starting from 3-ethoxy-4-(pyridin-4-yl-amino)-3-cyclobutene-1,2-dione prepared according to example 7A and 4-(6-amino]-hexyloxy}-benzonitrile. The reaction mixture was heated to reflux for 2 hours instead of stirring 18 h at r.t.

Yield: 265 mg, 68%.

$^1$H-NMR (d6-DMSO): 1.30-1.50 (m, 4H), 1.55-1.67 (m, 2H) 1.70-1.75 (m, 2H), 3.61 (m, 2H), 4.06 (t, J=6.2 Hz, 2H), 7.08 (d, J=8.7 Hz, 2H), 7.41 (m, 2H), 7.73 (d, J=8.7 Hz, 2H), 7.79 (s, br, 1H), 8.39 (m, 2H), 9.79 (s, br, 1H).

MS: m/z=391 (MH$^+$).

Example 20

3-{2-[4-(4-Chlorophenoxy)-phenyl]-ethylamino}-4-(pyridin-4-yl-amino)-cyclobut-3-ene-1,2-dione (SQ-20)

3-Ethoxy-4-(pyridine-4-yl-amino)-3-cyclobutene-1,2-dione (70 mg, 0.32 mmol) and 2-[4-(4-chlorophenoxy)-phenyl]-ethylamine (105 mg, 0.45 mmol) in EtOH (1.5 mL) were stirred and heated to 150° C. in a sealed vessel in a microwave synthesizer for 30 s. After cooling to r.t. the precipitate was filtered off, washed with EtOH (3×3 mL) and dried in vacuo.

Yield: 118 mg, 89%.

$^1$H-NMR (d6-DMSO): 2.82 (m, 2H), 3.81 (m, 2H), 6.90 (m, 4H), 7.22 (m, 2H), 7.32 (m, 4H), 7.73 (s, br, 1H), 8.33 (m, 2H), 9.83 (s, br, 1H).

MS: m/z=420 (MH$^+$).

Example 21A

3-Ethoxy-4-(pyridin-2-yl-amino)-3-cyclobutene-1,2-dione

2-Aminopyridine (630 mg, 6.7 mmol) was added to a solution of 3,4-diethoxy-3-cyclobutene-1,2-dione (1.0 mL, 6.7 mmol) in EtOH (10 mL). The mixture was heated to reflux for 2.5 h, filtered and the filtrate was concentrated under reduced pressure. The residue was purified by flash chromatography (800 mL hexanes/EtOAc 3:1, 1.5 L hexanes/EtOAc 1:1) to give 431 mg (29%) of the title compound as a yellow powder.

$^1$H-NMR (CDCl$_3$): 1.5 (t, J=7.2 Hz, 3H), 4.88 (q, J=7.2 Hz, 2H), 7.08 (dd, J=3.1, 6.1 Hz, 1H), 7.74-7.79 (m, 2H), 8.41 (dd, J=1.2, 2.5 Hz, 1H), 9.87 (s, 1H).

Example 21B

3-[6-(4-Chloro-phenoxy)-hexylamino]-4-(pyridin-2-ylamino)-cyclobut-3-ene-1,2-dione The title compound was prepared according to the procedure described in example 1B starting from 3-ethoxy-4-(pyridin-2-yl-amino)-3-cyclobutene-1,2-dione and 6-(4-chlorophenoxy)-hexylamine.
Yield: 293 mg 80%.
$^1$H-NMR (d6-DMSO): 1.37-1.40 (m, 4H), 1.41-1.72 (m, 4H), 3.65 (m, 2H), 3.92 (t, J=6.4 Hz, 2H), 6.91 (d, J=9.0 Hz, 2H), 6.98 (m, 1H), 7.21 (d, J=8.4 Hz, 1H), 7.27 (d, J=9.0 Hz, 2H), 7.71-7.77 (m, 1H), 8.30 (d, J=4.0 Hz, 1H), 8.56 (s, br, 1H), 10.28 (s, br, 1H).
MS: m/z=400 (MH$^+$)

Example 22

3-(7-Phenylheptylamino)-4-(pyridin-4-yl-amino)-cyclobut-3-ene-1,2-dione (SQ-22)

The title compound was prepared according to the procedure described in example 1B starting from 3-ethoxy-4-(pyridin-4-yl-amino)-3-cyclobutene-1,2-dione prepared according to example 7A and 7-phenylheptylamine.
Yield: 59%
$^1$H-NMR (d6-DMSO): 1.20-1.65 (m, 10H), 2.55 (t, J=7.6 Hz, 2H), 2.59 (app q, J=6.0 Hz, 2H), 7.12-7.30 (m, 5H), 7.42 (d, J=5.9 Hz, 2H), 7.77 (s, br, 1H), 8.40 (d, J=5.9 Hz, 2H), 9.85 (s, br, 1H).
MS: m/z=364 (MH$^+$)

Example 23

3-[6-(4-(2-Morpholin-4-yl-ethoxy)-phenoxy)-hexylamino]-4-(pyridin-4-yl-amino)-cyclobut-3-ene-1,2-dione (SQ-23)

The title compound was prepared according to the procedure described in example 1B starting from 3-ethoxy-4-(pyridin-4-yl-amino)-3-cyclobutene-1,2-dione prepared according to example 7A and 6-[4-(2-morpholin-4-yl-ethoxy)-phenoxy]-hexylamine.
Yield: 64%
$^1$H-NMR (d6-DMSO): 1.35-1.71 (m, 8H), 2.43-2.47 (m, 4H), 2.64 (t, J=5.9 Hz, 2H), 3.55-3.62 (m, 6H), 3.88 (t, J=6.5 Hz, 2H), 3.98 (t, J=5.8 Hz, 2H), 6.82 (s, 4H), 7.42 (d, J=5.9 Hz, 2H), 7.79 (s, br, 1H), 8.40 (d, J=5.9 Hz, 2H), 9.86 (s, br, 1H).
MS: m/z=495 (MH$^+$)

Example 24

3-[6-(4-(2-Morpholin-4-yl-ethoxy)-phenoxy)-hexylamino]-4-(pyridin-3-yl-amino)-cyclobut-3-ene-1,2-dione (SQ-24)

The title compound was prepared according to the procedure described in example 1B starting from 3-ethoxy-4-(pyridin-3-yl-amino)-3-cyclobutene-1,2-dione prepared according to example 1A and 6-[4-(2-morpholin-4-yl-ethoxy)-phenoxy]-hexylamine.
Yield: 76%
$^1$H-NMR (d6-DMSO): 1.35-1.80 (m, 8H), 2.45-2.51 (m, 4H), 2.66 (t, J=5.7 Hz, 2H), 3.55-3.63 (m, 6H), 3.89 (t, J=6.4 Hz, 2H), 3.99 (t, J=5.8 Hz, 2H), 6.83 (s, 4H), 7.37 (dd, J=4.7, 8.3 Hz, 1H), 7.70 (s, br, 1H), 7.92 (d, br, J=7.2 Hz, 1H), 8.23 (dd, J=1.2, 4.7 Hz, 1H), 8.56 (d, J=2.5 Hz, 1H), 9.86 (s, br, 1H).
MS: m/z=495 (MH$^+$)

Example 25

3-[6-(4-Chlorophenylamino)-hexylamino]-4-(pyridin-4-yl-amino)-cyclobut-3-ene-1,2-dione (SQ-25)

The title compound was prepared according to the procedure described in example 1B starting from 3-ethoxy-4-(pyridin-4-yl-amino)-3-cyclobutene-1,2-dione prepared according to example 7A and N-(4-chlorophenyl)-hexane-1,6-diamine.
Yield: 89%
$^1$H-NMR (d6-DMSO): 1.33-1.68 (m, 8H), 2.92-2.99 (m, 2H), 3.55-3.60 (m, 2H), 5.72 (t, J=5.4 Hz, 1H), 6.53 (d, J=8.8 Hz, 2H), 7.05 (d, J=8.8 Hz, 2H), 7.42 (d, J=5.8 Hz, 2H), 7.78 (s, br, 1H), 8.40 (d, J=5.8 Hz, 2H), 9.85 (s, br, 1H).
MS: m/z=399 (MH$^+$)

Example 26

3-[6-(4-Chlorophenylamino)-hexylamino]-4-(pyridin-3-yl-amino)-cyclobut-3-ene-1,2-dione (SQ-26)

The title compound was prepared according to the procedure described in example 1B starting from 3-ethoxy-4-(pyridin-3-yl-amino)-3-cyclobutene-1,2-dione prepared according to example 1A and N-(4-chlorophenyl)-hexane-1,6-diamine.
Yield: 86%
$^1$H-NMR (d6-DMSO): 1.30-1.70 (m, 8H), 2.92-2.99 (m, 2H), 3.56-3.64 (m, 2H), 5.71 (s, br, 1H), 6.53 (d, J=8.8 Hz, 2H), 7.05 (d, J=8.8 Hz, 2H), 7.36 (dd, J=4.7, 8.2 Hz, 1H), 7.70 (s, br, 1H), 7.92 (d, br, J=6.5 Hz, 1H), 8.21-8.24 (m, 1H), 8.56 (d, J=2.2 Hz, 1H), 9.72 (s, br, 1H).
MS: m/z=399 (MH$^+$)

Example 27

3-[6-(4-Chlorophenylsulfanyl)-hexylamino]-4-(pyridin-4-yl-amino)-cyclobut-3-ene-1,2-dione (SQ-27)

The title compound was prepared according to the procedure described in example 1B starting from 3-ethoxy-4-(pyridin-4-yl-amino)-3-cyclobutene-1,2-dione prepared according to example 7A and 6-(4-chloro-phenylsulfanyl)-hexylamine
Yield: 62%
$^1$H-NMR (d6-DMSO): 1.33-1.58 (m, 8H), 2.96 (t, J=7.1 Hz, 2H), 3.59 (s, 2H), 7.29-7.37 (m, 4H), 7.42 (d, J=4.7 Hz, 2H), 7.79 (s, br, 1H), 8.39 (d, J=4.7 Hz, 2H), 9.76 (s, br, 1H).
MS: m/z=416 (MH$^+$)

Example 28

(rac) 3-[6-(4-Chlorophenoxy)-1-methyl-hexylamino]-4-(pyridin-3-yl-amino)-cyclobut-3-ene-1,2-dione (SQ-28)

The title compound was prepared from 3-ethoxy-4-(pyridine-3-yl-amino)-3-cyclobutene-1,2-dione (164 mg, 0.75 mmol) prepared according to example 1A and crude 6-(4-chlorophenoxy)-1-methyl-hexylamine (738 mg) in refluxing EtOH (15 ml). After 36 h the solvent was evaporated and the product was isolated by preparative HPLC chromatography using a gradient of 30 to 50% MeCN in 0.01% aq. TFA and subsequent freeze drying of the product containing fractions.
Yield: 12%
¹H-NMR (d6-DMSO): 1.23 (d, J=6.5 Hz, 3H), 1.39-1.71 (m, 8H), 3.93 (t, J=6.3 Hz, 2H), 4.11-4.20 (m, 1H), 6.90 (d, J=8.9 Hz, 2H), 7.27 (d, J=8.9 Hz, 2H), 7.52 (dd, J=4.8, 8.4 Hz, 1H), 8.10-8.16 (m, 2H), 8.30 (d, J=4.8 Hz, 1H), 8.74 (s, 1H), 10.38 (s, 1H).
MS: m/z=414 (MH⁺)

Example 29

3-[4-(4-Chlorophenoxy)-benzylamino]-4-(pyridin-4-yl-amino)-cyclobut-3-ene-1,2-dione (SQ-29)

The title compound was prepared according to the procedure described in example 1B starting from 3-ethoxy-4-(pyridin-4-yl-amino)-3-cyclobutene-1,2-dione prepared according to example 7A and 4-(4-chlorophenoxy)-benzylamine.
Yield: 78%
¹H-NMR (d6-DMSO): 4.81 (s, 2H), 7.01 (d, J=8.9 Hz, 2H), 7.06 (d, J=8.5 Hz, 2H), 7.41-7.44 (m, 6H), 8.39 (d, J=5.6 Hz, 2H).
MS: m/z=406 (MH⁺), 217 (ClC₆H₄OC₆H₄CH₂)

Example 30

3-[4-(4-Chlorophenoxy)-benzylamino]-4-(pyridin-3-yl-amino)-cyclobut-3-ene-1,2-dione (SQ-30)

The title compound was prepared according to the procedure described in example 1B starting from 3-ethoxy-4-(pyridin-3-yl-amino)-3-cyclobutene-1,2-dione prepared according to example 1A and 4-(4-chlorophenoxy)-benzylamine.
Yield: 68%
¹H-NMR (d6-DMSO): 4.81 (s, 2H), 7.01 (d, J=8.9 Hz, 2H), 7.05 (d, J=3.6 Hz, 2H), 7.08-7.44 (m, 5H), 7.91 (d, br, J=7.1 Hz, 1H), 8.23 (d, J=4.5 Hz, 1H), 8.55 (d, J=2.5 Hz, 1H), 9.74 (s, br, 1H).
MS: m/z=406 (MH⁺)

Example 31

3-[4-(4-Chlorophenoxymethyl)-benzylamino]-4-(pyridin-4-yl-amino)-cyclobut-3-ene-1,2-dione (SQ-31)

The title compound was prepared according to the procedure described in example 1B starting from 3-ethoxy-4-(pyridine-4-yl-amino)-3-cyclobutene-1,2-dione prepared according to example 7A and 4-(4-chlorophenoxy-methyl)-benzylamine.
Yield: 71%
¹H-NMR (d6-DMSO): 4.87 (d, J=8.5 Hz, 2H), 5.16 (s, 2H), 7.07 (d, J=8.8 Hz, 2H), 7.38 (d, J=8.8 Hz, 2H), 7.41-7.56 (m, 6H), 8.19 (s, 1H), 8.45 (d, J=4.8 Hz, 2H), 9.93 (s, br, 1H).
MS: m/z=420 (MH⁺)

Example 32

3-[4-(4-Chlorophenoxymethyl)-benzylamino]-4-(pyridin-3-yl-amino)-cyclobut-3-ene-1,2-dione (SQ-32)

The title compound was prepared according to the procedure described in example 1B starting from 3-ethoxy-4-(pyridine-3-yl-amino)-3-cyclobutene-1,2-dione prepared according to example 1A and 4-(4-chlorophenoxy-methyl)-benzylamine.
Yield: 81%
¹H-NMR (d6-DMSO): 4.82 (s, 2H), 5.11 (s, 2H), 7.02 (dd, J=2.2, 6.9 Hz, 2H), 7.29-7.48 (m, 7H), 7.91 (d, J=7.7 Hz, 1H), 8.8 (s, br, 1H), 8.23 (dd, J=1.3, 4.6 Hz, 1H), 8.55 (d, J=2.6 Hz, 1H), 9.75 (s, br, 1H).
MS: m/z=420 (MH⁺)

Example 33

3-[3-(4-Chlorophenoxy)-benzylamino]-4-(pyridin-3-yl-amino)-cyclobut-3-ene-1,2-dione (SQ-33)

The title compound was prepared according to the procedure described in example 1B starting from 3-ethoxy-4-(pyridin-3-yl-amino)-3-cyclobutene-1,2-dione prepared according to example 1A and 3-(4-chlorophenoxy)-benzylamine.
Yield: 84%
¹H-NMR (d6-DMSO): 4.80 (d, J=6.1 Hz, 2H), 6.96-7.08 (m, 4H), 7.18 (d, J=7.5 Hz, 1H), 7.37-7.44 (m, 4H), 7.90 (d, J=6.8 Hz, 1H), 8.07 (s, br, 1H), 8.24 (d, J=4.0 Hz, 1H), 8.54 (d, J=2.1 Hz, 1H), 9.79 (s, br, 1H).
MS: m/z=406 (MH⁺)

Example 34

3-[4-Phenoxybenzylamino]-4-(pyridin-4-yl-amino)-cyclobut-3-ene-1,2-dione (SQ-34)

The title compound was prepared according to the procedure described in example 1B starting from 3-ethoxy-4-(pyridin-4-yl-amino)-3-cyclobutene-1,2-dione prepared according to example 7A and 4-phenoxybenzylamine.
Yield: 55%
¹H-NMR (d6-DMSO): 4.80 (s, 2H), 6.98-7.05 (m, 4H), 7.14 (t, J=7.4 Hz, 1H), 7.34-7.43 (m, 5H), 7.92 (d, J=7.8 Hz, 1H), 8.05 (s, br, 1H), 8.23 (dd, J=1.3, 4.6 Hz, 1H), 8.55 (d, J=2.6 Hz, 1H), 9.75 (s, br, 1H).
MS: m/z=372 (MH⁺)

Example 35

3-[3-(4-Chlorophenoxymethyl)-benzylamino]-4-(pyridin-3-yl-amino)-cyclobut-3-ene-1,2-dione (SQ-35)

The title compound was prepared according to the procedure described in example 1B starting from 3-ethoxy-4-(pyridine-3-yl-amino)-3-cyclobutene-1,2-dione prepared according to example 1A and 3-(4-chlorophenoxy-methyl)-benzylamine.
Yield: 65%
¹H-NMR (d6-DMSO): 4.77 (d, J=5.5 Hz, 2H), 5.05 (s, 2H), 6.96 (d, J=8.8 Hz, 2H), 7.23-7.40 (m, 7H), 7.84 (d, J=7.1 Hz, 1H), 8.00 (s, br, 1H), 8.16 (d, J=4.3 Hz, 1H), 8.47 (d, J=1.9 Hz, 1H), 9.69 (s, br, 1H).
MS: m/z=420 (MH⁺)

Example 36

3-[3-(4-Chlorophenoxymethyl)-benzylamino]-4-(pyridin-4-yl-amino)-cyclobut-3-ene-1,2-dione (SQ-36)

The title compound was prepared according to the procedure described in example 1B starting from 3-ethoxy-4-(pyridine-4-yl-amino)-3-cyclobutene-1,2-dione prepared according to example 7A and 3-(4-chlorophenoxy-methyl)-benzylamine.

Yield: 63%

$^1$H-NMR (d6-DMSO): 4.77 (d, J=4.8 Hz, 2H), 5.04 (s, 2H), 6.96 (d, J=8.8 Hz, 2H), 7.23-7.40 (m, 8H), 8.09 (s, br, 1H), 8.33 (d, J=5.2 Hz, 2H), 9.83 (s, br, 1H).

MS: m/z=420 (MH$^+$)

Example 37

3-[2-(1-Benzylpiperidin-4-yl)ethylamino]-4-(pyridin-3-yl-amino)-cyclobut-3-ene-1,2-dione (SQ-37)

3-Ethoxy-4-(pyridine-3-yl-amino)-3-cyclobutene-1,2-dione (164 mg, 0.75 mmol) prepared according to example 1A and 2-(1-benzylpiperidin-4-yl)-ethylamine (196 mg, 0.90 mmol) in EtOH (4 mL) were stirred and heated to 150° C. in a sealed vessel in a microwave synthesizer for 3 min. After cooling to r.t. the precipitate was filtered off and washed with EtOH (3×3 mL) and dried in vacuo.

Yield: 73%

$^1$H-NMR (d6-DMSO): 1.11-1.24 (m, 2H), 1.24-1.45 (m, 1H), 1.51 (app q, J=6.8 Hz, 2H), 1.65 (d, J=11.1 Hz, 2H), 1.89 (dd, J=9.7, 11.4 Hz, 2H), 2.78 (d, J=11.4 Hz, 2H), 3.43 (s, 2H), 3.63 (s, br, 2H), 7.22-7.39 (m, 6H), 7.67 (s, br, 1H), 7.92 (d, J=7.4 Hz, 1H), 8.23 (dd, J=1.4, 4.7 Hz, 1H), 8.56 (d, J=2.6 Hz, 1H), 9.70 (s, br, 1H).

MS: m/z=391 (MH$^+$)

Example 38

3-[2-(1-Benzylpiperidin-4-yl)-ethylamino]-4-(pyridin-4-yl-amino)-cyclobut-3-ene-1,2-dione (SQ-38)

The title compound was prepared according to the procedure described in example 37 starting from 3-ethoxy-4-(pyridine-4-yl-amino)-3-cyclobutene-1,2-dione prepared according to example 7A and 2-(1-benzylpiperidin-4-yl)-ethylamine.

Yield: 71%

$^1$H-NMR (d6-DMSO): 1.13-1.24 (m, 2H), 1.24-1.45 (m, 1H), 1.49 (app q, J=6.7 Hz, 2H), 1.65 (d, J=11.4 Hz, 2H), 1.90 (dd, J=10.0, 11.4 Hz, 2H), 2.78 (d, J=11.4 Hz, 2H), 3.43 (s, 2H), 3.64 (d, 5.0 Hz, 2H), 7.22-7.31 (m, 5H), 7.42 (d, J=5.2 Hz, 2H), 7.76 (s, br, 1H), 8.40 (d, J=6.2 Hz, 2H), 9.84 (s, br, 1H).

MS: m/z=391 (MH$^+$)

Example 39

3-(6-[4-(Morpholinomethyl)-phenoxy]-hexylamino)-4-(pyridin-3-yl-amino)-3-cyclobutene-1,2-dione (SQ-39)

To a solution of 3-ethoxy-4-(pyridin-3-yl-amino)-3-cyclobutene-1,2-dione (350 mg, 1.6 mmol) in ethanol (1.4 mL) was added 6-[4-(morpholinomethyl)-phenoxy]-hexylamine (469 mg, 1.6 mmol) in ethanol (5 mL). The reaction was allowed to stir at r.t. for 18 h, then filtered. The solid was washed with cold ethanol, then ether to give the title compound.

Yield: 564 mg, 76%

$^1$H NMR (d6-DMSO): 9.74 (s, 1H), 8.54 (d, J=2.4 Hz, 1H), 8.20 (dd, J=4.4, 1.4 Hz, 1H), 7.92 (m, 1H), 7.70 (s, br, 1H), 7.35 (dd, J=8.2, 4.6 Hz, 1H), 7.15 (d, J=8.4 Hz, 2H), 6.84 (d, J=8.4 Hz, 2H), 4.36 (s, br, 1H), 3.91 (t, J=6.3 Hz, 2H), 3.54-3.42 (m, 6H), 2.31 (s, br, 4H), 1.70 (t, J=6.3 Hz, 2H), 1.58 (t, J=6.6 Hz, 2H), 1.41 (s, br, 7H).

MS: m/z=465 (MH$^+$).

The HCl salt was then made by heating 400 mg of the above product in 4 N HCl/dioxane for 1 h, followed by addition of ether, filtration, and washing the solid with ether. This gave 457 mg of the HCl salt.

$^1$H NMR (d6-DMSO): δ 11.67 (s, 1H), 10.60 (s, br, 1H), 8.91 (s, 1H), 8.38 (d, J=4.8 Hz, 1H), 8.30 (d, J=8.1 Hz, 1H), 7.79 (m, 1H), 7.44 (d, J=8.4 Hz, 2H), 6.98 (d, J=8.4 Hz, 2H), 4.22 (s, br, 2H), 3.99-3.89 (m, 4H), 3.20-3.05 (m, 4H), 1.71-1.43 (m, 8H).

MS: m/z=465 (MH$^+$).

A(II): Synthesis of Amine Compounds (Examples 40-60).

Example 40

General Procedure I 6-(4-Chlorophenoxy)-hexylamine

6-Bromohexylphthalimide (12.40 g, 40 mmol; reactant 1) and 4-chlorophenol (5.16 g, 40 mmol; reactant 2) were dissolved in DMF (100 mL). After the addition of K$_2$CO$_3$ (12.16 g, 88 mmol) the reaction mixture was heated to 90° C. for 20 h. After cooling to r.t. the mixture was concentrated under reduced pressure and the residue was taken up in EtOAc/water (500/100 mL). After separation of the aqueous layer the organic layer was washed with pH 7 phosphate buffer, dried (Na$_2$SO$_4$) and evaporated under reduced pressure to give 12.7 g (88%) of a white solid.

This solid was dissolved in EtOH/THF (1/1; 250 mL). After addition of N$_2$H$_4$×H$_2$O (80%, 12.5 mL, ~175 mmol) the mixture was heated to 90° C. for 16 h. The mixture was concentrated under reduced pressure, THF (250 mL) was added and the resulting slurry was sonicated for 1 h. The suspension was filtered and the residue was washed with THF (3×20 mL). The filtrate was evaporated to dryness. The residue was suspended in THF (50 mL) and the suspension was filtered. Evaporation of the filtrate gave 6.34 g (70% over two steps) of 6-(4-chlorophenoxy)-hexylamine as a yellow oil, pure enough for further reactions.

$^1$H-NMR (CDCl$_3$): 1.36-1.79 (m, 10H), 2.70 (t, J=6.9 Hz, 2H), 3.90 (t, J=6.5 Hz, 2H), 6.81 (d, J=9.1 Hz, 2H), 7.21 (d, J=9.1 Hz, 2H).

Examples 41-50

Examples 41-50 were synthesized by the procedure described in general procedure I.

| Ex. | Compound | Reactant 1 | Reactant 2 | Yield | NMR data |
|---|---|---|---|---|---|
| 41 | 5-(4-Chlorophenoxy)-pentylamine | 5-bromopentylphthalimide | 4-chlorophenol | 1.80 g, 83% | $^1$H-NMR (CDCl$_3$): 1.48-1.53 (m, 4H), 1.73-1.82 (m, 2H), 2.11 (s, br, 2H), 2.71-2.75 (m, 2H), 3.92 (t, J = 6.4 Hz, 2H), 6.80 (d, J = 9.1 Hz, 2H), 7.20 (d, = 9.1 Hz, 2H). |
| 42 | 4-(4-Chlorophenoxy)-butylamine | 4-bromobutyl phthalimide | 4-chlorophenol | 1.05 g, 58% | $^1$H-NMR (CDCl$_3$): 1.57-1.67 (m, 2H), 1.77-1.96 (m, 4H), 2.77 (t, J = 7.0 Hz, 2H), 3.94 (t, J = 6.3 Hz, 2H), 6.81 (d, J = 9.0 Hz, 2H), 7.21 (d, J = 9.0 Hz, 2H). |

| Ex. | Compound | Reactant 1 | Reactant 2 | Yield | NMR data |
|---|---|---|---|---|---|
| 43 | 8-(4-Chlorophenoxy)-octylamine | 8-bromooctyl phthalimide | 4-chlorophenol | 1.67 g, 69% | $^1$H-NMR (CDCl$_3$): 1.32-1.46 (m, 10H), 1.71-1.85 (m, 4H), 2.69 (t, J = 7.0 Hz, 2H), 3.91 (t, J = 6.5 Hz, 2H), 6.80 (d, J = 9.1 Hz, 2H), 7.21 (d, J = 9.1 Hz, 2H). |
| 44 | 6-(4-Methylphenoxy)-hexylamine | 6-bromohexyl phthalimide | 4-methylphenol | 3.46 g, 83% | $^1$H-NMR (CDCl$_3$): 1.36-1.51 (m, 6H), 1.74-1.79 (m, 2H), 2.28 (s, 3H), 2.50 (s, br 2H), 2.71 (t, J = 6.9 Hz, 2H), 3.92 (t, J = 6.5 Hz, 2H), 6.79 (d, J = 8.5 Hz, 2H), 7.06 (d, J = 8.5 Hz, 2H). |
| 45 | 6-Phenoxyhexylamine | 6-bromohexyl phthalimide | phenol | 3.00 g, 78% | $^1$H-NMR (CDCl$_3$): 1.41-1.51 (m, 6H), 1.76-1.85 (m, 2H), 2.00 (s, br 2H), 2.71 (t, J = 6.7 Hz, 2H), 3.95 (t, J = 6.5 Hz, 2H), 6.87-6.94 (m, 3H), 7.21-7.30 (m, 2H). |
| 46 | 6-(4-Methoxyphenoxy)-hexylamine | 6-bromohexyl phthalimide | 4-methoxyphenol | 3.27 g, 73% | $^1$H-NMR (CDCl$_3$): 1.36-1.51 (m, 6H), 1.73-1.78 (m, 2H), 2.45 (s, br 2H), 2.71 (t, J = 6.9 Hz, 2H), 3.76 (s, 3H), 3.90 (t, J = 6.5 Hz, 2H), 6.82 (s, 4H). |
| 47 | 6-(3,4-Dichlorophenoxy)-hexylamine | 6-bromohexyl phthalimide | 3,4-dichlorophenol | 3.77 g, 72% | $^1$H-NMR (CDCl$_3$): 1.38-1.51 (m, 6H), 1.69-1.80 (m, 4H), 2.71 (t, J = 6.8 Hz, 2H), 3.91 (t, J = 6.5 Hz, 2H), 6.73 (dd, J = 2.8, 8.8 Hz, 1H), 6.98 (d, J = 2.9 Hz, 1H), 7.30 (d, J = 8.8 Hz, 1H). |
| 48 | 6-(Pyridin-3-yloxy)-hexylamine | 6-bromohexyl phthalimide | 3-hydroxypyridine | 2.11 g, 54% | $^1$H-NMR (CDCl$_3$): 1.39-1.96 (m, 10H), 2.71 (t, J = 6.8 Hz, 2H), 4.00 (t, J = 6.4 Hz, 2H), 7.17-7.20 (m, 2H), 8.20 (dd, J = 1.9, 4.1 Hz, 1H), 8.30 (m, 1H). |
| 49 | 6-(4-Trifluoromethylphenoxy)-hexylamine | 6-bromohexyl phthalimide | 4-trifluoromethylphenol | 3.89 g, 75% | $^1$H-NMR (CDCl$_3$): 1.38-1.53 (m, 8H), 1.78-1.83 (m, 2H), 2.71 (t, J = 6.5 Hz, 2H), 3.99 (t, J = 6.5 Hz, 2H), 6.94 (d, J = 8.7 Hz, 2H), 7.52 (d, J = 8.7 Hz, 2H). |
| 50 | 4-(6-Amino-hexyloxy)-benzonitrile | 6-bromohexyl phthalimide | 4-hydroxybenzonitrile | 3.14 g, 72% | $^1$H-NMR (CDCl$_3$): 1.38-1.51 (m, 8H), 1.79-1.84 (m, 2H), 2.71 (t, J = 6.5 Hz, 2H), 4.00 (t, J = 6.5 Hz, 2H), 6.93 (d, J = 8.8 Hz, 2H), 7.57 (d, J = 8.8 Hz, 2H). |

Example 51

2-[4-(4-Chlorophenoxy)-phenyl]-ethylamine

The title compound was synthesized according to the procedure in WO 04/20415 with additional 10 eq. NEt$_3$.
Yield: 34%.

Example 52

7-(4-Chlorophenoxy)-heptylamine

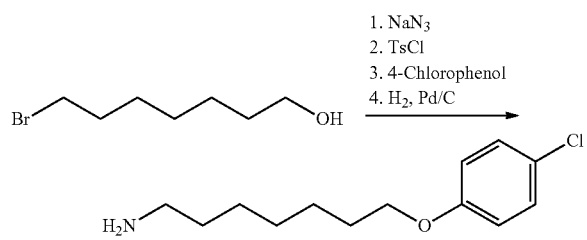

NaN$_3$ (390 mg, 6.0 mmol) was added to a solution of 7-bromoheptanol (880 µL, 5.7 mmol) in DMF (5 mL). The mixture was stirred for 24 at r.t. and additional 3 h at 80° C. to complete the reaction. The mixture was concentrated under reduced pressure, the residue was dissolved in water/Et$_2$O (10/20 mL), the organic layer was separated, dried over Na$_2$SO$_4$ and filtered. Concentration under reduced pressure yielded 7-azidoheptanol (710 mg, 78%) as an colourless oil which was pure enough for further reactions.

TsCl (955 mg, 5.0 mmol) and pyridine (435 µL, 5.4 mmol) were added to a solution of 7-azidoheptanol (700 mg, 4.5 mmol) in CH$_2$Cl$_2$ (5 mL). The solution was stirred for 18 h at r.t. The solution was diluted with EtOAc (20 mL) and washed with 5% aqueous KHSO$_4$ solution, sat. aqueous NaHCO$_3$ solution and pH 7 phosphate buffer. The org. layer was concentrated and the residue was treated with water (10 mL) for 4 h to hydrolyse excess TsCl. The mixture was diluted with EtOAc (20 mL), washed with aqueous NaHCO$_3$, dried (Na$_2$SO$_4$), and filtered. Concentration under reduced pressure yielded 7-azidoheptyltosylate (920 mg, 66%). The product was pure enough for further reactions.

7-Azidoheptyltosylate (920 mg, 3.8 mmol) was dissolved in DMF (12 mL). 4-Chlorophenol (650 mg, 5.0 mmol) and K$_2$CO$_3$ (1.7 g, 12.3 mmol) were added and the mixture was heated to 90° C. for 4 h. The mixture was concentrated under reduced pressure, the residue was partitioned between EtOAc (100 mL) and water (25 mL). The organic layer was dried, filtered and concentrated under reduced pressure. Flash chromatography (silica gel, hexanes/EtOAc 95/5) yielded 1-azido-7-(4-chlorophenoxy)-heptane (579 mg, 49%). 1-Azido-7-(4-chlorophenoxy)-heptane (570 mg, 2.1 mmol) was dissolved in EtOH (3 mL). Pd/C (101 mg, 10%) was added and the mixture was stirred under an atmosphere of H$_2$ for 75 min. The reaction mixture was filtered through celite and concentrated under reduced pressure to yield the title compound (453 mg, 89%). The product contained ~25% of 7-(phenoxy)-heptylamine.

$^1$H-NMR (CDCl$_3$): 1.37-1.54 (m, 6H), 1.72-1.85 (m, 4H), 2.74-2.78 (m, 2H), 3.09 (s, br, 2H), 3.88-3.94 (m, 2H), 6.80 (d, J=8.9 Hz, 2H), 7.21 (d, J=8.9 Hz, 2H).

Example 53

4-(4-Chlorophenoxy-methyl)-benzylamine

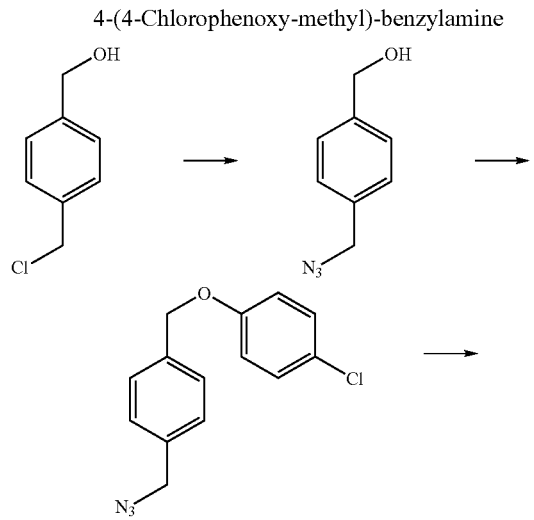

The title compound was synthesized in a three step reaction:

1. (4-Azidomethyl-phenyl)-methanol 4-(Chloromethyl)-benzylalcohol (5.01 g, 32 mmol) and NaN₃ (2.50 g, 38.4 mmol) were stirred in DMF (25 mL) at 90° C. for 17 h. The solvent was removed under reduced pressure and the residue was partitioned between water (50 mL) and Et₂O (100 mL). The aqueous layer was extracted with Et₂O (2×50 mL) and the combined org. layers were dried over Na₂SO₄. After filtration the solvent was removed under reduced pressure to give (4-azidomethyl-phenyl)-methanol, pure enough for further reaction.

Yield: 5.57 g, qu

¹H-NMR (CDCl₃): 1.96 (t, J=5.2 Hz, 1H), 4.33 (s, 2H), 4.69 (d, J=5.2 Hz, 2H), 7.30 (d, J=8.1 Hz, 2H), 7.38 (d, J=8.1 Hz, 2H).

IR (ATR): 3300, 2094 (ss), 1661, 1251, 1015.

2. 4-(4-Chlorophenoxymethyl)-benzylazide

Triphenylphosphine (4.33 g, 16.5 mmol) was dissolved in dry THF (20 mL) under an atmosphere of argon. After cooling to −40° C., diisopropyl-azodicarboxylate (DIAD, 3.2 mL, 16.5 mmol) was added and the mixture was stirred at −40° C. for 10 min. A solution of 4-chlorophenol (2.12 g, 16.5 mmol) and (4-azidomethyl-phenyl)-methanol (2.45 g, 15 mmol) in dry THF (10 mL) was added dropwise. After addition, the cooling bath was removed and stirring was continued for 1 h. The solution was diluted with Et₂O (150 mL) and washed with pH-7-phosphate buffer solution (1×50 mL). The organic layer was dried over Na₂SO₄, filtered and evaporated under reduced pressure. The resulting residue was purified by flash chromatography (2-3% EtOAc in hexane) to give the title compound.

Yield: 3.54 g, 86%

¹H-NMR (CDCl₃): 4.33 (s, 2H), 5.03 (s, 2H), 6.86-7.25 (m, 4H), 7.33 (d, J=8.1 Hz, 2H), 7.42 (d, J=8.1 Hz, 2H).

3. 4-(4-Chloro-phenoxymethyl)-benzylamine 4-(4-Chloro-phenoxymethyl)-benzylazide (3.2 g, 11.7 mmol) was dissolved in MeOH (50 mL). NEt₃ (11.35 mL, 81.9 mmol) and SnCl₂×2H₂O (5.28 g, 23.4 mmol) were added and the exothermic reaction was stirred under reflux. When boiling ceased the mixture was heated to reflux for additional 45 min. After cooling to r.t. the mixture was filtered and the filtrate was evaporated to dryness. The residue was dissolved in CH₂Cl₂ (300 mL) and this solution was washed with sat. aq. NaHCO₃-solution (1×100 mL), dried over Na₂SO₄, filtered and evaporated to dryness to give the title compound, pure enough for further reaction.

Yield: 9.24 g, 86%

¹H-NMR (CDCl₃): 1.53 (s, br, 2H), 3.88 (s, 2H), 5.03 (s, 2H), 6.87-7.26 (m, 4H), 7.33 (d, J=8.2 Hz, 2H), 7.38 (d, J=8.2 Hz, 2H).

Example 54

3-(4-Chlorophenoxy-methyl)-benzylamine

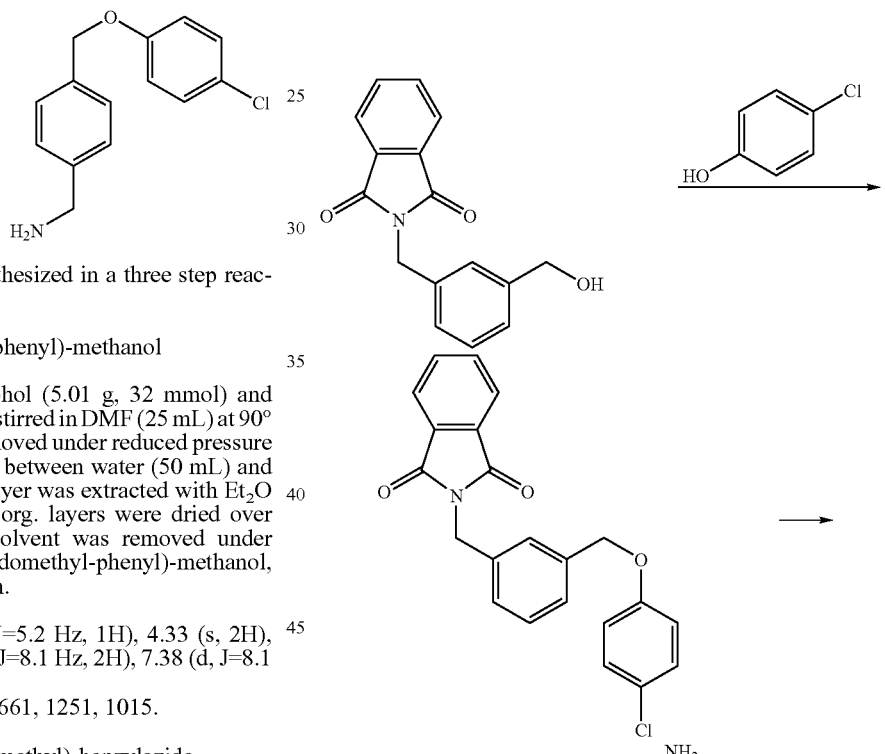

The title compound was synthesized in a two step reaction:

1. 2-[3-(4-Chloro-phenoxymethyl)-benzyl]-phthalimide

Triphenylphosphine (280 mg, 1.07 mmol) was dissolved in dry THF (2 mL) under an atmosphere of argon. After cooling to −40° C., DIAD (0.21 mL, 1.07 mmol) was added and the mixture was stirred at −40° C. for 10 min. A solution of 4-chlorophenol (138 mg g, 1.07 mmol) and 2-(3-hydroxymethylbenzyl)-phthalimide (261 mg, 0.98 mmol) in dry THF (3 mL) was added dropwise. After addition, the cooling bath was removed and stirring was continued for 2 h. The solution was diluted with $Et_2O$ (40 mL) and washed with pH-7-phosphate buffer solution (1×20 mL). The organic layer was dried over $Na_2SO_4$, filtered and evaporated under reduced pressure. The resulting residue was purified by flash chromatography (EtOAc/hexane 1:5) to give the title compound.

Yield: 361 mg, 98%

$^1$H-NMR (CDCl$_3$): 4.86 (s, 2H), 5.00 (s, 2H), 6.85-7.22 (m, 4H), 7.31-7.41 (m, 3H), 7.46 (s, 1H), 7.46-7.86 (m, 4H).

2. 3-(4-Chlorophenoxy-methyl)-benzylamine

2-[3-(4-Chloro-phenoxymethyl)-benzyl]-phthalimide (345 mg, 0.91 mmol) and hydrazine hydrate (0.27 mL, 4.5 mmol) were dissolved in THF (2.5 mL) and EtOH (2.5 mL). The mixture was heated to reflux for 17 h, cooled to r.t. and evaporated to dryness. The residue was suspended in THF (6 mL). The precipitate was filtered and washed with THF (4×3 mL). The filtrate was evaporated to dryness to give the title compound, pure enough for further reactions.

Yield: 109 mg, 48%

$^1$H-NMR (CDCl$_3$): 1.76 (s, br, 2H), 3.89 (s, 2H), 5.02 (s, 2H), 6.90 (d, J=9.1 Hz, 2H), 7.21-7.38 (m, 6H).

Example 55

7-Phenyl-heptylamine

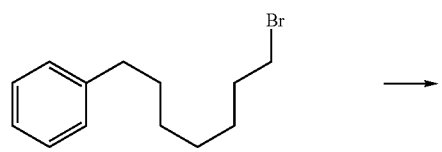

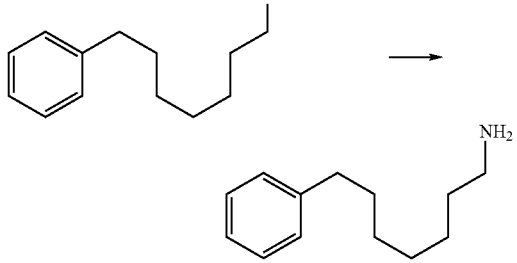

The title compound was synthesized in a two step reaction:

1. 7-Phenyl-heptylazide

7-Phenyl-hepthylbromide (5.0 g, 19.5 mmol) and $NaN_3$ (1.65 g) were stirred in DMF (50 mL) at 100° C. for 3 h. After cooling to r.t. the solvent was removed under reduced pressure and the residue was partitioned between water (60 mL) and $Et_2O$ (120 mL). The aqueous layer was separated, extracted with $Et_2O$ (1×80 mL) and the combined org. layers were dried over $Na_2SO_4$. After filtration the solvent was removed under reduced pressure to give the title compound, pure enough for further reactions.

Yield: 3.97 g, 94%

$^1$H-NMR (CDCl$_3$): 1.33-1.38 (m, 6H), 1.55-1.64 (m, 4H), 2.60 (t, J=7.7 Hz, 2H), 3.24 (t, J=6.9 Hz, 2H), 7.15-7.29 (m, 5H).

2. 7-Phenyl-heptylamine

A solution of 7-phenylheptylazide (3.97 g, 18.3 mmol) in EtOH (15 mL) was added to palladium on carbon (200 mg) in EtOH (35 mL) under an atmosphere of Hydrogen. The mixture was stirred for 24 h at r.t. The mixture was filtered through celite and the solvent was removed under reduced pressure to give the title compound.

Yield: 2.99 g, 85%

$^1$H-NMR (CDCl$_3$): 1.33-1.72 (m, 10H), 2.22-2.72 (m, 4H), 7.10-7.32 (m, 5H).

Example 56

6-[4-(Morpholin-4-yl-ethoxy)-phenoxy)-hexylamine

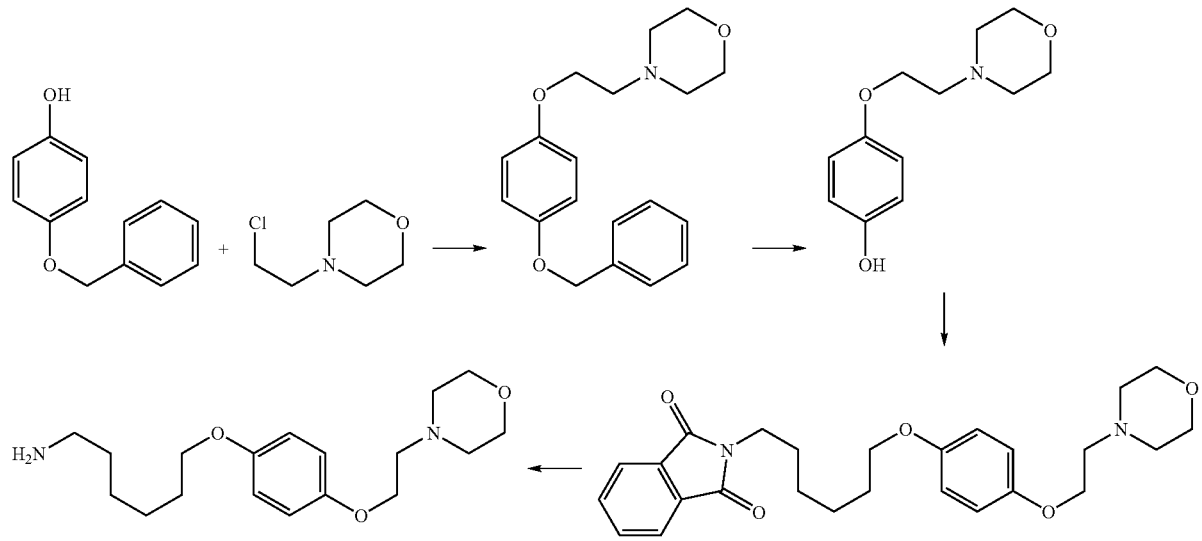

The title compound was synthesized in a four step reaction:

1. 4-[2-(Benzyloxy-phenoxy)-ethyl]-morpholine

4-Benzyloxyphenol (4.0 g, 20 mmol), chloroethylmorpholine hydrochloride (3.72 g, 20 mmol) and $K_2CO_3$ (5.53 g, 40 mmol) were suspended in DMF (50 mL) under an atmosphere of argon and stirred at 105° C. for 17 h. The solvent was removed under reduced pressure and the residue was partitioned between water (80 mL) and $Et_2O$ (150 mL). The aqueous layer was extracted with $Et_2O$ (1×30 mL), the combined org. layers were dried over $Na_2SO_4$, filtered and concentrated under reduced pressure. The residue was purified by flash chromatography (0-10% MeOH in EtOAc) to give the title compound.

Yield: 4.79 g, 76%

$^1$H-NMR (CDCl$_3$): 2.57 (t, J=4.7 Hz, 4H), 2.77 (t, J=5.7 Hz, 2H), 3.73 (t, J=4.7 Hz, 4H), 4.06 (t, J=5.7 Hz, 2H), 5.01 (s, 2H), 6.81-6.92 (m, 4H), 7.30-7.43 (m, 5H).

2. 4-(2-Morpholin-4-yl-ethoxy)-phenol

A solution of 4-[2-(Benzyloxy-phenoxy)-ethyl]-morpholine (4.77 g, 15.2 mmol) in EtOH (35 mL) was added to palladium on carbon (250 mg) in EtOH (15 mL) under an atmosphere of Hydrogen. The mixture was stirred for 17 h at r.t. The mixture was filtered through celite and the solvent was removed under reduced pressure to give the title compound.

Yield: 3.30 g, 97%

$^1$H-NMR (CDCl$_3$): 2.61 (t, J=4.7 Hz, 4H), 2.79 (t, J=5.6 Hz, 2H), 3.76 (t, J=4.7 Hz, 4H), 4.04 (t, J=5.6 Hz, 2H), 6.05 (s, br, 1H), 6.72 (s, 4H).

3. 2-[6-(4-(2-Morpholin-4-yl-ethoxy)-phenoxy)-hexyl]-phthalimide 4-(2-Morpholin-4-yl-ethoxy)-phenol (3.39 g, 15.2 mmol), N-(6-bromohexyl)-phthalimide (4.72 g, 15.2 mmol) and $K_2CO_3$ (4.20 g, 30.4 mmol) were suspended in DMF (35 mL) under an atmosphere of argon and stirred at 95° C. for 17 h. The solvent was evaporated under reduced pressure and the residue was partitioned between water (150 mL) and $CH_2Cl_2$ (150 mL). The aqueous layer was extracted with $CH_2Cl_2$ (2×100 mL), the combined org. layers were dried over $Na_2SO_4$, filtered and the solvent was removed under reduced pressure. The residue was purified by flash chromatography (EtOAc) to give the title compound together with some starting phenol (≈2:1). The mixture was used for subsequent reactions without further purification.

Yield: 5.45 g; ≈64%

$^1$H-NMR (CDCl$_3$): 1.35-1.85 (m, 8H), 2.57 (t, J=4.7 Hz, 4H), 3.71-3.76 (m, 6H), 3.89 (t, J=6.4 Hz, 4H), 4.06 (t, J=5.7 Hz, 2H), 6.72-6.85 (m, 4H), 7.69-7.86 (m, 4H).

4. 6-[4-(Morpholin-4-yl-ethoxy)-phenoxy)-hexylamine

2-[6-(4-(2-Morpholin-4-yl-ethoxy)-phenoxy)-hexyl]-phthalimide (5.46 g crude mixture from above, ≈9.67 mmol) and hydrazine hydrate (3.66 ml, 60 mmol) were dissolved in EtOH (80 mL) and stirred under reflux for 17 h. The precipitate was filtered off and washed with EtOH (1×50 mL). The filtrate was concentrated under reduced pressure, the residue was suspended in THF (20 mL) and the precipitate was filtered off, washed with THF (2×5 mL) and the filtrate was concentrated under reduced pressure to give the title compound together with some 4-(2-morpholin-4-yl-ethoxy)-phenol (≈2:1).

Yield: 3.89 g, qu $^1$H-NMR (CDCl$_3$): 1.35-1.85 (m, 8H), 2.21 (s, br, 2H), 2.57 (t, J=4.7 Hz, 4H), 2.71 (t, J=6.8 Hz, 2H), 2.78 (t, J=5.7 Hz, 2H), 3.74 (t, J=4.7 Hz, 4H), 3.90 (t, J=6.5 Hz, 2H), 4.06 (t, J=5.7 Hz, 2H), 6.82 (s, 4H).

This material was used in the next step (1.4 eq) without further purification.

Example 57

6-(4-Chlorophenylsulfanyl)-hexylamine

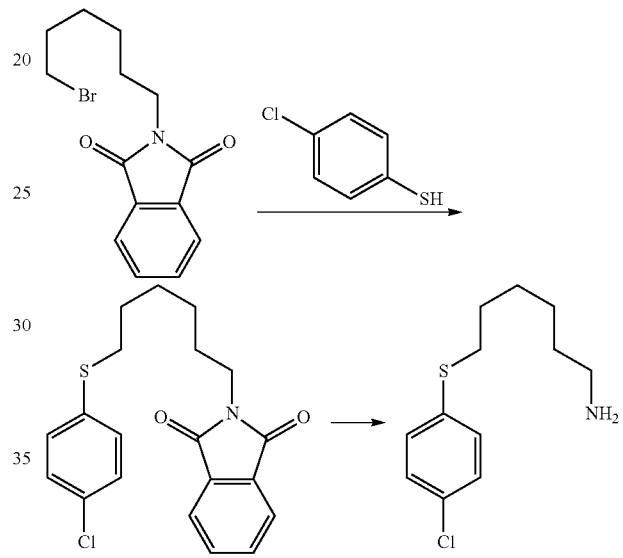

The title compound was synthesized in a two step reaction:

1. 2-[6-(4-Chlorophenylsulfanyl)-hexylphthalimide

4-Chlorothiophenol (2.89 g, 20 mmol), N-(6-bromohexyl)-phthalimide (6.20 g, 20 mmol) and $K_2CO_3$ (5.53 g, 40 mmol) were suspended in DMF (50 mL) under an atmosphere of argon and stirred at 90° C. for 23 h. The solvent was evaporated under reduced pressure and the residue was partitioned between water (100 mL) and $CH_2Cl_2$ (150 mL). The aqueous layer was extracted with $CH_2Cl_2$ (2×100 mL), the combined org. layers were dried over $Na_2SO_4$, filtered and the solvent was removed under reduced pressure to give the title compound, pure enough for further reactions.

Yield: 7.49 g, qu $^1$H-NMR (CDCl$_3$): 1.29-1.80 (m, 8H), 2.87 (t, J=7.2 Hz, 2H), 3.67 (t, J=7.2 Hz, 2H), 7.23 (s, 4H), 7.69-7.85 (m, 4H).

2. 6-(4-Chlorophenylsulfanyl)-hexylamine

2-[6-(4-Chloro-phenylsulfanyl)-hexylphthalimide (7.47 g, 20 mmol) and hydrazine hydrate (6.1 ml, 100 mmol) were dissolved in THF (50 mL) and EtOH (50 mL) and stirred under reflux for 17 h. The solvent was removed under reduced pressure, the residue was suspended in THF (100 mL) and the precipitate was filtered off, washed with THF (1×50 mL) and the filtrate was concentrated under reduced pressure. The residue was resuspended in THF (25 mL), the precipitate was filtered off and the filtrate was concentrated to give the title compound.

Yield: 4.31 g, 88%

$^1$H-NMR (CDCl$_3$): 1.20-1.81 (m, 10H), 2.68 (t, J=6.7 Hz, 2H), 2.89 (t, J=7.3 Hz, 2H), 7.24 (s, 4H).

This material was used in the next step (1.4 eq) without further purification.

Example 58

N-(4-Chlorophenyl)-hexane-1,6-diamine

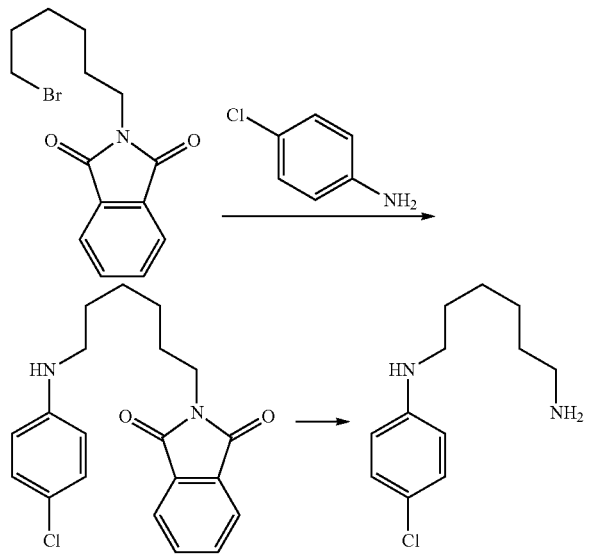

The title compound was synthesized in a two step reaction:

1. 2-[6-(4-Chlorophenylamino)-hexyl]-phthalimide

4-Chloroaniline (2.55 g, 20 mmol), N-(6-bromohexyl)-phthalimide (6.20 g, 20 mmol) and K$_2$CO$_3$ (2.76 g, 20 mmol) were suspended in DMF (50 mL) under an atmosphere of argon and stirred at 90° C. for 25 h. The solvent was evaporated under reduced pressure and the residue was partitioned between water (100 mL) and Et$_2$O (100 mL). The aqueous layer was extracted with Et$_2$O (2×50 mL), the combined org. layers were dried over Na$_2$SO$_4$, filtered and the solvent was removed under reduced pressure. The residue was purified by flash chromatography (EtOAc/hexane 1:6 to 1:3) to give the title compound (3.41 g), together with some 4-chloroaniline (≈2:1).

Yield: 3.41 g, 40%

$^1$H-NMR (CDCl$_3$): 1.29-1.75 (m, 8H), 3.05 (t, J=7.0 Hz, 2H), 3.65 (s, br, 1H), 3.69 (t, J=7.2 Hz, 2H), 6.50 (d, J=8.7 Hz, 2H), 7.08 (d, J=8.7 Hz, 2H), 7.69-7.85 (m, 4H).

2. N-(4-Chloro-phenyl)-hexane-1,6-diamine

2-[6-(4-Chloro-phenylamino)-hexyl]-phthalimide (3.41 g crude from above, 8.4 mmol) and hydrazine hydrate (2.5 ml, 41.5 mmol) were dissolved in THF (25 mL) and EtOH (25 mL) and stirred under reflux for 21 h. The solvent was removed under reduced pressure, the residue was suspended in THF (50 mL) and the precipitate was filtered off, washed with THF (2×5 mL) and the filtrate was concentrated under reduced pressure to give the title compound together with some 4-Chloroaniline (≈3:2).

Yield: 2.62 g, qu $^1$H-NMR (CDCl$_3$): 1.30-1.75 (m, 8H), 2.69 (t, J=6.8 Hz, 2H), 3.07 (t, J=7.1 Hz, 2H), 3.63 (s, br, 2H), 6.50 (d, J=8.9 Hz, 2H), 7.10 (d, J=8.9 Hz, 2H).

This material was used in the next step without further purification.

Example 59

(rac) 6-(4-Chloro-phenoxy)-1-methyl-hexylamine

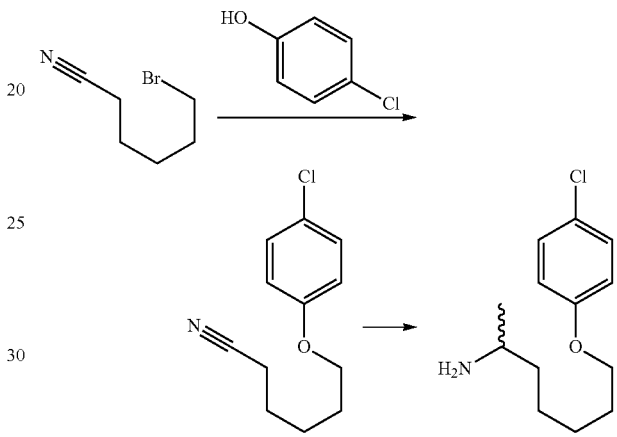

The title compound was synthesized in a two step reaction:

1. 6-(4-Chloro-phenoxy)-hexanenitrile

6-Bromohexanenitrile (2.65 mL, 20 mmol) and 4-chlorophenol (2.57 g, 20 mmol) were dissolved in DMF (50 mL). After addition of K$_2$CO$_3$ (5.53 g, 40 mmol) the mixture was stirred at 95° C. for 3 h. The solvent was evaporated under reduced pressure and the residue was partitioned between water (80 mL) and Et$_2$O (200 mL). The org. layer was separated, washed with pH 7 phosphate buffer solution (1×50 ml), dried over Na$_2$SO$_4$, filtered and the solvent was removed under reduced pressure to give the title compound, pure enough for further reactions.

Yield: 4.10 g, 92%

$^1$H-NMR (CDCl$_3$): 1.58-1.90 (m, 6H), 2.38 (t, J=6.9 Hz, 2H), 3.94 (t, J=6.1 Hz, 2H), 6.81 (d, J=8.9 Hz, 2H), 7.22 (d, J=8.9 Hz, 2H).

2. (rac) 6-(4-Chloro-phenoxy)-1-methyl-hexylamine

Magnesium (120 mg, 5 mmol) was added to Et$_2$O (15 mL), followed by Methyl iodide (310 μl, 5 mmol). After reflux has ceased, the mixture was heated to reflux for 20 min. The solution was than cooled to 0° C. and 6-(4-chloro-phenoxy)-hexanenitrile (1119 mg, 5 mmol) was added. The ice bath was removed and the mixture was stirred at ambient temperature for 20 h. The mixture was then diluted with dry THF (5 mL) ad cooled to −78° C. NaBH$_4$ (190 mg, 5 mmol) was added followed by MeOH (3.5 ml) and stirring was continued at −78° C. for 4.5 h. The reaction was quenched by careful addition of 1M aqueous HCl (20 mL). The layers were separated, the aqueous layer was washed with Et$_2$O (1×25 mL), the organic layer was extracted with 1M aqueous HCl (3×30 mL). The aqueous layers were adjusted to pH 12 by addition of 10M aqueous NaOH (8 mL) and extracted with EtOAc (3×50 mL). The combined org. layers were dried over $Na_2SO_4$, filtered and the solvent was removed under reduced pressure to give the title compound (ca 30% of total by integration of HPLC trace at 218 nm) together with two more hydrophobic byproducts (total: 766 mg).

MS: m/z=242 (MH$^+$),

This crude mixture was used in the next step.

Example 60

6-[4-(Morpholinomethyl)phenoxy]hexylamine

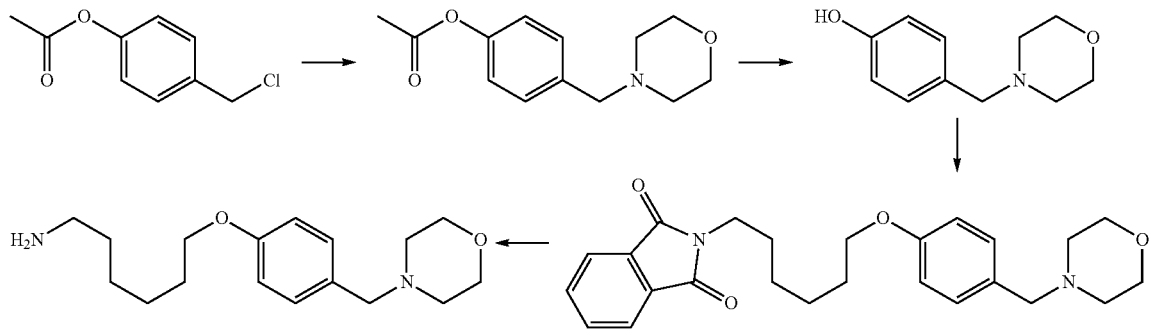

The title compound was synthesized in a four step reaction:

1. 4-(Morpholinomethyl)phenyl acetate

To 4-(chloromethyl)phenyl acetate (2.5 g, 13.5 mmol) was added neat morpholine (3.0 mL, 34.4 mmol) at r.t. The solution was heated to 70° C. for 45 min, then cooled. Water (10 mL) was added and the solution was extracted with 10% methanol in dichloromethane (4×20 mL). The combined organics were washed with brine, dried with $Na_2SO_4$, and concentrated. Purification on silica gel (10% methanol/dichloromethane) gave the title compound.

Yield: 1.9 g, 60%

$^1$H-NMR (CD$_3$OD): 7.14 (d, J=8.4 Hz, 2H), 6.74 (d, J=8.4 Hz, 2H), 3.69-3.52 (m, 6H), 3.42 (s, 2H), 2.44 (m, 4H), 2.09 (s, 3H).

MS: m/z=236 (MH$^+$).

2. 4-(Morpholinomethyl)phenol

To a solution of 4-(morpholinomethyl)phenyl acetate (1.9 g, 8.1 mmol) in 1:1 methanol/water (40 mL) at 0° C. was added LiOH.H$_2$O (339 mg, 8.1 mmol). The reaction was stirred at RT for 2 h. The mixture was concentrated to remove methanol, and the aqueous layer acidified with 3 N HCl. The aqueous layer was extracted with ethyl acetate (4×30 mL) and the organics dried and concentrated to give 454 mg recovered starting material. The aqueous layer was then made basic again (to pH 9) with 1 N NaOH and extracted with ethyl acetate (7×20 mL). These combined organics were washed with brine, dried with $Na_2SO_4$, and concentrated to give a white solid.

Yield: 776 mg, 65% (76% conv)

$^1$H-NMR (CD$_3$OD): 7.14 (d, J=8.1 Hz, 2H), 6.74 (d, J=8.1 Hz, 2H), 3.67 (m, 4H), 3.42 (s, 2H), 2.44 (m, 4H).

MS: m/z=194 (MH$^+$).

3. N-(6-[4-(Morpholinomethyl)phenoxy]hexyl)phthalimide

To a solution of 4-(morpholinomethyl)phenol (776 mg, 4.0 mmol) and N-(6-bromohexyl)phthalimide (1.24 g, 4.0 mmol) in DMF (10 mL) was added $K_2CO_3$ over 2 min. The reaction was heated to 90° C. for 3 h, then stirred at r.t. overnight. The mixture was concentrated and water (10 mL) added. This was extracted with ether (3×30 mL) and the combined organics washed with pH 7 phosphate buffer (20 mL), dried with $Na_2SO_4$, and concentrated to give the title compound as a clear oil.

Yield: 1.66 g, 98%

$^1$H-NMR (CDCl$_3$): 7.84 (m, 2H), 7.71 (m, 2H), 7.20 (d, J=8.7 Hz, 2H), 6.82 (d, J=8.7 Hz, 2H), 3.92 (t, J=6.4 Hz, 2H), 3.70-3.66 (m, 6H), 3.42 (s, 2H), 2.42-2.39 (m, 4H), 1.76-1.74 (m, 5H), 1.45-1.40 (m, 5H).

4. 6-[4-(Morpholinomethyl)phenoxy]hexylamine

To a solution of N-(6-[4-(morpholinomethyl)phenoxy]hexyl)phthalimide (1.66 g, 3.94 mmol) in 1:1 ethanol/THF (28 mL) under nitrogen atmosphere was added hydrazine hydrate (1.4 mL, 29 mmol). The reaction was heated to reflux overnight, then cooled and concentrated. THF was added (30 mL) and the mixture sonicated for 30 min, followed by filtration. The filtrate was concentrated, redissolved in 10 mL THF, and dried with $Na_2SO_4$. Concentration gave the title compound.

Yield: 1.32 g, qu $^1$H-NMR (CDCl$_3$): 7.20 (d, J=8.4 Hz, 2H), 6.82 (d, J=8.7 Hz, 2H), 3.93 (t, J=6.4 Hz, 2H), 3.74-3.67 (m, 6H), 3.42 (s, 2H), 2.68 (t, J=6.9 Hz, 2H), 2.42-2.39 (m, 4H), 1.84-1.76 (m, 4H), 1.49-1.42 (m, 10H).

B: Biological Activity Assays (examples 61-64).

Compounds of the invention were synthesized as described above. All compounds, with the exception of those indicated below, were transferred to their HCl salt by dissolving them in dioxane (4 mL) and 1 M aq. HCl (1 mL) and subsequent freeze drying. The compound of example 1A was transferred to its HCl salt by dissolving it in tert-butanol/water (5 mL) and 1 M aq. HCl (2 µL) and subsequent freeze drying. The compounds of examples 25 and 25 were transferred to their bis-HCl salts by dissolving it them dioxane and 1 M aq. HCl and subsequent freeze drying. For the compound of example 28 the TFA salt was used.

Compounds were prepared for i.p., i.v. or oral administration in a biocompatible vehicle. All preparations are made fresh and injection volumes are adjusted to body weight (0.2 ml/20 g mouse).

The biological activity and utility of the compounds of the invention are demonstrated by one or more assays including those described in more detail below.

Example 61

In Vitro Activity of Compounds of the Present Invention Against a Broad Range of Cancer Cell Lines We observed the surprising finding that compounds of the invention were useful in inhibiting or killing a large variety of tumor cells. Tumor cell lines tested include the cell lines shown in Table 1.

3,000-15,000 cells/well were exposed to the test compounds at a concentration of 1 µM for 48 hours, and cytotoxicity was measured using the SRB assay according to Shekan et al (J Natl Cancer Inst (1990) 82, 1107-112). Briefly, cells were plated in 96 well dishes 24 hours prior to compound addition. The assay was terminated with the addition of cold TCA to a final concentration of 10% and the plates were incubated for one hour at 4° C. The plates were then washed 5 times with water and 100 µl of a Sulforhodamine B solution (4%) was added to each well. The plate was then incubated for 10 minutes at room temperature before removal of unbound dye by washing with 1% acetic acid. The bound dye was solubilized with 10 mM Trizma base and the absorbance read at OD570. Inhibitory activity of the compounds was calculated as % inhibition compared to cells treated with the solvent (DMSO). Table 2 represents the growth inhibitory activity of certain compounds of the invention across a number of tumor cell lines.

Table 2 shows the level of inhibition of six tumor cell lines after incubation with 1 µM of the compounds of the present invention. All compounds demonstrated a clear and pronounced anti-proliferative activity towards a broad panel of cancer cell lines. This surprising effect over a large variety of different cancer cell lines indicates that the subject compounds have strong anti-cancer activity.

Example 62

Determination of the IC50 of Compounds of the Present Invention

We characterized the anti-proliferative activity of some compounds of the present invention by determining their IC50 values.

The assay was performed similar to example 61. However, test compounds were added at various concentrations, such as from 0.001 to about 0.1 µM, from 0.1 to about 10 µM, or from 1 to about 10 µM, as the need may be, in order to estimate the IC50 values. IC50 values were determined by plotting the percentage inhibitory activity for each concentration, fitting a curve using appropriate software and estimating the concentration at which 50% inhibition of growth would occur.

The strong anti-proliferative activity, as determined in example 61, was further characterized. Table 3 represents the estimated IC50 values of certain compounds of the invention across a number of tumor cell lines. It can be seen that all of the compounds show strong anti-proliferative activity, with some compounds showing such activity in the low micromolar range.

Example 63

Clonogenic Survival Assay with HCT-116 Cells

With this assay we determine the concentration of a compound which leads to the irreversible loss of viability after a specified period of exposure. All steps are performed using aseptic techniques.
Protocol:
(1) Incubate and grow cells at 37° C. 5% $CO_2$.
 Pre-warm media (RPMI-1640, 10% FCS, pen/strep) to 37° C. by placing in water bath. Rinse bottle with 70% ethanol prior to use.
(2) Recover cells by trypsinization from sub-confluent plates and count using a hemocytometer.
(3) Plate $1\times10^4$ cells in 25 ml of media in a 15 cm tissue culture dish. Set up 14 plates for each compound to be tested. Incubate overnight at 37° C.
(4) Dilute the compound into media at the appropriate concentrations and replace the medium on the cells with the medium containing compound. Set up two plates for each concentration of the compound to be tested, as well as two without compound.
(5) Incubate plates for 24 hours at 37° C. 5% $CO_2$.
(6) Remove media from cells and replace with fresh media.
(7) Incubate for 7 days as above.
(8) Wash with PBS.
(9) Stain colonies with crystal violet solution (0.4% crystal violet, 20% ethanol) for 5 minutes.
(10) Wash twice with $dH_2O$.
(11) Count colonies.

Compounds of the present invention lead to an irreversible loss of viability of HCT-116 cells after 24 hours of exposure to the compounds of the present invention. Said compounds not only lead to an growth arrest, but cause an irreversible loss of viability.

Example 64

Activity of Compounds in Xenograft Tumor Models

With this assay we demonstrate in-vivo activity of compounds of the present invention.
Mice/Husbandry.
Mice are obtained from Charles River, housed in static microisolators, and provided ad libitum with water and an irradiated standard rodent diet (Purina Pico-Lab Rodent Diet 20).
Determination of Maximum Tolerated Dose (MTD).
Mice at 8 weeks of age are pair-matched into groups of 5-8 animals and preliminary toxicity studies are performed with unknown test compounds. Animals are treated i.v. daily for 10 consecutive days with test compound and are weighed twice weekly. Mice are examined frequently for clinical signs of any adverse drug-related effects. Acceptable toxicity for anticancer drugs in mice is defined by the NCI as no mean group weight loss of over 20% and not more than 10% toxic death in treated animals.
Standard Protocol.
Experiments in Athymic Mice.
Athymic nude mice (male or female, 6-7 weeks; athymic nude mice are hairless, lack a normal thymus gland, and have a defective immune system because of a genetic mutation) are implanted s.c. with single 1 $mm^3$ tumor fragments (tumor brie) or alternatively, 5-10×$10^6$ tissue culture-derived cells into the flank. Animals are initially monitored twice weekly for tumor growth and then daily as the implants approach the desired size of approximately 100 $mm^3$. When the tumors grow to between 50-250 mg in calculated tumor weight, the animals are pair-matched into appropriate experimental treatment groups (8-10 animals/group) and treatment with test compounds is initiated. A positive control is dosed according to historical controls. Tumor weights are calculated and body weights are taken twice weekly and animals are observed frequently for adverse drug effects. The protocol calls for any animal whose tumor mass reaches 1,000 mg to be immediately euthanized.

Tumors are measured by determining the length and width of the tumor with a digital caliper. Tumor weight is estimated using the following formula:

$$\text{Tumor Weight (mg)} = (w^2 \times l)/2$$

where w=width and l=length in mm of the tumor. These values can also be expressed in volumetric units ($mm^3$).

Experimental treatment may cause partial regression (PR) or complete regression (CR) of tumors. PR is where the tumor size is 50% or less of the starting (day 1) size but greater than 0.0 mg for three consecutive days during the course of the study, whereas a CR occurs when there is no measurable tumor mass for three consecutive days. Cures are defined as animals whose tumor shrinks to 0 mg and remains that way until the completion of the experiment.

Log cell kill (LCK) is a calculation that determines the percentage of tumor cells that are killed after the initiation of treatment and can be used as a quantitative measure of efficacy:

$$\text{Log Cell Kill (LCK)} = (T-C)/(3.32)(Td)$$

where T=is the mean time required for the treatment group of mice to reach 1,000 mg in size, C=the mean time for the control group tumors to reach 11000 mg in size, Td=is the tumor doubling time estimated from the linear regression analysis from a semi-log growth plot of the control group tumors during exponential growth and 3.32=the number of doublings required for a population to increase 1-log10 unit. Each LCK unit represents 1-log10 unit of cell killing (e.g. 1 LCK=90% kill, 2 LCK=99% kill, etc.). We consider compounds to be significantly active when they have LCK values >1, which corresponds to >90% tumor cell kill.

Tumor growth inhibition (TGI) is a calculation that describes the amount of tumor growth that is inhibited by treatment with a compound over a defined period of time. It is expressed as:

$$\% \text{ TGI} = 100(1 - T/C)$$

where T is the mean tumor size of a compound treated group on a given day, and C is the mean tumor size of the vehicle control group on the same day.

Toxic deaths are defined as deaths caused by compound treatment and not by advanced disease state. A death is considered toxic if the animal dies within 1 week after the final compound treatment and the tumor size has not reached 1,000 mg. Non-tumor related deaths after this point are recorded, but not considered toxic deaths.

Tumor regression is defined according the following conventions: a regression is defined as partial (PR) if the tumor weight decreases to <50% of the starting weight (<50 mg). A regression is defined as complete (CR) if the tumor weight decreases below measurable weight during the experimental period. A cure is defined as a tumor-free animal at end of the observation period.

Similarly, experiments are performed in a syngeneic ip/ip mouse model.

Results.

Compounds of the present invention show the following effects in the describe xenograft mouse model: (1) weight and size of tumors are smaller for compound treated animals as compared to the control groups, (2) Log cell kill (LCK) is higher for compound treated animals as compared to the control groups, and (3) Tumor growth inhibition (TGI) is higher for compound treated animals as compared to the control groups.

C: Selection and Development of Drug Candidates (Example 65).

Example 65

In order to select the most appropriate compound to enter further experiments and to assess its suitability for use in a therapeutic composition for the treatment of disorders and diseases, such as cancers, additional data are collected. Such data can include the in vitro killing efficiency as measured by IC50 and cytotoxicity across a panel of tumor cell lines, the percentage cell killing as estimated in vitro, and tumor reduction data and mouse survival data from in vivo animal models. Furthermore, such experiments may also include the elucidation and/or determination of the mechanism of action of the subject compound, the target of the subject compound, and other characteristics of the subject compound, such as the binding affinity of the compound to the target or the binding site of the compound on the target. Such experiments may also include molecular modelling of the drug-target interaction.

The compound that shows the lowest IC50 for killing, the highest percentage cell killing and broadest across various tumor cell lines, the best tumor reduction data and/or the best mouse-survival data may be chosen to enter further experiments. Such experiments may include, for example, therapeutic profiling and toxicology in animals, phase I clinical trials in humans and other clinical trails.

One skilled in the art readily appreciates that the present invention is well adapted to carry out the objects and obtain the ends and advantages mentioned, as well as those inherent therein. The methods and reagents described herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Those skilled in the art will recognize, or be able to ascertain using no more than routine experimentation, many equivalents to the specific embodiments of the invention described herein. Such equivalents are intended to be encompassed by the following claims. Those skilled in the art will also recognize that all combinations of embodiments, combination of aspects or features of the claims described herein are within the scope of the invention.

TABLE 1

Tumor cell lines

| Cell line | Depository | Order Number | Source/disease | Reference(s) |
| --- | --- | --- | --- | --- |
| A2780 | ECACC | 93112519 | Human ovarian carcinoma | Semin Oncol (1984) 11: 285; Cancer Res (1987) 47: 414. |
| HCT-116 | ATCC | CCL-247 | Colorectal carcinoma | Cancer Res (1981) 41: 1751; Cancer (1995) 76: 201. |

TABLE 1-continued

Tumor cell lines

| Cell line | Depository | Order Number | Source/disease | Reference(s) |
|---|---|---|---|---|
| PC-3 | ATCC | CRL-1435 | Prostatic adenocarcinoma | Invest Urol (1979) 17: 16; Cytogenet Cell Genet (1993) 62: 183. |
| SW-620 | ATCC | CCL-227 | Colorectal adenocarcinoma | Cancer Res (1976) 36: 4562. J Natl Cancer Inst (1977) 59: 221. |
| MCF7 | ATCC | HTB-22 | Breast carcinoma | J Natl Cancer Inst (1973) 51: 1409; Cancer Res (1993) 53: 5193. |
| A-549 | ATCC | CCL-185 | Lung carcinoma | J Natl Cancer Inst (1973) 51: 417; Int J Cancer (1976) 17: 62. |

TABLE 2

Inhibition of tumor cell growth as determined in Example 61

% Inhibition (1 µM)

| Compound | A2780 | HCT-116 | PC-3 | SW-620 | MCF7 | A-549 |
|---|---|---|---|---|---|---|
| SQ-1B | >80 | >80 | >50 | >20 | >80 | >20 |
| SQ-2 | >80 | >80 | >50 | >50 | >80 | >50 |
| SQ-3 | >80 | >80 | >50 | >50 | >5 | >50 |
| SQ-4 | >80 | >80 | >50 | >50 | | >50 |
| SQ-5 | >80 | >80 | >50 | 0 | >50 | |
| SQ-7B | >80 | >80 | >50 | >50 | | |
| SQ-8 | >80 | >80 | >50 | >20 | >80 | >5 |
| SQ-9 | >80 | >80 | >50 | >50 | >80 | >5 |
| SQ-10 | >50 | >50 | | >20 | >50 | 0 |
| SQ-11A | >80 | >80 | >20 | >50 | >80 | >5 |
| SQ-11B | >80 | >80 | >50 | >50 | >80 | >50 |
| SQ-12 | >80 | >80 | >50 | >20 | >20 | >50 |
| SQ-13 | >80 | >80 | >50 | >20 | >5 | >20 |
| SQ-14 | >80 | >80 | >50 | >20 | >5 | >20 |
| SQ-15 | >80 | >80 | >50 | >20 | >20 | >20 |
| SQ-16 | >80 | >80 | >20 | >20 | >5 | >20 |
| SQ-17 | >80 | >80 | >50 | >20 | | >50 |
| SQ-18 | >80 | >80 | >50 | >20 | | >20 |
| SQ-19 | >50 | >5 | >5 | >5 | | >0 |
| SQ-22 | >80 | >80 | >50 | >50 | >20 | >50 |
| SQ-23 | >80 | >80 | >50 | >20 | | >50 |
| SQ-24 | >80 | >80 | >50 | >50 | >20 | >50 |
| SQ-25 | >80 | >80 | >50 | >20 | >5 | >20 |
| SQ-26 | >80 | >80 | >50 | >20 | >5 | >50 |
| SQ-27 | >80 | >80 | >50 | >20 | >20 | >50 |
| SQ-30 | >80 | >80 | >20 | >20 | >80 | >50 |
| SQ-32 | >80 | >80 | >50 | >5 | >20 | >20 |
| SQ-33 | >20 | >50 | 0 | >5 | 0 | 0 |
| SQ-34 | >20 | >20 | >0 | 0 | 0 | 0 |
| SQ-39 | >80 | >80 | >20 | >20 | >5 | >50 |

TABLE 3

IC50 values as determined in Example 62

IC$_{50}$ (µM)

| RGB | A2780 | HCT-116 | PC-3 | SW-620 | MCF7 | A-549 |
|---|---|---|---|---|---|---|
| SQ-1B | <0.1 | <0.02 | | <2 | <0.01 | |
| SQ-2 | <0.02 | <0.02 | | <10 | <0.02 | |
| SQ-3 | | <0.1 | | <0.5 | <10 | <0.5 |
| SQ-4 | | <0.1 | | <2 | <10 | <0.5 |
| SQ-5 | | <0.1 | | <2 | <10 | |
| SQ-6 | <0.02 | <0.1 | <0.5 | | | |
| SQ-7B | <0.1 | <0.1 | | | <0.1 | |
| SQ-8 | | <0.1 | | <2 | <0.1 | |
| SQ-9 | | | | <2 | <0.5 | |
| SQ-10 | | <2 | | <10 | <2 | |
| SQ-11A | | <0.1 | | <2 | <0.1 | |
| SQ-11B | | <0.02 | | <0.5 | <0.02 | |
| SQ-12 | <0.02 | <0.02 | | | <10 | <2 |
| SQ-13 | | <0.1 | | <2 | | |
| SQ-14 | | <0.1 | | <2 | | |
| SQ-15 | | <0.1 | | <0.5 | | |
| SQ-16 | <0.1 | <0.5 | <0.5 | | | |
| SQ-17 | <0.1 | <0.02 | | <0.5 | <10 | |
| SQ-18 | | | | <2 | <10 | |
| SQ-20 | <0.02 | <0.1 | <0.5 | | | |
| SQ-22 | <0.02 | <0.02 | <0.02 | | | |
| SQ-23 | <0.02 | <0.02 | <0.02 | | <0.5 | <0.02 |
| SQ-24 | <0.02 | <0.02 | <0.1 | <2 | | <0.1 |
| SQ-25 | | <0.5 | | <2 | | |
| SQ-26 | | <0.1 | | <2 | | |
| SQ-27 | | <0.1 | | <0.5 | | <2 |
| SQ-30 | | <2 | | >10 | <0.5 | |
| SQ-32 | <0.1 | <0.1 | | >10 | >10 | |
| SQ-35 | <10 | <10 | >10 | | | |
| SQ-37 | <2 | <2 | <10 | | | |
| SQ-38 | <10 | <10 | <10 | | | |
| SQ-39 | <0.02 | <0.02 | <0.1 | | | |

TABLE 4

Examplary compounds of the present invention

| Compound number | Structure | Compound name |
|---|---|---|
| SQ-7B | (structure image) | 3-[6-(4-Chloro-phenoxy)-hexylamino]-4-(pyridin-4-ylamino)-cyclobut-3-ene-1,2-dione |

TABLE 4-continued

Examplary compounds of the present invention

| Compound number | Structure | Compound name |
|---|---|---|
| SQ-1B | 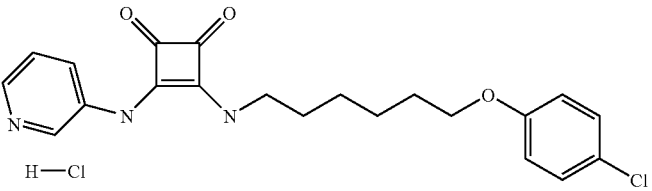 | 3-[6-(4-Chloro-phenoxy)-hexylamino]-4-(pyridin-3-ylamino)-cyclobut-3-ene-1,2-dione |
| SQ-8 | 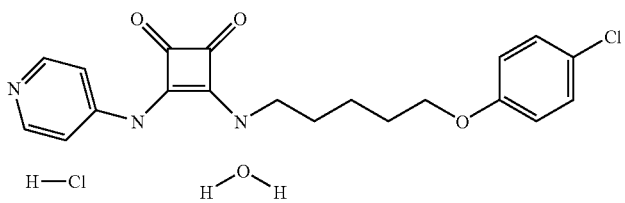 | 3-[5-(4-Chloro-phenoxy)-pentylamino]-4-(pyridin-4-ylamino)-cyclobut-3-ene-1,2-dione |
| SQ-9 | 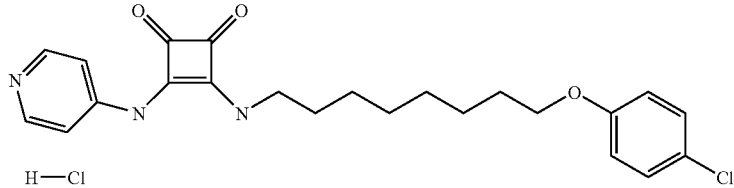 | 3-[8-(4-Chloro-phenoxy)-octylamino]-4-(pyridin-4-ylamino)-cyclobut-3-ene-1,2-dione |
| SQ-10 | 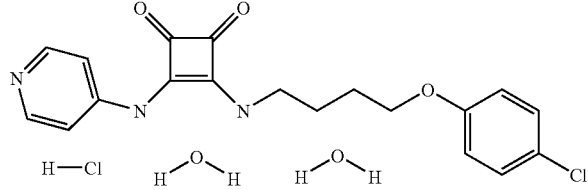 | 3-[4-(4-Chloro-phenoxy)-butylamino]-4-(pyridin-4-ylamino)-cyclobut-3-ene-1,2-dione |
| SQ-11A | 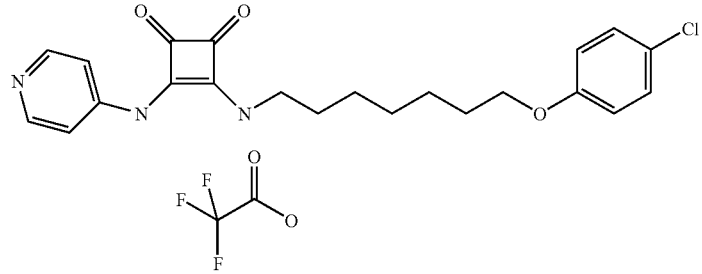 | 3-[7-(4-Chloro-phenoxy)-heptylamino]-4-(pyridin-4-ylamino)-cyclobut-3-ene-1,2-dione |
| SQ-11B | 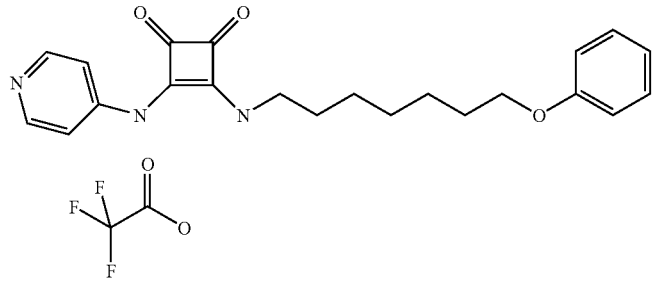 | 3-(7-Phenoxy-heptylamino)-4-(pyridin-4-ylamino)-cyclobut-3-ene-1,2-dione |
| SQ-2 | 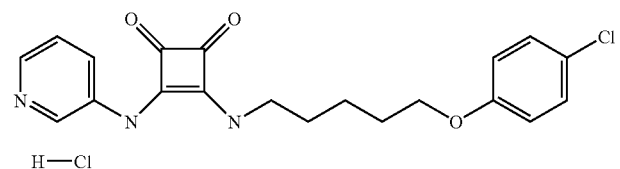 | 3-[5-(4-Chloro-phenoxy)-pentylamino]-4-(pyridin-3-ylamino)-cyclobut-3-ene-1,2-dione |

TABLE 4-continued

Examplary compounds of the present invention

| Compound number | Structure | Compound name |
| --- | --- | --- |
| SQ-30 | 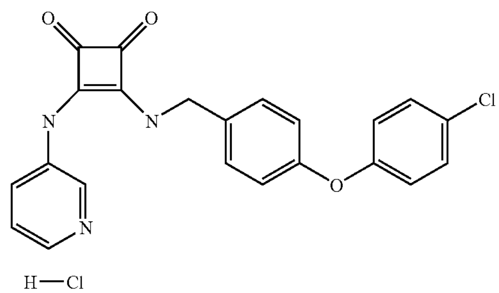 | 3-[4-(4-Chloro-phenoxy)-benzylamino]-4-(pyridin-3-ylamino)-cyclobut-3-ene-1,2-dione |
| SQ-32 | 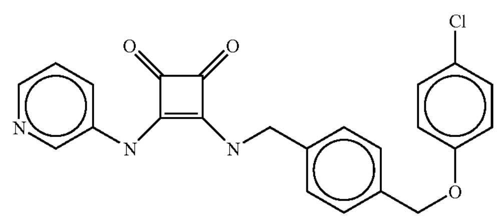 | 3-[4-(4-Chloro-phenoxymethyl)-benzylamino]-4-(pyridin-3-ylamino)-cyclobut-3-ene-1,2-dione |
| SQ-12 | 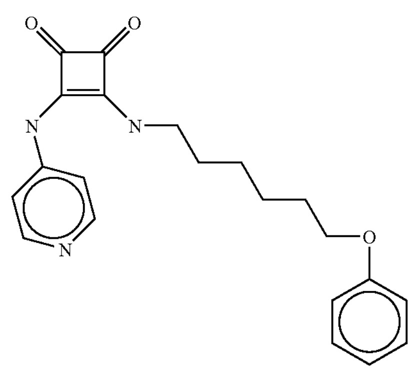 | 3-(6-Phenoxy-hexylamino)-4-(pyridin-4-ylamino)-cyclobut-3-ene-1,2-dione |
| SQ-13 | 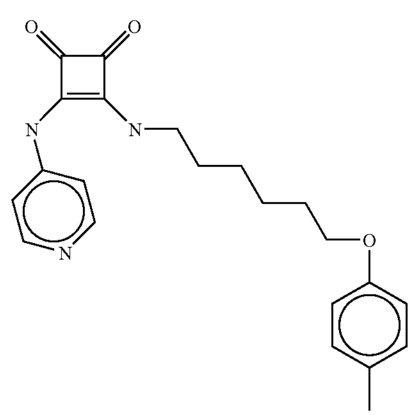 | 3-(Pyridin-4-ylamino)-4-(6-p-tolyloxy-hexylamino)-cyclobut-3-ene-1,2-dione |

TABLE 4-continued

Examplary compounds of the present invention

| Compound number | Structure | Compound name |
| --- | --- | --- |
| SQ-14 | 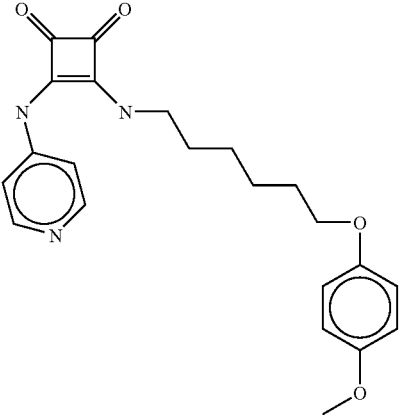 | 3-[6-(4-Methoxy-phenoxy)-hexylamino]-4-(pyridin-4-ylamino)-cyclobut-3-ene-1,2-dione |
| SQ-15 | 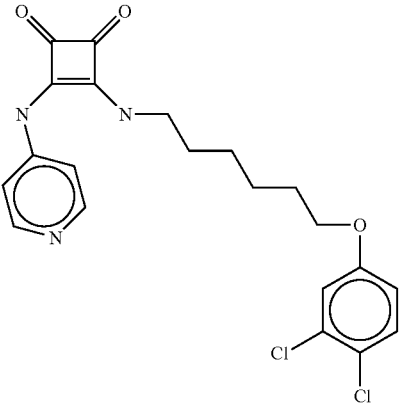 | 3-[6-(3,4-Dichloro-phenoxy)-hexylamino]-4-(pyridin-4-ylamino)-cyclobut-3-ene-1,2-dione |
| SQ-33 | 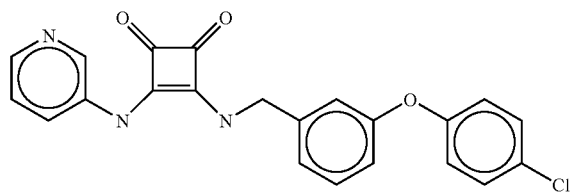 | 3-[3-(4-Chloro-phenoxy)-benzylamino]-4-(pyridin-3-ylamino)-cyclobut-3-ene-1,2-dione |
| SQ-3 | 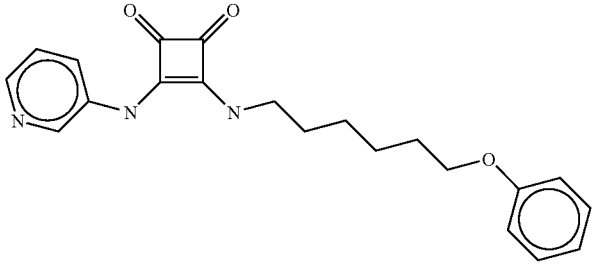 | 3-(6-Phenoxy-hexylamino)-4-(pyridin-3-ylamino)-cyclobut-3-ene-1,2-dione |

TABLE 4-continued

Examplary compounds of the present invention

| Compound number | Structure | Compound name |
| --- | --- | --- |
| SQ-4 | 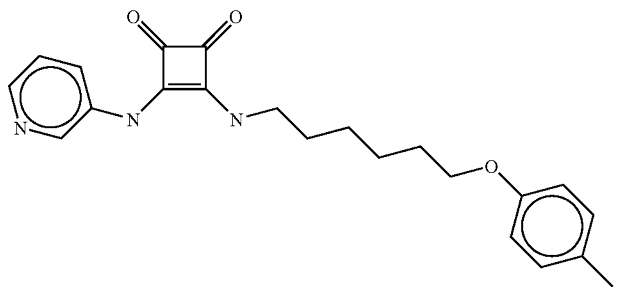 | 3-(Pyridin-3-ylamino)-4-(6-p-tolyloxy-hexylamino)-cyclobut-3-ene-1,2-dione |
| SQ-27 | 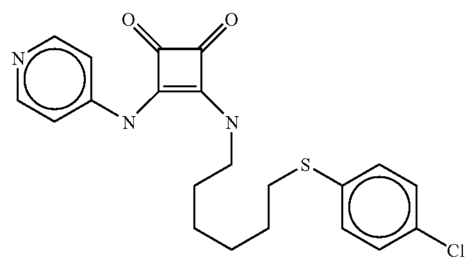 | 3-[6-(4-Chloro-phenylsulfanyl)-hexylamino]-4-(pyridin-4-ylamino)-cyclobut-3-ene-1,2-dione |
| SQ-24 | 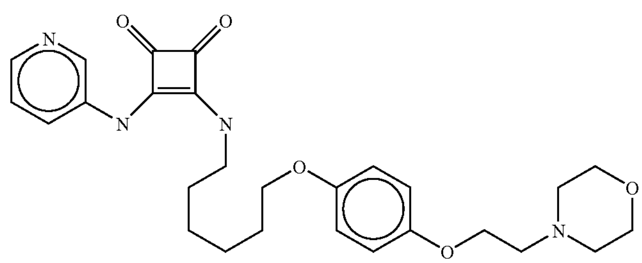 | 3-{6-[4-(2-Morpholin-4-yl-ethoxy)-phenoxy]-hexylamino}-4-(pyridin-3-ylamino)-cyclobut-3-ene-1,2-dione |
| SQ-26 | 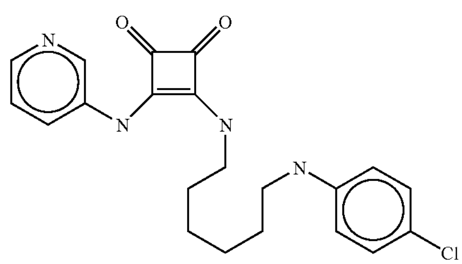 | 3-[6-(4-Chloro-phenylamino)-hexylamino]-4-(pyridin-3-ylamino)-cyclobut-3-ene-1,2-dione |
| SQ-25 | 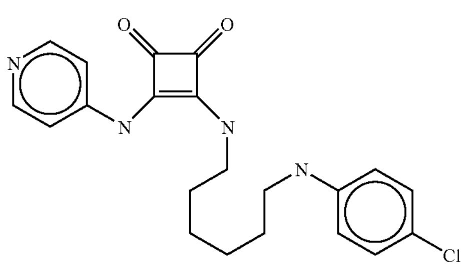 | 3-[6-(4-Chloro-phenylamino)-hexylamino]-4-(pyridin-4-ylamino)-cyclobut-3-ene-1,2-dione |
| SQ-34 | 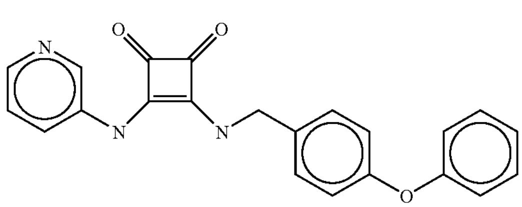 | 3-(4-Phenoxy-benzylamino)-4-(pyridin-3-ylamino)-cyclobut-3-ene-1,2-dione |

TABLE 4-continued

Examplary compounds of the present invention

| Compound number | Structure | Compound name |
|---|---|---|
| SQ-23 | 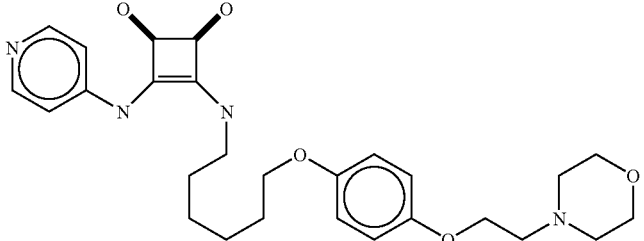 | 3-{6-[4-(2-Morpholin-4-yl-ethoxy)-phenoxy]-hexylamino}-4-(pyridin-4-ylamino)-cyclobut-3-ene-1,2-dione |
| SQ-17 | 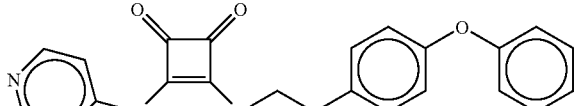 | 3-[2-(4-Phenoxy-phenyl)-ethylamino]-4-(pyridin-4-ylamino)-cyclobut-3-ene-1,2-dione |
| SQ-5 | 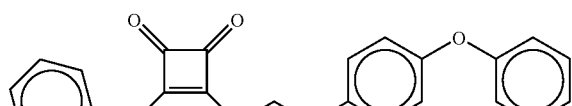 | 3-[2-(4-Phenoxy-phenyl)-ethylamino]-4-(pyridin-3-ylamino)-cyclobut-3-ene-1,2-dione |
| SQ-18 | 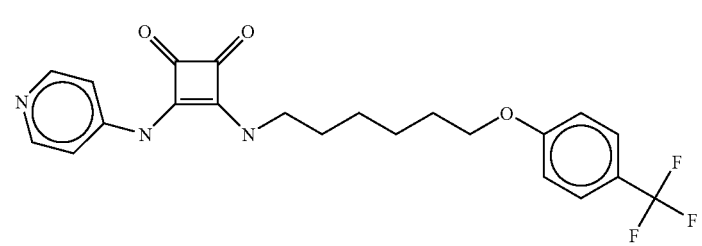 | 3-(Pyridin-4-ylamino)-4-[6-(4-trifluoromethyl-phenoxy)-hexylamino]-cyclobut-3-ene-1,2-dione |
| SQ-19 | 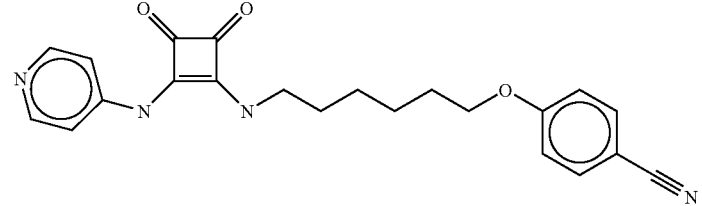 | 4-{6-[3,4-Dioxo-2-(pyridin-4-ylamino)-cyclobut-1-enylamino]-hexyloxy}-benzonitrile |
| SQ-22 | 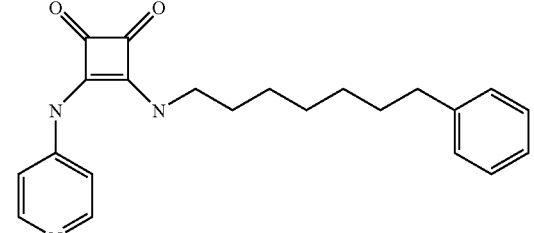 | 3-(7-Phenyl-heptylamino)-4-(pyridin-4-ylamino)-cyclobut-3-ene-1,2-dione |
| SQ-16 | 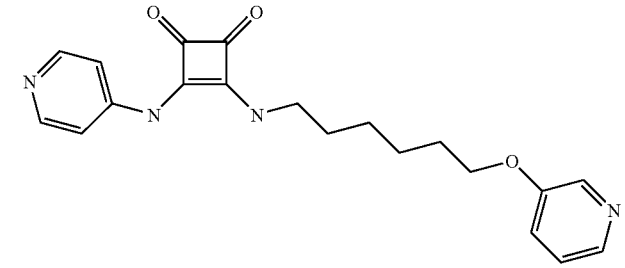 [SMILES: O=c1c(NCCCCCCOc2cccnc2)c(Nc2ccncc2)c1=O] | 3-(Pyridin-4-ylamino)-4-[6-(pyridin-3-yloxy)-hexylamino]-cyclobut-3-ene-1,2-dione |

TABLE 4-continued

Examplary compounds of the present invention

| Compound number | Structure | Compound name |
|---|---|---|
| SQ-39 | 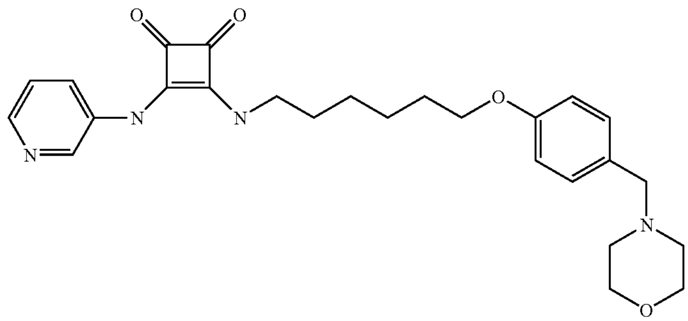 [SMILES: O=c1c(NCCCCCCOc2ccc(CN3CCOCC3)cc2)c(Nc2cccnc2)c1=O] | 3-[6-(4-Morpholin-4-ylmethyl-phenoxy)-hexylamino]-4-(pyridin-3-ylamino)-cyclobut-3-ene-1,2-dione |
| SQ-35 | 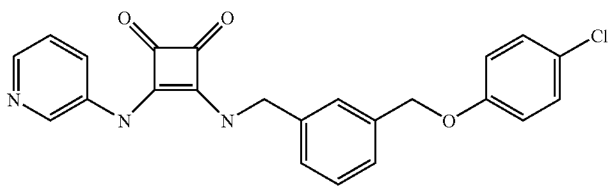 [SMILES: O=c1c(NCc2cccc(COc3ccc(Cl)cc3)c2)c(Nc2cccnc2)c1=O] | 3-[3-(4-Chloro-phenoxymethyl)-benzylamino]-4-(pyridin-3-ylamino)-cyclobut-3-ene-1,2-dione |
| SQ-20 | 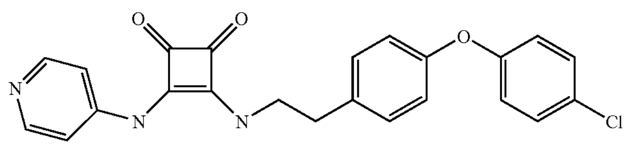 [SMILES: O=c1c(NCCc2ccc(Oc3ccc(Cl)cc3)cc2)c(Nc2ccncc2)c1=O] | 3-{2-[4-(4-Chloro-phenoxy)-phenyl]-ethylamino}-4-(pyridin-4-ylamino)-cyclobut-3-ene-1,2-dione |
| SQ-5 | 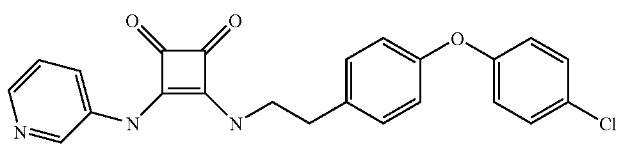 [SMILES: O=c1c(NCCc2ccc(Oc3ccc(Cl)cc3)cc2)c(Nc2cccnc2)c1=O] | 3-{2-[4-(4-Chloro-phenoxy)-phenyl]-ethylamino}-4-(pyridin-3-ylamino)-cyclobut-3-ene-1,2-dione |
| SQ-37 | 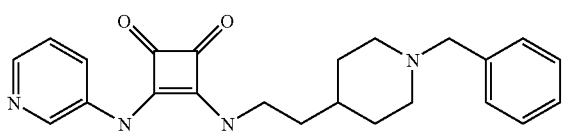 [SMILES: O=c1c(NCCC2CCN(Cc3ccccc3)CC2)c(Nc2cccnc2)c1=O] | 3-[2-(1-Benzyl-piperidin-4-yl)-ethylamino]-4-(pyridin-3-ylamino)-cyclobut-3-ene-1,2-dione |
| SQ-38 | 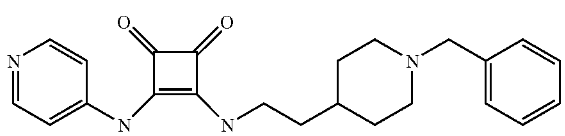 [SMILES: O=c1c(NCCC2CCN(Cc3ccccc3)CC2)c(Nc2ccncc2)c1=O] | 3-[2-(1-Benzyl-piperidin-4-yl)-ethylamino]-4-(pyridin-4-ylamino)-cyclobut-3-ene-1,2-dione |

What is claimed is:

1. A compound of general formula (Ia):

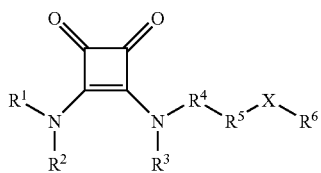

(Ia)

wherein
R$^1$ is 3-pyridyl or 4-pyridyl;
R$^2$ and R$^3$ are each hydrogen;
R$^4$ is CH$_2$—;
R$^5$ is a linker moiety selected from the group consisting of C$_2$-C$_{10}$ alkylene, C$_2$-C$_{10}$ alkenylene, C$_2$-C$_{10}$ alkynylene, which linker moiety is substituted by p substituents R$^9$ (where p is an integer from 0 to 10);
X is absent or selected from the group consisting of —O—, —S— and —NH—;
R$^6$ is phenyl wherein said phenyl is substituted with 0-10 substituents R$^{10}$;
each R$^9$ and R$^{10}$ is independently selected from the group consisting of alkyl, alkenyl, alkynyl, alkoxy, aryl, aralkyl, cycloalkyl, cycloalkylalkyl, haloalkyl, haloalkenyl, haloalkynyl, heterocyclyl, heterocyclylalkyl, halo, nitro, cyano, hydroxy, amino, carboxy, —OR$^{11}$, —NHR$^{11}$, —NR$^{11}$R$^{12}$, —C(O)H, —C(O)R$^{11}$, —OC(O)R$^{11}$, —C(O)OR$^{11}$, —C(O)NHR$^{11}$, —C(O)NR$^{11}$R$^{12}$, —S(O)xR$^{11}$ (where X is 0 to 2), —S(O)$_2$OR$^{11}$, —R$^{13}$-nitro, —R$^{13}$-cyano, —R$^{13}$-hydroxy, —$R^{13}$-amino, —$R^{13}$-carboxy, —$R^{13}$—$OR^{11}$, —$R^{13}$—$NHR^{11}$, —$R^{13}$—$NR^{11}R^{12}$, —$R^{13}$—C(O)H, —$R^{13}$—C(O)$R^{11}$, —$R^{13}$—OC(O)$R^{11}$, —$R^{13}$—C(O)O$R^{11}$, —$R^{13}$—C(O)NH$R^{11}$, —$R^{13}$—C(O)N$R^{11}R^{12}$, —$R^{13}$—S(O)x$R^{11}$ (where X is 0 to 2), —$R^{13}$—S(O)$_2$OR11; —O—$R^{13}$-nitro, —O—$R^{13}$-cyano, —O$R^{13}$-hydroxy, —O—$R^{13}$-amino, —O—$R^{13}$-carboxy, —O—$R^{13}$—$OR^{13}$, —O—$R^{13}$—$NHR^{11}$, —O—$R^{13}$—$NR^{11}R^{12}$, —O—$R^{13}$—C(O)H, —$OR^{13}$—C(O)$R^{11}$, —O—$R^{13}$—OC(O)$R^{11}$, —O—$R^{13}$—C(O)O$R^{11}$, —O—$R^{13}$—C(O)NH$R^{11}$, —O—$R^{13}$—C(O)N$R^{11}R^{12}$, —O—$R^{13}$—S(O)x$R^{11}$ (where X is 0 to 2), —O—$R^{13}$—S(O)$_2$O$R^{11}$; —N($R^{14}$)—$R^{13}$-nitro, —N($R^{14}$)—$R^{13}$-cyano, —N($R^{14}$)—$R^{13}$-hydroxy, —N($R^{14}$)—$R^{13}$-amino, —N($R^{14}$)—$R^{13}$-carboxy, —N($R^{14}$)—$R^{13}$—$OR^{11}$, —N($R^{14}$)—$R^{13}$—$NHR^{11}$, —N($R^{14}$)—$R^{13}$—$NR^{11}R^{12}$, —N($R^{14}$)—$R^{13}$—C(O)H, —N($R^{14}$)—$R^{13}$—C(O)$R^{11}$, —N($R^{14}$)—$R^{13}$—OC(O)$R^{11}$, —N($R^{14}$)C(O)$R^{11}$—, —O—$R^{13}$—N($R^{14}$)—C(O)$R^{11}$—, —N($R^{14}$)—$R^{13}$—C(O)O$R^{11}$, —N($R^{14}$)—$R^{13}$—C(O)NH$R^{11}$, —N($R^{14}$)—$R^{13}$—C(O)N$R^{11}R^{12}$, —N($R^{14}$)—$R^{13}$—S(O)x$R^{11}$ (where X is 0 to 2), —N($R^{14}$)—$R^{13}$—S(O)$_2$O$R^{11}$, (morpholin-4-yl) $C_1$-$C_6$ alkyl or (morpholin-4-yl) $C_1$-$C_6$ alkoxy;

$R^{11}$, $R^{12}$ are each independently selected from the group consisting of alkyl, alkenyl, alkynyl, aryl, aralkyl, cycloalkyl, cycloalkylalkyl, haloalkyl, haloalkenyl, haloalkynyl, heterocyclyl, heterocyclylalkyl, or if $R^{11}$ and $R^{12}$ are both bound to a nitrogen atom, together with the nitrogen atom form a 5-7 membered ring consisting of carbon and 0-2 additional heteroatoms selected from the group consisting of O, S and N (where the N is bound to a further substituents selected from the group consisting of hydrogen, alkyl, aryl, and aralkyl), which ring system may be partially unsaturated;

each $R^{13}$ is independently selected from the group consisting of $C_1$-$C_6$ alkylene, $C_1$-$C_6$ alkenylene, C2-$C_6$ alkynylene;

each $R^{14}$ is independently selected from the group consisting of hydrogen, alkyl, alkenyl, alkynyl, aryl, aralkyl, cycloalkyl, cycloalkylalkyl, haloalkyl, haloalkenyl, haloalkynyl, heterocyclyl, heterocyclylalkyl; or tautomers thereof;

as a single stereoisomer or a mixture of stereoisomers; or as a pharmaceutically acceptable salt thereof.

2. The compound of claim 1, wherein $R^1$ is 3-pyridyl.

3. The compound of claim 1, wherein $R^1$ is 4-pyridyl.

4. The compound of claim 1, wherein $R^5$ is $C_2$-$C_{10}$ alkylene.

5. The compound according to claim 1, wherein X is selected from the group consisting of —O—, —S— and NH—.

6. The compound according to claim 1, wherein X is absent or —O—.

7. The compound according to claim 1, wherein X is selected from the group consisting of —O— and —S—.

8. The compound according to claim 1, wherein X is absent.

9. The compound according to claim 1, wherein $R^6$ is substituted with 0-5 substituents $R^{10}$.

10. The compound according to claim 1, wherein $R^6$ is phenyl.

11. The compound according to claim 1, wherein $R^6$ is substituted with halo, alkyl, alkoxy, cyano, (morpholin-4-yl) $C_1$-$C_6$ alkyl or (morpholin-4-yl) $C_1$-$C_6$ alkoxy.

12. The compound of claim 1, wherein the compound is selected from:
- 3-[6-(4-Chloro-phenoxy)-hexylamino]-4-(pyridine-4-ylamino)-cyclobut-3-ene-1,2-dione,
- 3-[6-(4-Chloro-phenoxy)-hexylamino]-4-(pyridine-3-ylamino)-cyclobut-3-ene-1,2-dione,
- 3-[5-(4-Chloro-phenoxy)-pentylamino]-4-(pyridine-4-ylamino)-cyclobut-3-ene-1,2-dione,
- 3-[8-(4-Chloro-phenoxy)-octylamino]-4-(pyridine-4-ylamino)-cyclobut-3-ene-1,2-dione,
- 3-[4-(4-Chloro-phenoxy)-butylamino]-4-(pyridine-4-ylamino)-cyclobut-3-ene-1,2-dione,
- 3-[7-(4-Chloro-phenoxy)-heptylamino]-4-(pyridine-4-ylamino)-cyclobut-3-ene-1,2-dione,
- 3-(7-Phenoxy-heptylamino)-4-(pyridine-4-ylamino)-cyclobut-3-ene-1,2-dione,
- 3-[5-(4-Chloro-phenoxy)-pentylamino]-4-(pyridine-3-ylamino)-cyclobut-3-ene-1,2-dione,
- 3-(6-Phenoxy-hexylamino)-4-(pyridine-4-ylamino)-cyclobut-3-ene-1,2-dione,
- 3-(Pyridin-4-ylamino)-4-(6-p-tolyloxy-hexylamino)-cyclobut-3-ene-1,2-dione,
- 3-[6-(4-Methoxy-phenoxy)-hexylamino]-4-(pyridine-4-ylamino)-cyclobut-3-ene-1,2-dione,
- 3-[6-(3,4-Dichloro-phenoxy)-hexylamino]-4-(pyridine-4-ylamino)-cyclobut-3-ene-1,2-dione,
- 3-(6-Phenoxy-hexylamino)-4-(pyridine-3-ylamino)-cyclobut-3-ene-1,2-dione,
- 3-[6-(4-Chloro-phenylamino)-hexylamino]-4-(pyridine-3-ylamino)-cyclobut-3-ene-1,2-dione,
- 3-[6-(4-Chloro-phenylamino)-hexylamino]-4-(pyridine-4-ylamino)-cyclobut-3-ene-1,2-dione,
- 3-(7-Phenyl-heptylamino)-4-(pyridine-4-ylamino)-cyclobut-3-ene-1,2-dione,
- 3-[4-(4-Chloro-phenoxy)-benzylamino]-4-(pyridine-3-ylamino)-cyclobut-3-ene-1,2-dione,
- 3-[4-(4-Chloro-phenoxymethyl)-benzylamino]-4-(pyridine-3-ylamino)-cyclobut-3-ene-1,2-dione,
- 3-[3-(4-Chloro-phenoxy)-benzylamino]-4-(pyridine-3-ylamino)-cyclobut-3-ene-1,2-dione,
- 3-[4-(4-Chloro-phenoxy)-benzylamino]-4-(pyridine-2-ylamino)-cyclobut-3-ene-1,2-dione,
- 3-(4-Phenoxy-benzylamino)-4-(pyridine-3-ylamino)-cyclobut-3-ene-1,2-dione,
- 3-[3-(4-Chloro-phenoxymethyl)-benzylamino]-4-(pyridine-3-ylamino)-cyclobut-3-ene-1,2-dione,
- 3-{2-[4-(4-Chloro-phenoxy)-phenyl]-ethylamino}-4-(pyridine-4-ylamino)-cyclobut-3-ene-1,2-dione,
- 3-{2-[4-(4-Chloro-phenoxy)-phenyl]-ethylamino}-4-(pyridine-3-ylamino)-cyclobut-3-ene-1,2-dione,
- 3-[2-(4-Phenoxy-phenyl)-ethylamino]-4-(pyridine-4-ylamino)-cyclobut-3-ene-1,2-dione, and
- 3-[2-(4-Phenoxy-phenyl)-ethylamino]-4-(pyridine-3-ylamino)-cyclobut-3-ene-1,2-dione.

13. A pharmaceutical composition comprising a therapeutically effective amount of at least one compound according to claim 1 and a pharmaceutically acceptable carrier and/or diluent.

* * * * *